(12) United States Patent
Breitenkamp et al.

(10) Patent No.: US 8,066,824 B2
(45) Date of Patent: Nov. 29, 2011

(54) COVALENT MODIFICATION OF METAL SURFACES

(75) Inventors: Kurt Breitenkamp, Tampa, FL (US); Rebecca Breitenkamp, Tampa, FL (US); Kevin N. Sill, Tampa, FL (US); Habib Skaff, Tampa, FL (US)

(73) Assignee: Intezyne Technologies, Inc., Tampa, FL (US)

( * ) Notice: Subject to any disclaimer, the term of this patent is extended or adjusted under 35 U.S.C. 154(b) by 502 days.

(21) Appl. No.: 11/825,791

(22) Filed: Jul. 9, 2007

(65) Prior Publication Data
US 2008/0035243 A1 Feb. 14, 2008

Related U.S. Application Data

(60) Provisional application No. 60/819,200, filed on Jul. 7, 2006.

(51) Int. Cl.
*C23C 22/00* (2006.01)

(52) U.S. Cl. .......... 148/251; 148/240; 525/482; 525/523

(58) Field of Classification Search .................. 148/251, 148/240; 525/482, 523
See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 4,768,523 A | 9/1988 | Cahalan et al. |
| 4,776,337 A | 10/1988 | Palmaz et al. |
| 5,041,126 A | 8/1991 | Gianturco |
| 5,052,998 A | 10/1991 | Zimmon |
| 5,064,435 A | 11/1991 | Porter |
| 5,147,370 A | 9/1992 | McNamara et al. |
| 5,176,626 A | 1/1993 | Soehendra |
| 5,304,121 A | 4/1994 | Sahatjian et al. |
| 5,328,471 A | 7/1994 | Slepian |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 5,651,986 A | 7/1997 | Brem et al. |
| 5,886,026 A | 3/1999 | Hunter et al. |
| 6,099,562 A | 8/2000 | Ding et al. |
| 6,299,604 B1 | 10/2001 | Ragheb et al. |
| 6,344,028 B1 | 2/2002 | Barry |
| 6,515,016 B2 | 2/2003 | Hunter et al. |
| 2004/0146715 A1 | 7/2004 | Guire et al. |
| 2004/0234703 A1* | 11/2004 | Frautschi ............ 427/535 |
| 2004/0253203 A1* | 12/2004 | Hossainy et al. ...... 424/78.08 |

(Continued)

OTHER PUBLICATIONS

Huang et al. "Selective deposition of conducting polymers on hydroxyl-terminated surfaces with printed monolayers of alkylsiloxanes as templates" Langmuir. 1997, 13, 6480-6484.

(Continued)

*Primary Examiner* — Roy King
*Assistant Examiner* — Lois Zheng
(74) *Attorney, Agent, or Firm* — Choate, Hall & Stewart, LLP; Andrea L. C. Robidoux, Esq.

(57) ABSTRACT

The present invention provides modified metal surfaces, methods of preparing the same, and intermediates thereto. These materials are useful in a variety of applications including biomaterials.

11 Claims, 12 Drawing Sheets

U.S. PATENT DOCUMENTS

| | | | |
|---|---|---|---|
| 2005/0271810 A1* | 12/2005 | Kobrin et al. | 427/248.1 |
| 2006/0142506 A1* | 6/2006 | Breitenkamp et al. | 525/482 |
| 2006/0172914 A1 | 8/2006 | Breitenkamp et al. | |
| 2006/0240092 A1 | 10/2006 | Breitenkamp et al. | |
| 2008/0188638 A1 | 8/2008 | Breitenkamp et al. | |
| 2008/0207913 A1 | 8/2008 | Breitenkamp et al. | |

OTHER PUBLICATIONS

Mansky et al. "Controlling polymer-surface interactions with random copolymer brushes" Science 1997, 275, 1458-1460.

Granick et al. "Macromolecules at surfaces: research challenges and opportunities from tribology to biology" J. Polym. Sci. B. 2003, 41, 2755-2793.

Denes et al. "12-Crown-4—Ether and Tri(ethylene glycol) Dimethyl—Ether Plasma-Coated Stainless Steel Surfaces and Their Ability to Reduce Bacterial Biofilm Deposition" J. Appl. Polym. Sci. 2001, 81, 3425-3438.

Dong et al. "Generation of Antifouling Layers on Stainless Steel Surfaces by Plasma-Enhanced Crosslinking of Polyethylene Glycol" J. Appl. Polym. Sci., 2005, 97, 485-497.

Hara et al. "Role of stent design and coatings on restenosis and thrombosis" Adv. Drug Del. Rev. 2006, 58, 377-388.

Pesek et al. "Methods for the modification and characterization of oxide surfaces" Interface Science 1997, 5, 103-117.

Kim et al. "Surface modification for hydrophilic property of stainless steel treated by atmospheric-pressure plasma jet" Surface and Coatings Technology, 2003, 171, 312-316.

Suzuki et al. "Characterization of oxide films generated on stainless steel in water vapor and oxygen plasmas" Surface and Coatings Technology 2005, 200, 284-287.

Raman et al. "Self-assembled monolayers of alkanoic acids on the native oxide surface of SS316L by solution deposition" Langmuir, 2007, 23, 2284-2288.

Raman et al. "Formation of self-assembled monolayers of alkylphosphonic acid on the native oxide surface of SS316L" Langmuir, 2006, 22, 6469-6472.

Gao et al. "Self-assembled monolayers of alkylphosphonic acids on metal oxides" . Langmuir, 1996, 12, 6429-6435.

Hehrlein et al. "Drug-eluting stent: the magic bullet" for prevention of restenosis? Basic Res Cardiol. Nov. 2002;97 (6):417-23.

Costa et al. "Molecular basis of restenosis and drug-eluting stents" Circulation. May 3, 2005;111(17):2257-73.

Hanefeld et al. "Coating of poly(p-xylylene) by PLA-PEO-PLA triblock copolymers with excellent polymer-polymer adhesion for stent applications" Biomacromolecules. Jul. 2006;7(7):2086-90.

Machan et al. "Clinical experience and applications of drug-eluting stents in the noncoronary vasculature, bile duct and esophagus" Adv Drug Deliv Rev. Jun. 3, 2006;58(3):447-62.

Acharya et al. "Mechanisms of controlled drug release from drug-eluting stents" Adv Drug Deliv Rev. Jun. 3, 2006;58(3):387-401.

Presbitero P. et al., "Drug eluting stents do they make the difference?", Minerva Cardioangiol, 2002, 50 (5):431-442.

Ruygrok P.N. et al., "Rapamycin in cardiovascular medicine", Intern. Med. J., 2003, 33(3):103-109.

Marx S.O. et al., "Bench to bedside: the development of rapamycin and its application to stent restenosis", Circulation, 2001, 104(8):852-855).

Office Action dated Feb. 17, 2009 for copending U.S. Appl. No. 11/325,020 published as US 20060172914.

* cited by examiner

COVALENT MODIFICATION OF METAL SURFACES

CROSS-REFERENCE TO RELATED APPLICATIONS

This application claims priority to U.S. provisional patent application Ser. No. 60/819,200, filed Jul. 7, 2006, the entirety of which is hereby incorporated herein by reference.

BACKGROUND OF THE INVENTION

Modification of inorganic substrates with polymeric materials has been utilized in a range of applications across numerous scientific disciplines including analytical chemistry, biology, and electronics. (Mansky, P., et. al. *Science* 1997, 275, 1458-1460; Huang, Z. *Langmuir,* 1997, 13, 6480-6484. Granick, S. et. al. J. Polym. Sci. B. 2003, 41, 2755-2793.) Inorganic substrates can be coated with polymers or other molecules using a number of currently available methods. One popular, simple method involves the physical adsorbtion of a polymer to a substrate through coating or other deposition techniques. Other methods utilize covalent or ionic bonding between functionality on a polymer, or small molecule, and functionality present on the substrate surface to achieve modification. (Denes, A. R. et. al. *J. Appl. Polym. Sci.* 2001, 81, 3425-3438). While simple adsorption of polymers to metal substrates has proven successful in many cases, this procedure does not produce mechanically robust coatings with long-term stability. Post-adsorption crosslinking (Dong, B. et. al.; *J. Appl. Polym. Sci.,* 2005, 97, 485-497.) of the polymer coating may increase the toughness and short-term performance of the resulting film, but such crosslinking can also result in cracking and flaking of the polymer films over time, resulting in mechanical failure and a dramatic reduction in film properties. The chemical attachment of functional polymers to a metal substrate introduces a stable, robust linkage between polymer chains and the metal substrate and represents a more desirable scenario for many applications where the long-term stability of the coating is required for optimal performance. (Hara, H. et. al. *Adv. Drug Del. Rev.* 2006, 58, 377-388.) However, the methodologies to prepare covalent attachment of polymers to metallic and non-metallic substrates has thus far been limited to only a few examples of suitable substrates and complimentary chemical functionalities. Such examples include the near-covalent interaction between gold substrates and thiol-functionalized molecules, covalent bonds formed between silica and alcohol, silyl chloride, or silyl alcohol-functionalized compounds, and covalent bonds formed between hydrogen-functionalized silicon surfaces and alkene-substituted molecules. (Mansky, P., et. al *Science* 1997, 275, 1458-1460, Pesek, J. J.; Matyska, M. T. *Interface Science* 1997, 5, 103-117.)

Accordingly, it would be advantageous to provide a method of modifying metal surfaces to provide a metal substrate capable of forming covalent bonds with appropriately functionalized polymers or small molecule derivatives.

DETAILED DESCRIPTION OF CERTAIN EMBODIMENTS OF THE INVENTION

1. General Description of the Invention

Figure 1:
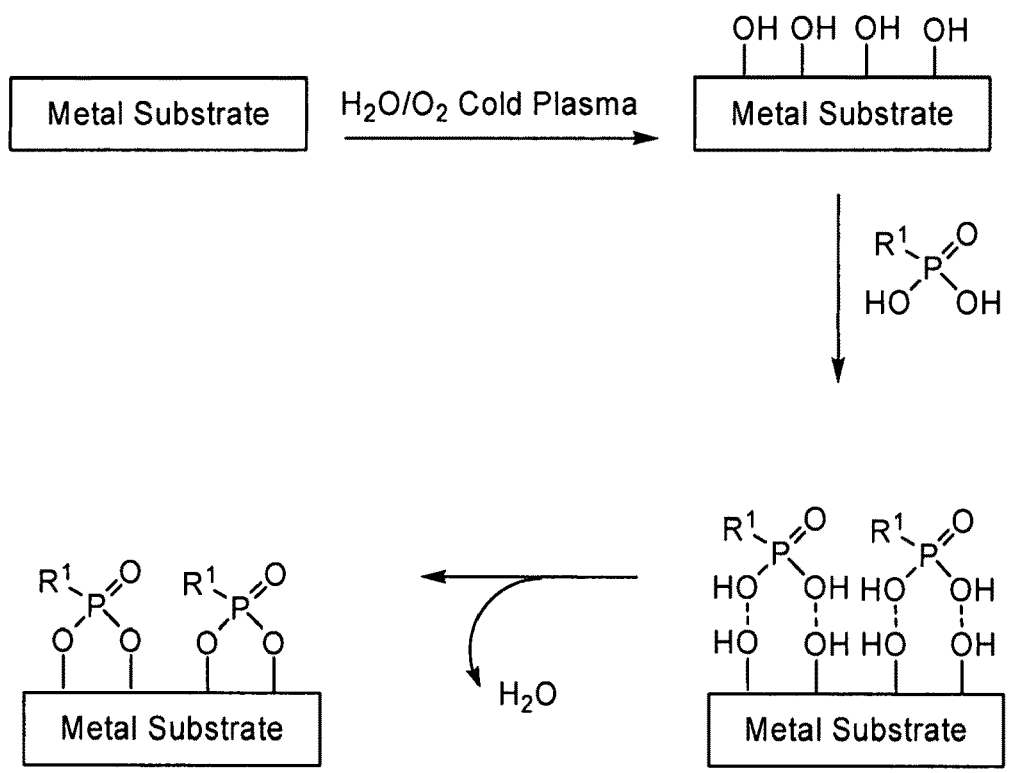
FIG. 1 depicts a method for covalently modifying a metal surface via dehydration reaction.

The present invention provides methods for covalently modifying a metal surface with a polymeric group or a small molecule organic moiety. In order to covalently bond the polymeric group or small molecule organic moiety to the metal surface, the metal surface is treated to introduce hydroxyl groups. In certain embodiments, the present invention provides a method for covalently modifying a metal surface, comprising the steps of introducing hydroxyl groups onto a metal substrate and covalently bonding a polymer or small molecule organic moiety onto the resulting hydrophilic metal surface.

2. Definitions

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As used herein, the term "sequential polymerization", and variations thereof, refers to the method where after a first monomer (e.g. NCA or lactam) is incorporated into the polymer, thus forming a "block", a second monomer (e.g. NCA or lactam) is added to the reaction and the polymerization continues in a similar fashion resulting in the formation of multi-block copolymers.

As used herein, the term "block copolymer" refers to a polymer comprising two or more polymer portions. The term "multi-block copolymer" refers to a polymer comprising at least three separate polymer portions. These are also referred to as triblock copolymers, tetrablock copolymers, etc. Such multi-block copolymers may be of the format X—W—X', W—X—X', W—X—X'—X" or X'—X—W—X—X', wherein W is a certain synthetic polymer portion and X, X', and X" are differing polymer chains. In certain aspects, the synthetic polymer is used as the center block which allows the growth of multiple blocks symmetrically from center.

As used herein, the term "synthetic polymer" refers to a polymer that is well known in the art and includes polystryrene, polyalkylene oxides, polyacrylates, polyacrylamides, polyamines, polyolefins, and derivatives thereof.

As used herein, the term "natural polymer" refers to a polymer that is well known in the art and includes polysaccarides, dextran, heparin, fibronectin, poly(amino acids), starch, amylose, amylopectin, polypeptides, proteins, and derivatives thereof.

As used herein, the term "polymer" may refer to either a natural polymer or synthetic polymer.

As used herein, the term "poly(amino acid)" or "amino acid block" refers to a covalently linked amino acid chain wherein each monomer is an amino acid unit. Such amino acid units include natural and unnatural amino acids. In certain embodiments, each amino acid unit is in the L-configuration. Such poly(amino acids) include those having suitably protected functional groups. For example, amino acid monomers may have hydroxyl or amino moieties which are optionally protected by a suitable hydroxyl-protecting group or a suitable amine protecting group, as appropriate. Such suitable hydroxyl-protecting groups and suitable amine protecting groups are described in more detail herein, infra. As used herein, an amino acid block comprises one or more monomers or a set of two or more monomers. In certain embodiments, an amino acid block comprises one or more monomers such that the overall block is hydrophilic. In other embodiments, an amino acid block comprises one or more monomers such that the overall block is hydrophobic. In still other embodiments, amino acid blocks of the present invention include random amino acid blocks, i.e. blocks comprising a mixture of amino acid residues.

As used herein, the phrase "natural amino acid side-chain group" refers to the side-chain group of any of the 20 amino acids naturally occurring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyroine nonpolar and hydrophobic by virtue of protecting the hydroxyl group.

As used herein, the phrase "unnatural amino acid side-chain group" refers to amino acids not included in the list of 20 amino acids naturally occurring in proteins, as described above. Such amino acids include the D-isomer of any of the 20 naturally occurring amino acids. Unnatural amino acids also include homoserine, ornithine, and thyroxine. Other unnatural amino acids side-chains are well know to one of ordinary skill in the art and include unnatural aliphatic side chains. Other unnatural amino acids include modified amino acids, including those that are N-alkylated, cyclized, phosphorylated, acetylated, amidated, azidylated, labelled, and the like.

As used herein, the phrase "living polymer chain-end" refers to the terminus resulting from a polymerization reaction having maintained chain-end reactivity after the completion of the reaction.

As used herein, the term "termination" refers to attaching a terminal group to a polymer chain-end by the reaction of a living polymer with an appropriate compound. Alternatively, the term "termination" may refer to attaching a terminal group to a hydroxyl end, or derivative thereof, of the polymer chain.

As used herein, the term "polymerization terminator" is used interchangeably with the term "polymerization terminating agent" and refers to a compound for attaching a terminal group to a polymer chain-end of a living polymer. Alternatively, the term "polymerization terminator" may refer to a compound for attaching a terminal group to a hydroxyl end, or derivative thereof, of the polymer chain.

As used herein, the term "polymerization initiator" refers to a compound, or anion thereof, which reacts with the desired monomer in a manner which results in polymerization of that monomer. In certain embodiments, the polymerization initiator is the anion of a functional group which initiates the polymerization of ethylene oxide. In other embodiments, the polymerization initiator is the amine salt described herein.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heterocycle", "heterocyclyl", "heterocycloaliphatic", or "heterocyclic" as used herein means nonaromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; $N_3$, CN, $R^o$; $OR^o$; $SR^o$; 1,2-methylene-dioxy; 1,2-ethylenedioxy; phenyl (Ph) optionally substituted with $R^o$; —O(Ph) optionally substituted with $R^o$; $(CH_2)_{1-2}$(Ph), optionally substituted with $R^o$; CH=CH(Ph), optionally substituted with $R^o$; $NO_2$; CN; $N(R^o)_2$; $NR^oC(O)R^o$; $NR^oC(O)N(R^o)_2$; $NR^oCO_2R^o$; —$NR^oNR^oC(O)R^o$; $NR^oNR^oC(O)N(R^o)_2$; $NR^oNR^oCO_2R^o$; $C(O)C(O)R^o$; $C(O)CH_2C(O)R^o$; $CO_2R^o$; $C(O)R^o$; $C(O)N(R^o)_2$; $OC(O)N(R^o)_2$; $S(O)_2R^o$; $SO_2N(R^o)_2$; $S(O)R^o$; $NR^oSO_2N(R^o)_2$; $NR^oSO_2R^o$; $C(=S)N(R^o)_2$; $C(=NH)$—$N(R^o)_2$; or $(CH_2)_{0-2}NHC(O)R^o$ wherein each independent occurrence of $R^o$ is selected from hydrogen, optionally substituted $C_{1-6}$ aliphatic, an unsubstituted 5-6 membered heteroaryl or heterocyclic ring, phenyl, O(Ph), or $CH_2$(Ph), or, notwithstanding the definition above, two independent occurrences of $R^o$, on the same substituent or different substituents, taken together with the atom(s) to which each $R^o$ group is bound, form a 3-8 membered cycloalkyl, heterocyclyl, aryl, or heteroaryl ring having 0-4 heteroatoms independently selected from nitrogen, oxygen, or sulfur. Optional substituents on the aliphatic group of $R^o$ are selected from $N_3$, CN, $NH_2$, $NH(C_{1-4}$aliphatic), $N(C_{1-4}$aliphatic)$_2$, halogen, $C_{1-4}$aliphatic, OH, $O(C_{1-4}$aliphatic), $NO_2$, CN, $CO_2H$, $CO_2(C_{1-4}$aliphatic), $O(haloC_{1-4}$ aliphatic), or $haloC_{1-4}$aliphatic, wherein each of the foregoing $C_{1-4}$aliphatic groups of $R^o$ is unsubstituted.

An aliphatic or heteroaliphatic group or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), $O(halo\ C_{1-4}$ aliphatic), or $halo(C_{1-4}$ aliphatic), wherein each of the foregoing $C_{1-4}$aliphatic groups of R* is unsubstituted.

Optional substituents on the nitrogen of a non-aromatic heterocyclic ring are selected from $R^+$, $N(R^+)_2$, $C(O)R^+$, $CO_2R^+$, $C(O)C(O)R^+$, $C(O)CH_2C(O)R^+$, $SO_2R^+$, $SO_2N(R^+)_2$, $C(=S)N(R^+)_2$, $C(=NH)$—$N(R^+)_2$, or $NR^+SO_2R^+$; wherein $R^+$ is hydrogen, an optionally substituted $C_{1-6}$ aliphatic, optionally substituted phenyl, optionally substituted O(Ph), optionally substituted $CH_2$(Ph), optionally substituted $(CH_2)_{1-2}$(Ph); optionally substituted CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 3-8-membered cycloalkyl, heterocyclyl, aryl, or heteroaryl ring having 0-4 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), $O(halo\ C_{1-4}$ aliphatic), or $halo(C_{1-4}$ aliphatic), wherein each of the foregoing $C_{1-4}$aliphatic groups of $R^+$ is unsubstituted.

As detailed above, in some embodiments, two independent occurrences of $R^o$ (or $R^+$, or any other variable similarly defined herein), are taken together with the atom(s) to which each variable is bound to form a 3-8-membered cycloalkyl, heterocyclyl, aryl, or heteroaryl ring having 0-4 heteroatoms independently selected from nitrogen, oxygen, or sulfur. Exemplary rings that are formed when two independent occurrences of $R^o$ (or $R^+$, or any other variable similarly defined herein) are taken together with the atom(s) to which each variable is bound include, but are not limited to the following: a) two independent occurrences of $R^o$ (or $R^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

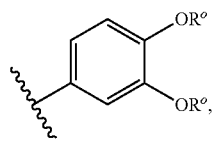

these two occurrences of R° are taken together with the oxygen atoms to which they are bound to form a fused 6-membered oxygen containing ring:

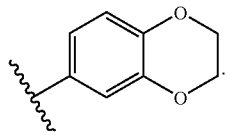

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

As used herein, the term "detectable moiety" is used interchangeably with the term "label" and relates to any moiety capable of being detected, e.g., primary labels and secondary labels. Primary labels, such as radioisotopes (e.g., $^{32}$P, $^{33}$P, $^{35}$S, or $^{14}$C), mass-tags, and fluorescent labels are signal generating reporter groups which can be detected without further modifications.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethylrhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The term "metal substrate", as used herein refers to any metallic material which may be modified to incorporate hydroxyl groups to which a functionalized end-group of a polymeric or small molecule organic group can be attached.

3. Description of Exemplary Embodiments

As described generally above, the present invention provides a method for covalently modifying a metal substrate, comprising the steps of introducing hydroxyl groups onto the metal substrate to produce a hydrophilic metal surface and covalently bonding a polymer or small molecule organic moiety onto the hydrophilic metal surface. As used herein, the phrase "hydrophilic metal surface" refers to a metal substrate onto which a plurality of hydroxyl groups has been incorporated. One of ordinary skill in the art would recognize that various metallic substrates are amenable to methods of the present invention. In certain embodiments, the metal substrate is any such substrate that comprises iron. In other embodiments, the metal substrate comprises a stainless steel, a cobalt alloy, or a titanium alloy. In still other embodiments, the metal substrate comprises iron, iron alloys, steel, stainless steel, austenitic stainless steel, Type 316 stainless steel, ferritic stainless steel, martensitic stainless steel, duplex stainless steel, cobalt, cobalt alloys, cobalt-chromium alloys, stellite alloys, Vitallium®, titanium, titanium alloys, nickel-titanium alloys, nitinol, or super-alloys.

Hydrophilic metal surfaces can be prepared with the use of oxygen and/or water plasmas. (Kim et. al. *Surface and Coatings Technology*, 2003, 171, 312-316). It has been shown that hydroxyl groups, in the form of Fe(OH)$_2$, are the source of this hydrophilicity on the metal surface. (Suzuki et. al. *Surface and Coatings Technology* 2005, 200, 284-287). This strategy extends to a number of iron-based metals and alloys such as iron, iron alloys, steel, stainless steel, austenitic stainless steel, Type 316 stainless steel, ferritic stainless steel, martensitic stainless steel, and duplex stainless steel. Other suitable metal substrates include cobalt, cobalt alloys, cobalt-chromium alloys, stellite alloys, Vitallium®, titanium, titanium alloys, nickel-titanium alloys, nitinol, and super-alloys. The geometry of the metal substrate includes, but is not limited to, flat surfaces, curved surfaces, cylinders, spheres, wire mesh, and tubing.

Using chemical functionality on the surface of plasma-treated metals, it would be advantageous to perform additional chemical modification of the substrate through dehydration or condensation reactions. Such reactions proceed on the hydrophilic metal surface without the need for additional reagents or catalysts. Chemical functionalities that undergo dehydration reactions with the plasma-modified metal substrates include, but are not limited to, phosphonic acids, silyl-alcohols and carboxylic acids. (Raman, A.; Gawalt, E. S. *Langmuir*, 2007, 23, 2284-2288. Raman, A. et. al. *Langmuir*, 2006, 22, 6469-6472. Gao, W. et. al. *Langmuir*, 1996, 12, 6429-6435.) In addition, phosphonic halides, acyl halides, and silyl-halides can undergo condensation reactions with hydroxyl functionalized metal surfaces to afford the desired modified metallic material.

In certain embodiments, the dehydration reaction is carried out by first incubating the hydrophilic metal surface with the suitable functional molecule in an aqueous or organic solution. Without wishing to be bound by any particular theory, it is believed that during incubation, hydrogen bonding promotes the interaction of the functional molecule with the modified metal surface. This hydrogen-bonded intermediate is then converted to a covalent bond by subsequent dehydration. In certain embodiments, the dehydration step is performed at reduced pressure and/or elevated temperature. In other embodiments, the condensation reaction of acid-halide or silyl halide functional molecules and hydroxyl-functionalized metal substrates is performed using anhydrous conditions in dry organic solvents, leading directly to the desired covalently modified metal surface. One of ordinary still in the art will appreciate that the covalent bond forming reactions contemplated by the present invention are not limited to dehydration and condensation reactions and include, for example, addition reactions.

The introduction of hydroxyl groups onto a metal surface is well known to one of ordinary skill in the art. One of ordinary skill would recognize that there are multiple methods for accomplishing the functionalization of a metal substrate. One such method is the oxidation of iron atoms found in metal substrates. Such oxidation is well known in the art and includes cold plasma methods as described by, e.g., Suzuki, et al, *Surface & Coatings Technology*, (2005) 284-287. In certain embodiments, the metal substrate is oxidized with water vapor plasma.

As described generally above, the functionalized metal surface is covalently bonded to a polymer or a small molecule organic moiety. One of ordinary skill in the art would appreciate that hydroxyl groups are covalently bonded to a variety of other functional groups (e.g., with carboxylic acids to form esters thereof) by condensation or dehydration reaction. All such functional groups capable of covalently bonding to the hydroxyl groups incorporated onto the metal surface are contemplated. In certain embodiments, the polymer or small molecule organic moiety comprises one or more functional groups capable of covalently bonding to one or more hydroxyl groups incorporated onto the metal surface. Exemplary functional groups include, but are not limited to, phosphonic acids, silyl-alcohols, carboxylic acids, phosphonic halides, acyl halides, and silyl-halides.

Polymeric groups for use in the present invention comprise one or more functional groups capable of covalently bonding with one or more hydroxyl groups incorporated onto the metal surface. It will be appreciated that many such polymeric groups are amenable to this reaction. These polymeric groups include natural or synthetic polymers and copolymers. Exemplary polymers include mono-functionalized PEG's, poly(amino acids), heterobifunctional PEG's, branched PEG's, heterofunctionalized branched PEG's, PEG-b-PAA-b-PAA block copolymer, PEG-b-PAA-b-PEG block copolymers, PEG-b-polyester-b-PEG block copolymers, PEG-b-PAA block copolymers, [where PAA refers to poly(amino acid)], dextran, heparin, fibronectin, chitosan, amylose, amylopectin, glycogen, xanthan, gellan, pullulun, cellulose, and cellulose acetate.

In certain embodiments, the present invention provides a method for preparing a covalently modified metal surface, comprising the steps of:

(a) modifying a metal substrate to incorporate thereon a plurality of hydroxyl groups;

(b) providing a compound of formula I:

$$R^1\text{—}W \qquad\qquad\qquad \text{I}$$

wherein:

$R^1$ is a natural or synthetic polymer or copolymer group or a small molecule organic group;

W is —C(=O)OH, —C(=O)X, —P(=O)(OH)$_2$, —P(=O)(X)$_2$, —P(=O)(R$^a$)OH, —P(=O)(R$^a$)X, —O—S(=O)$_2$OH, —S(=O)$_2$OH, —Si(R$^a$)$_2$OH, —Si(OR$^a$)$_2$OH, —Si(R$^a$)$_2$X, —Si(R$^a$)(OH)$_2$, —Si(R$^a$)X$_2$, —Si(OR$^a$)$_2$X, C(=O)H, —N=C=S, —N=C=O, phenol, thiophenol, or an epoxide;

each X is independently Cl, Br, or I; and each R$^a$ is hydrogen, an alkyl group, or an aryl group; and (c) coupling the compound of formula I to one or more of the hydroxyl groups on the metal surface.

As described generally above, the coupling step (c) can be performed in the absence of reagents or catalysts by dehydration or condensation. However, it is also contemplated that the coupling step (c) can be performed in the presence of such reagents or catalysts. For example, coupling step (c) may be performed in the presence of a suitable base. Suitable bases include any of those known to one of ordinary skill in the art for such coupling reactions. Exemplary bases include, but are not limited to, triethylamine, diisopropylamine, diisopropylethylamine, dimethylaminopyridine, and the like.

Figure 2:
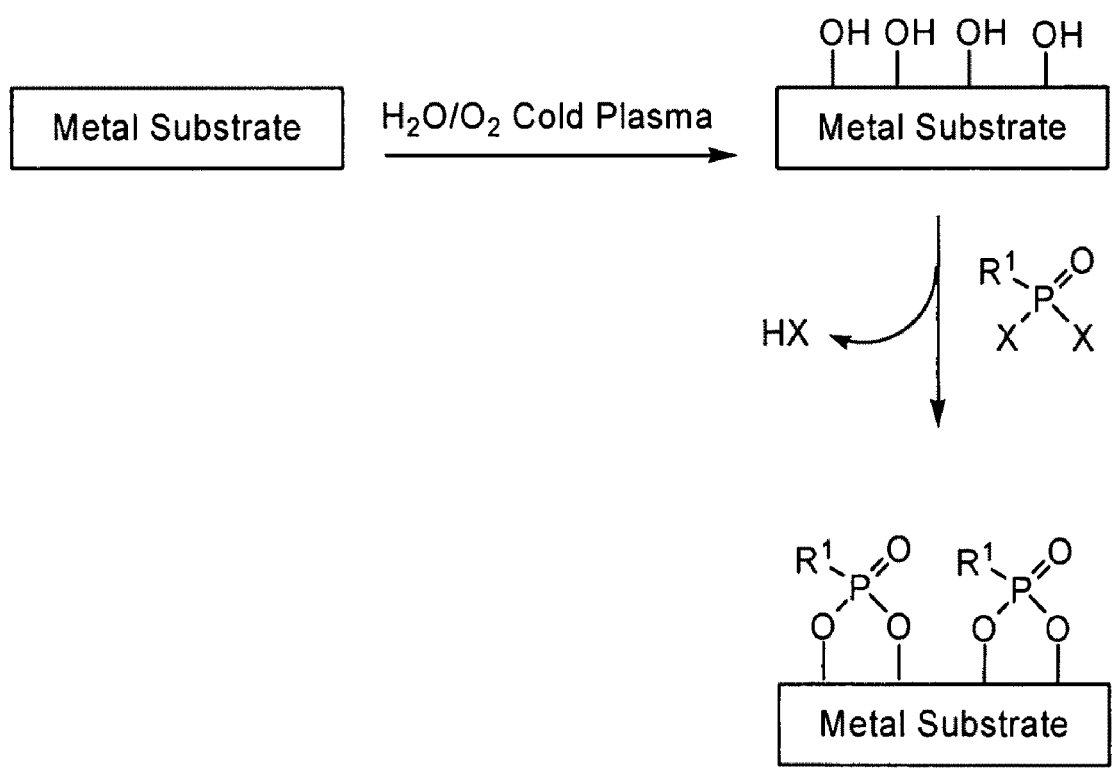
FIG. 2 depicts a method for covalently modifying a metal surface via condensation reaction.
Figure 4:
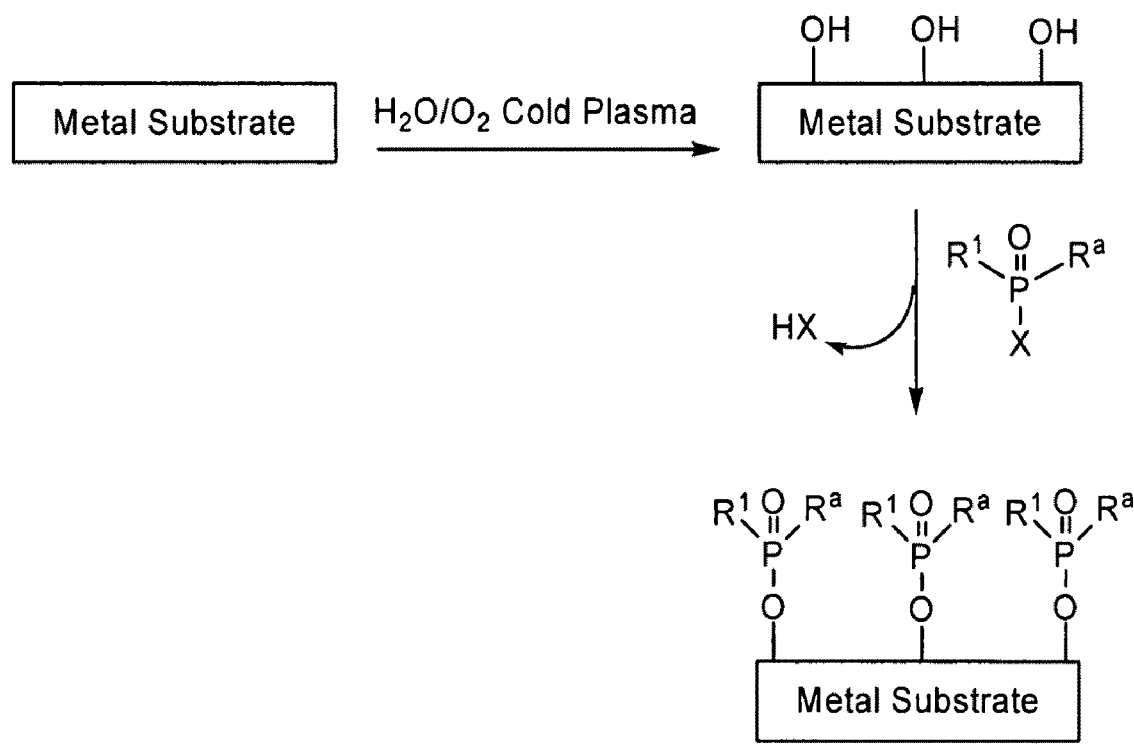
FIG. 4 depicts a method for covalently modifying a metal surface via condensation reaction.
Figure 6:
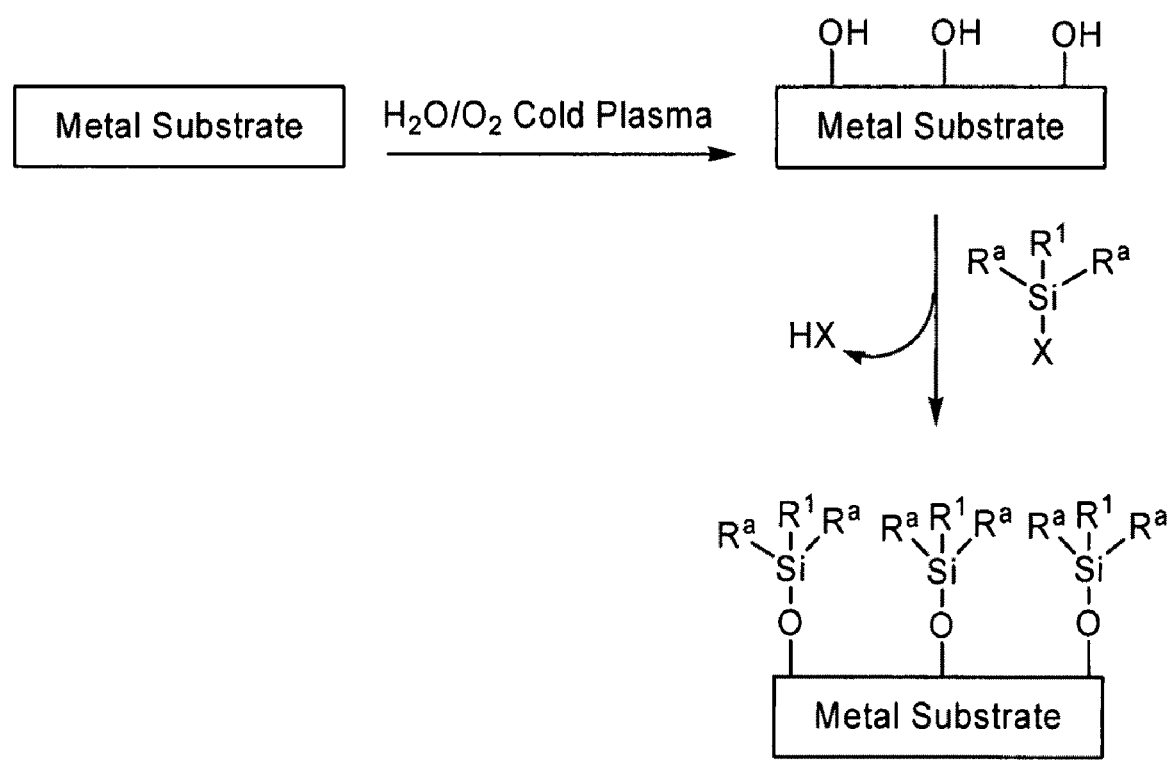
FIG. 6 depicts a method for covalently modifying a metal surface via condensation reaction.
Figure 8:
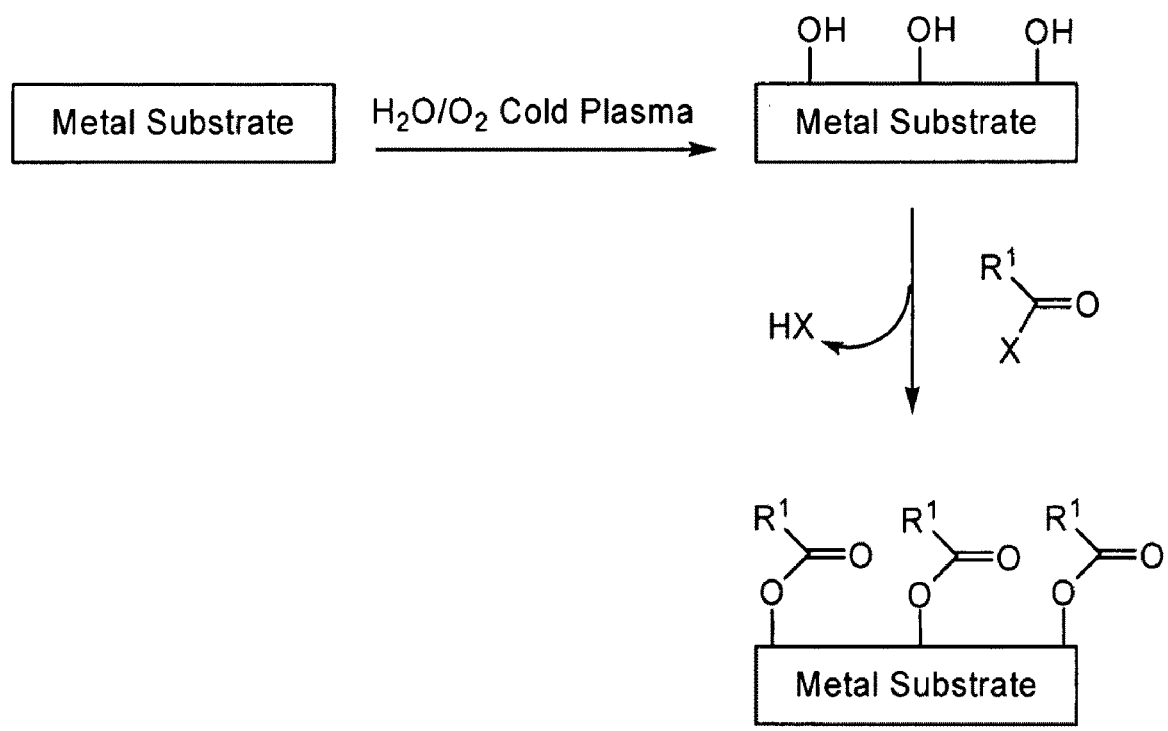
FIG. 8 depicts a method for covalently modifying a metal surface via condensation reaction.
Figure 10:
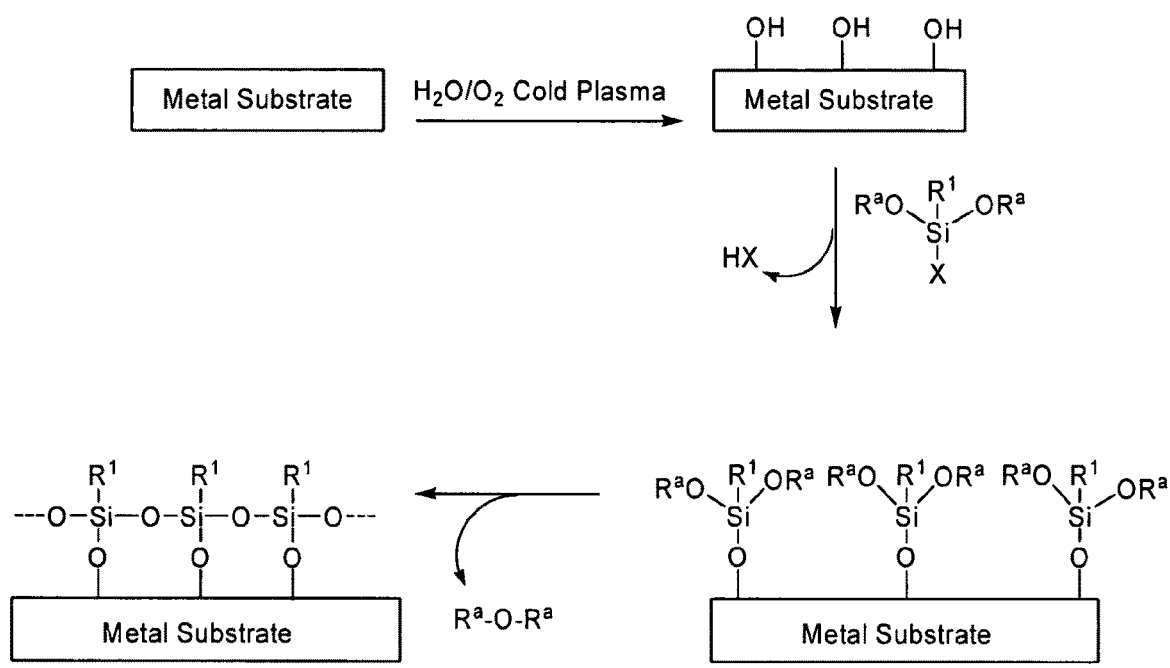
FIG. 10 depicts a method for covalently modifying a metal surface via condensation reaction followed by crosslinking.
Figure 12:
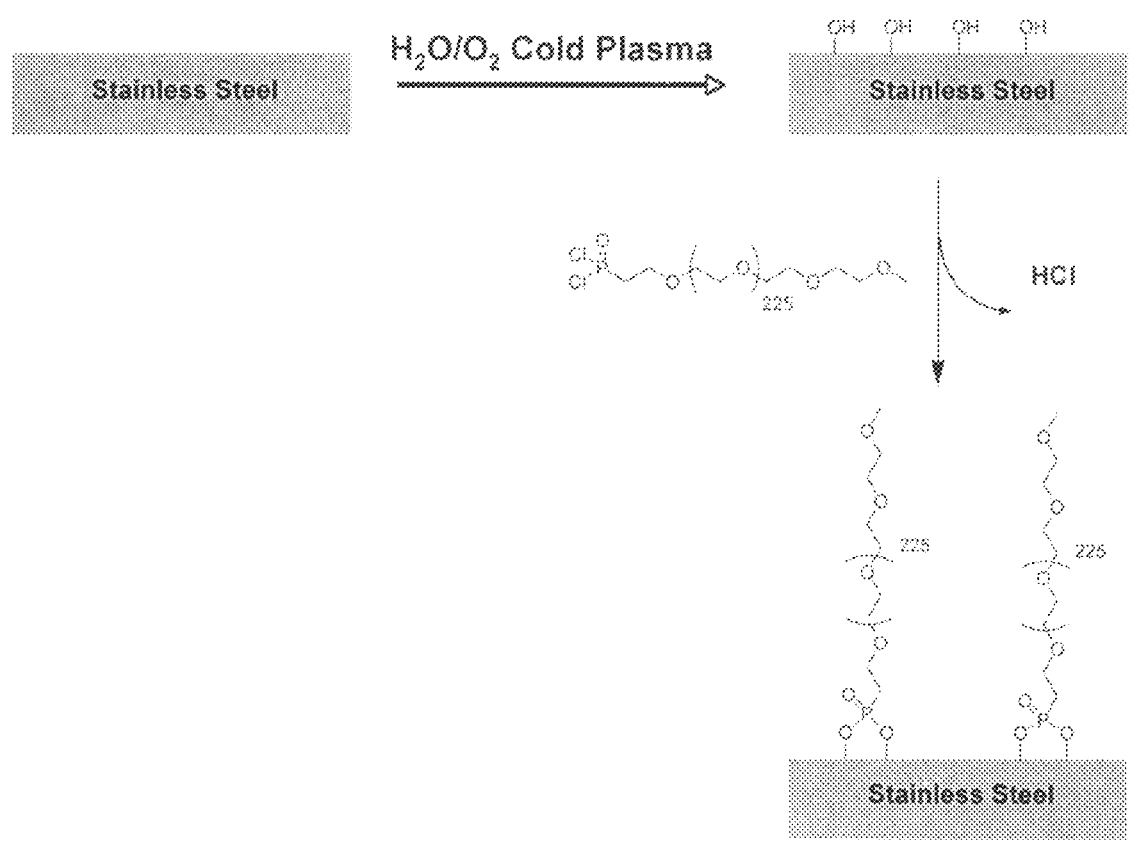
FIG. 12 depicts a method for PEGylating a metal surface via condensation reaction.

One of ordinary skill in the art will appreciate that when W is —C(=O)X, —P(=O)(X)$_2$, —P(=O)(R$^a$)X, —Si(R$^a$)$_2$X, or —Si(OR$^a$)$_2$X, then the coupling at step (c) can occur by a condensation reaction. See FIGS. 2, 4, 6, 8, 10, and 12 which depict representative methods of the present invention whereby coupling step (c) occurs by condensation reaction.

Figure 3:
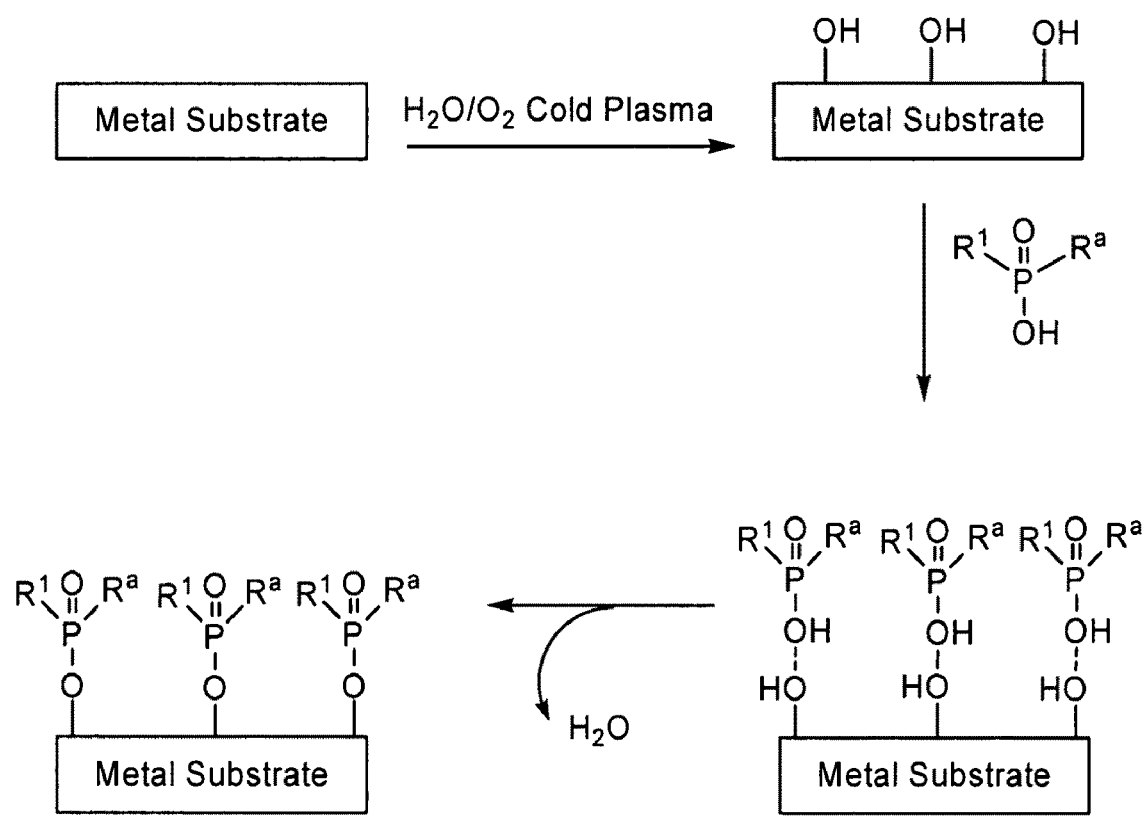
FIG. 3 depicts a method for covalently modifying a metal surface via dehydration reaction.
Figure 5:
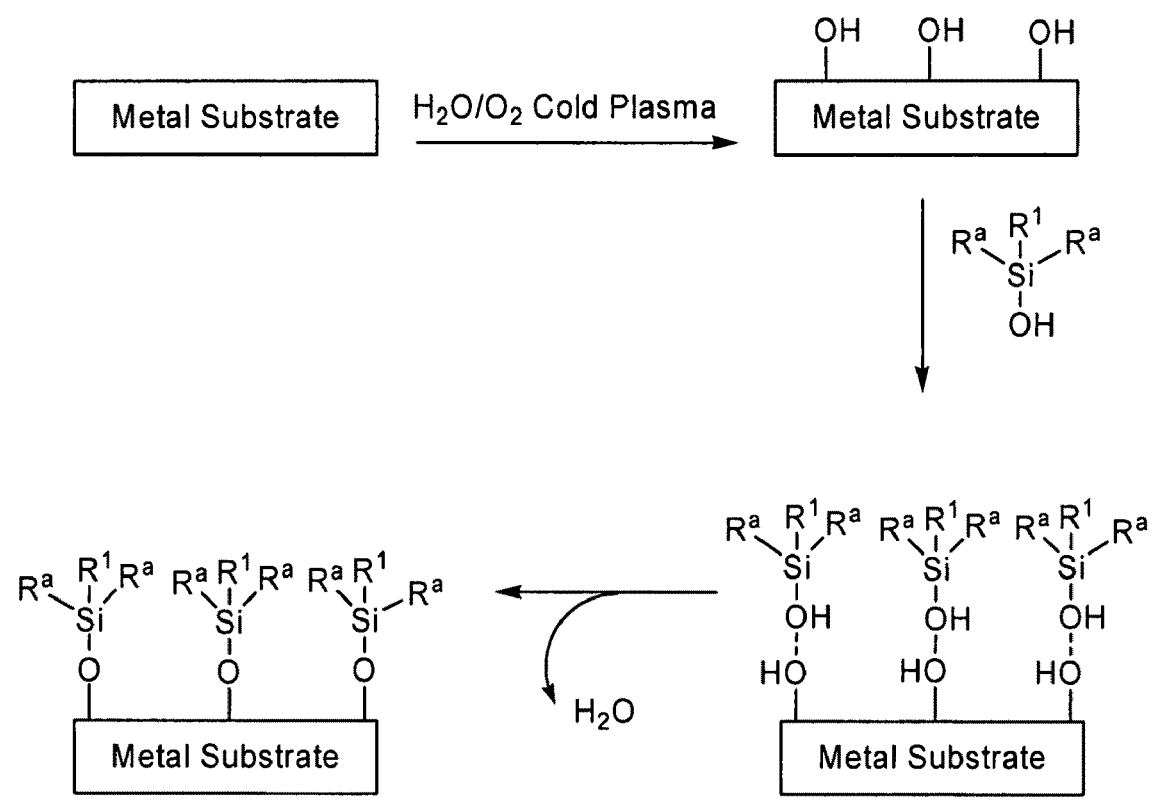
FIG. 5 depicts a method for covalently modifying a metal surface via dehydration reaction.
Figure 7:
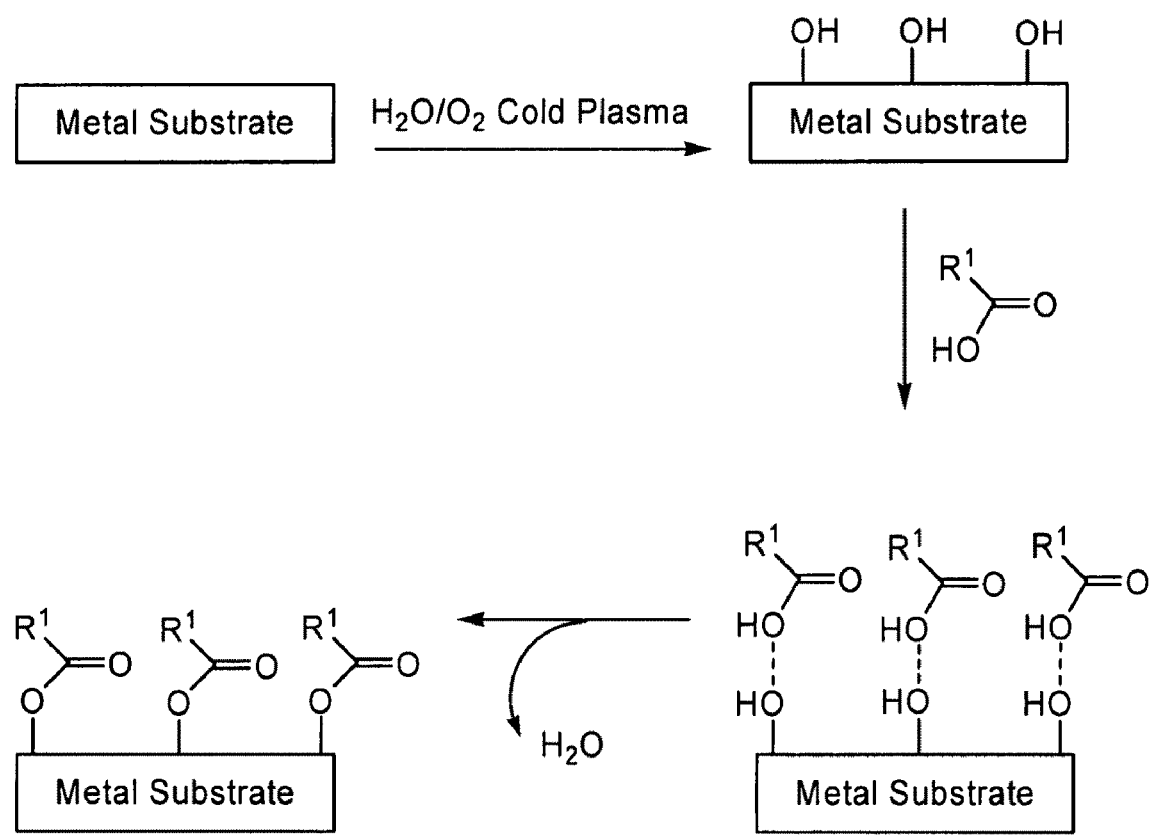
FIG. 7 depicts a method for covalently modifying a metal surface via dehydration reaction.
Figure 9:
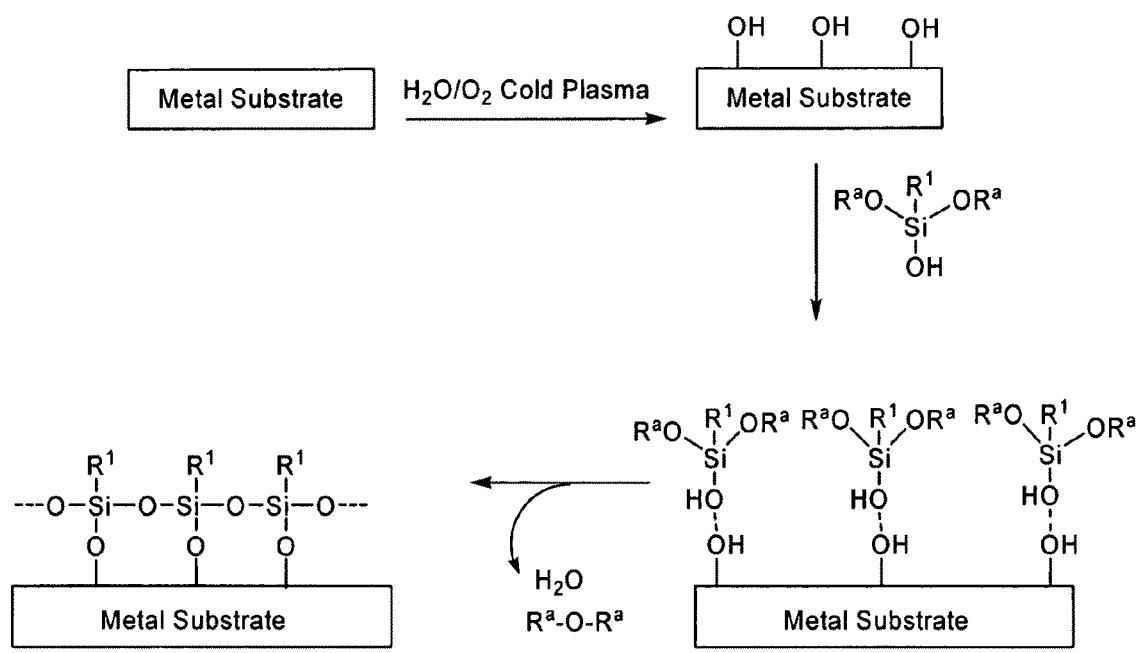
FIG. 9 depicts a method for covalently modifying a metal surface and crosslinking via dehydration reaction.
Figure 11:
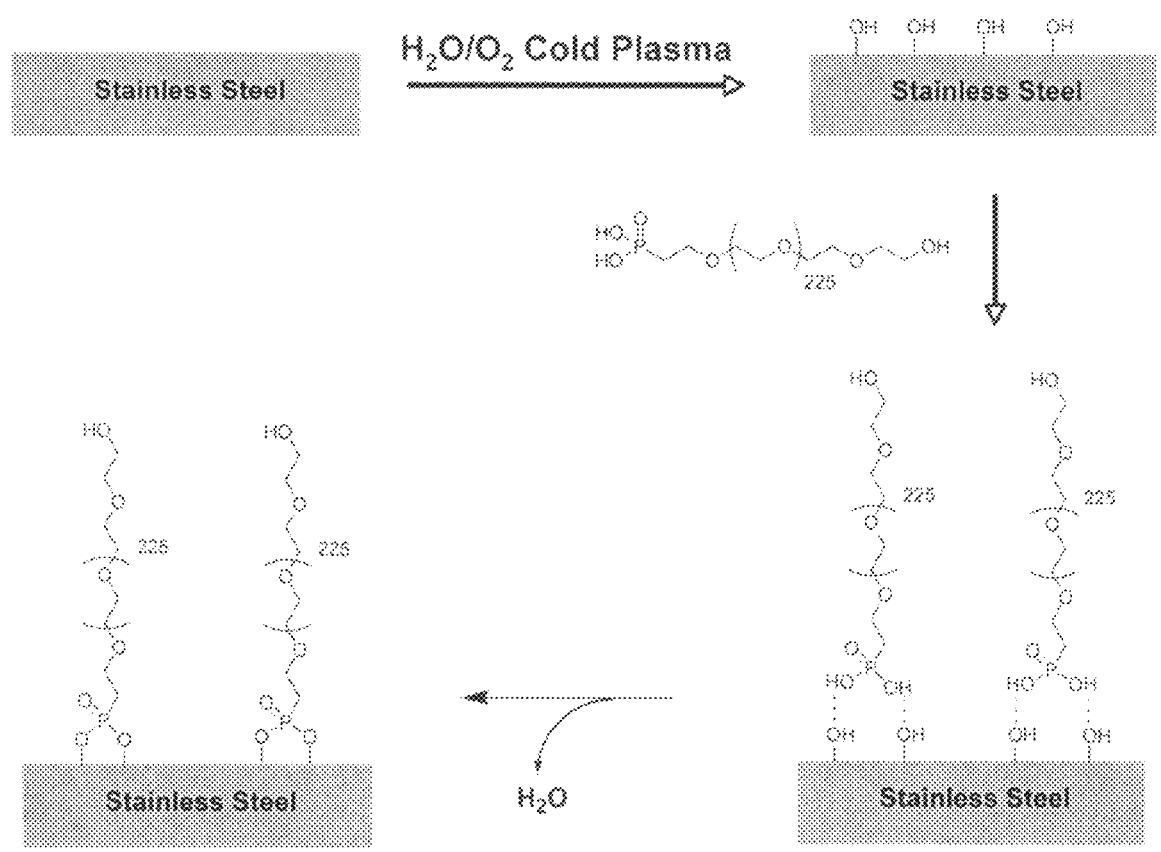
FIG. 11 depicts a method for PEGylating a metal surface via dehydration reaction.

Similarly, when W is —C(=O)OH, —P(=O)(OH)$_2$, —P(=O)(R$^a$)OH, —Si(R$^a$)$_2$OH, or —Si(OR$^a$)$_2$OH, the coupling at step (c) can occur by a dehydration reaction. See FIGS. 1, 3, 5, 7, 9, and 11 which depict representative methods of the present invention whereby coupling step (c) occurs by dehydration reaction.

In certain embodiments, the metal substrate comprises iron, iron alloys, steel, stainless steel, austenitic stainless steel, Type 316 stainless steel, ferritic stainless steel, martensitic stainless steel, duplex stainless steel, cobalt, cobalt alloys, cobalt-chromium alloys, stellite alloys, Vitallium®, titanium, titanium alloys, nickel-titanium alloys, nitinol, or super-alloys.

In other embodiments, R$^1$ is a synthetic polymer such as linear homopolymers, branched homopolymers, block copolymers, branched block copolymers, star polymers, star copolymers, graft copolymers, hyperbranched copolymers, and dendrimers. In still other embodiments, R$^1$ is a natural polymer such as oligopeptides, proteins, polynucleic acids (e.g. DNA and RNA), oligosaccharides, and polysaccharides. According to another aspect of the present invention, R$^1$ is poly(ethylene glycol) (PEG), a heterobifunctional PEG, a branched PEG, heterofunctionalized branched PEG's, PEG-b-PAA-b-PAA block copolymer, PEG-b-PAA-b-PEG block copolymers, PEG-b-polyester-b-PEG block copolymers, PEG-b-PAA block copolymers, [where PAA refers to poly (amino acid)], dextran, heparin, fibronectin, chitosan, amylose, amylopectin, glycogen, xanthan, gellan, pullulun, cellulose, and cellulose acetate.

In certain embodiments, R$^1$ is a small molecule organic group. In other embodiments, R$^1$ is selected from monosaccharides (e.g., glucose, galactose, fructose) and disaccharides (e.g., sucrose, lactose, maltose), phosphorylcholines, phosoplipids, cyclodextrans, and small molecule drugs.

In other embodiments, the present invention provides a method for preparing a covalently modified metal surface, comprising the steps of:
(a) providing a metal surface having a plurality of hydroxyl groups;
(b) providing a compound of formula I:

$$R^1-W \qquad I$$

wherein:
R$^1$ is a natural or synthetic polymer or copolymer group or a small molecule organic group;
W is —C(=O)OH, —C(=O)X, —P(=O)(OH)$_2$, —P(=O)(X)$_2$, —P(=O)(R$^a$)OH, —P(=O)(R$^a$)X, —O—S(=O)$_2$OH, —S(=O)$_2$OH, —Si(R$^a$)$_2$OH, —Si(OR$^a$)$_2$OH, —Si(R$^a$)$_2$X, —Si(R$^a$)(OH)$_2$, —Si(R$^a$)X$_2$, —Si(OR$^a$)$_2$X, C(=O)H, —N=C=S, —N=C=O, phenol, thiophenol, or an epoxide;
each X is independently Cl, Br, or I; and
each R$^a$ is hydrogen, an alkyl group, or an aryl group; and
(c) coupling the compound of formula I to one or more of the hydroxyl groups on the metal surface.

Polymer Groups

As defined generally above, R$^1$ is a natural or synthetic polymer or copolymer group or a small molecule organic group. In certain embodiments, R$^1$ is a poly(alkylene oxide) group or a branched poly(alkylene oxide). In other embodiments, R$^1$ is a poly(ethylene glycol) group ("PEG"). PEG's are well known to one of ordinary skill in the art and include those described in detail in International Patent Application publication number WO2006/047419, U.S. Provisional Patent Application Ser. No. 60/795,412, filed Apr. 27, 2006, and U.S. Provisional Patent Application Ser. No. 60/795,374, filed Apr. 27, 2006, the entirety of each of which is hereby incorporated herein by reference. According to another aspect of the present invention, R$^1$ is a group of formula II:

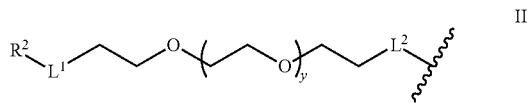

or a salt thereof, wherein:
y is 0-2500;
R$^2$ is hydrogen, halogen, NO$_2$, CN, N$_3$, —N=C=O, —C(R) =NN(R)$_2$, —P(O)(OR)$_2$, —P(O)(X')$_2$, a small molecule drug, a 9-30 membered crown ether, a mono-protected amine, a di-protected amine, a protected aldehyde, a protected hydroxyl, a protected carboxylic acid, a protected thiol, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
each X' is independently halogen;
each R is independently hydrogen or an optionally substituted aliphatic group;
L$^1$ is a valence bond or a bivalent, saturated or unsaturated, straight or branched C$_{1-12}$ alkylene chain, wherein 0-6 methylene units of L$^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and
L$^2$ is a valence bond or a bivalent, saturated or unsaturated, straight or branched C$_{1-12}$ alkylene chain, wherein 0-6 methylene units of L$^2$ are independently replaced by -Cy-, —O—, —NR—, —S—, or —C(O)—, wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

As defined generally above, the y group of formula II is 0-2500. In certain embodiments, the y group of formula II is 0. In certain embodiments, the present invention provides compounds of formula II, as described above, wherein y is about 225. In other embodiments, y is about 10 to about 40. In other embodiments, y is about 40 to about 60. In still other embodiments, y is about 90 to about 150. In still other embodiments, y is about 200 to about 250. In other embodiments, y is about 300 to about 375. In other embodiments, y is about 400 to about 500. In still other embodiments, y is about 650 to about 750. In still other embodiments, y is about 1 to about 10.

In certain embodiments, $R^2$ is optionally substituted aliphatic. In other embodiments, $R^2$ is an unsubstituted aliphatic. In some embodiments, said $R^2$ moiety is an optionally substituted alkyl group. In other embodiments, said $R^2$ moiety is an optionally substituted alkynyl or alkenyl group. Such groups include methyl, t-butyl, 5-norbornene-2-yl, octane-5-yl, —C≡CH, —CH$_2$C≡CH, —CH$_2$CH$_2$C≡CH, and —CH$_2$CH$_2$CH$_2$C≡CH. When said $R^2$ moiety is a substituted aliphatic group, suitable substituents on $R^2$ include any of CN, N$_3$, NO$_2$, —CO$_2$H, —SH, —NH$_2$, —C(O)H, —NHC(O)R$^o$, —NHC(S)R$^o$, —NHC(O)NR$^o{}_2$, —NHC(S)NR$^o{}_2$, —NHC(O)OR$^o$, —NHNHC(O)R$^o$, —NHNHC(O)NR$^o{}_2$, —NHNHC(O)OR$^o$, —C(O)R$^o$, —C(S)R$^o$, —C(O)OR$^o$, —C(O)SR$^o$, —C(O)OSiR$^o{}_3$, —OC(O)R$^o$, SC(S)SR$^o$, —SC(O)R$^o$, —C(O)N(R$^o$)$_2$, —C(S)N(R$^o$)$_2$, —C(S)SR$^o$, —SC(S)SR$^o$, —OC(O)N(R$^o$)$_2$, —C(O)NHN(R$^o$)$_2$, —C(O)N(OR$^o$)R$^o$, —C(O)C(O)R$^o$, —C(O)CH$_2$C(O)R$^o$, —C(NOR$^o$)R$^o$, —SSR$^o$, —S(O)$_2$R$^o$, —S(O)$_2$OR$^o$, —OS(O)$_2$R$^o$, —S(O)$_2$N(R$^o$)$_2$, —S(O)R$^o$, —N(R$^o$)S(O)$_2$N(R$^o$)$_2$, —N(R$^o$)S(O)$_2$R$^o$, —N(OR$^o$)R$^o$, —C(NH)N(R$^o$)$_2$, —P(O)$_2$R$^o$, —P(O)(R$^o$)$_2$, —OP(O)(R$^o$)$_2$, or —OP(O)(OR$^o$)$_2$, wherein each R$^o$ is as defined herein.

In other embodiments, $R^2$ is an aliphatic group optionally substituted with any of Cl, Br, I, F, —NH$_2$, —OH, —SH, —CO$_2$H, —C(O)H, —C(O)(C$_{1-6}$ aliphatic), —NHC(O)(C$_{1-6}$ aliphatic), —NHC(O)NH$_2$, —NHC(O)NH(C$_{1-6}$ aliphatic), —NHC(S)NH—, —NHC(S)N(C$_{1-6}$ aliphatic)$_2$, —NHC(O)O(C$_{1-6}$ aliphatic), —NHNH$_2$, —NHNHC(O)(C$_{1-6}$ aliphatic), —NHNHC(O)NH$_2$, —NHNHC(O)NH(C$_{1-6}$ aliphatic), —NHNHC(O)O(C$_{1-6}$ aliphatic), —C(O)NH$_2$, —C(O)NH(C$_{1-6}$ aliphatic)$_2$, —C(O)NHNH$_2$, —C(S)N(C$_{1-6}$ aliphatic)$_2$, —OC(O)NH(C$_{1-6}$ aliphatic), —C(O)C(O)(C$_{1-6}$ aliphatic), —C(O)CH$_2$C(O)(C$_{1-6}$ aliphatic), —S(O)$_2$(C$_{1-6}$ aliphatic), —S(O)$_2$O(C$_{1-6}$ aliphatic), —OS(O)$_2$(C$_{1-6}$ aliphatic), —S(O)$_2$NH(C$_{1-6}$ aliphatic), —S(O)(C$_{1-6}$ aliphatic), —NHS(O)$_2$NH(C$_{1-6}$ aliphatic), —NHS(O)$_2$(C$_{1-6}$ aliphatic), —P(O)$_2$(C$_{1-6}$ aliphatic), —P(O)(C$_{1-6}$ aliphatic)$_2$, —OP(O)(C$_{1-6}$ aliphatic)$_2$, or —OP(O)(OC$_{1-6}$ aliphatic)$_2$.

In certain embodiments, the $R^2$ group of formula II is a group suitable for Click chemistry. Click reactions tend to involve high-energy ("spring-loaded") reagents with well-defined reaction coordinates, that give rise to selective bond-forming events of wide scope. Examples include nucleophilic trapping of strained-ring electrophiles (epoxide, aziridines, aziridinium ions, episulfonium ions), certain carbonyl reactivity (e.g., the reaction between aldehydes and hydrazines or hydroxylamines), and several cycloaddition reactions. The azide-alkyne 1,3-dipolar cycloaddition is one such reaction. Click chemistry is known in the art and one of ordinary skill in the art would recognize that certain $R^2$ moieties of the present invention are suitable for Click chemistry.

According to one embodiment, the $R^2$ group of formula II is an azide-containing group. According to another embodiment, the $R^2$ group of formula II is an alkyne-containing group. In certain embodiments, the $R^2$ group of formula II has a terminal alkyne moiety. According to another embodiment, the $R^2$ group of formula II is an aldehyde-containing group. In certain embodiments, the $R^2$ group of formula II has a terminal hydrazine moiety. In other embodiments, the $R^2$ group of formula II has a terminal oxyamine moiety. In still other embodiments, the $R^2$ group of formula II is a epoxide-containing group. In certain other embodiments, the $R^2$ group of formula II has a terminal maleimide moiety.

In other embodiments, $R^2$ is an optionally substituted 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur. In certain embodiments, $R^2$ is an optionally substituted 5-7 membered saturated or partially unsaturated ring having 0-4 heteroatoms independently selected from nitrogen, oxygen, or sulfur. In other embodiments, $R^2$ is an optionally substituted phenyl ring or a 5-6 membered heteroaryl ring having 1-4 heteroatoms independently selected from nitrogen, oxygen, or sulfur.

In certain embodiments, the $R^2$ group of formula II is an optionally substituted aryl group. Examples include optionally substituted phenyl, optionally substituted pyridyl, optionally substituted naphthyl, optionally substituted pyrenyl, optionally substituted triazole, optionally substituted imidazole, optionally substituted phthalimide, optionally substituted tetrazole, optionally substituted furan, and optionally substituted pyran. When said $R^2$ moiety is a substituted aryl group, suitable substituents on $R^2$ include any of R$^o$, CN, N$_3$, NO$_2$, —CH$_3$, —CH$_2$N$_3$, t-butyl, 5-norbornene-2-yl, octane-5-yl, —CH═CH$_2$, —C≡CH, —CH$_2$C≡CH, —CH$_2$CH$_2$C≡CH, —CH$_2$CH$_2$CH$_2$C≡CH, Cl, Br, I, F, —NH$_2$, —OH, —SH, —CO$_2$H, —C(O)H, —CH$_2$NH$_2$, —CH$_2$OH, —CH$_2$SH, —CH$_2$CO$_2$H, —CH$_2$C(O)H, —C(O)(C$_{1-6}$ aliphatic), —NHC(O)(C$_{1-6}$ aliphatic), —NHC(O)NH—, —NHC(O)NH(C$_{1-6}$ aliphatic), —NHC(S)NH$_2$, —NHC(S)N(C$_{1-6}$ aliphatic)$_2$, —NHC(O)O(C$_{1-6}$ aliphatic), —NHNH$_2$, —NHNHC(O)(C$_{1-6}$ aliphatic), —NHNHC(O)NH$_2$, —NHNHC(O)NH(C$_{1-6}$ aliphatic), —NHNHC(O)O(C$_{1-6}$ aliphatic), —C(O)NH$_2$, —C(O)NH(C$_{1-6}$ aliphatic)$_2$, —C(O)NHNH$_2$, —C(S)N(C$_{1-6}$ aliphatic)$_2$, —OC(O)NH(C$_{1-6}$ aliphatic), —C(O)C(O)(C$_{1-6}$ aliphatic), —C(O)CH$_2$C(O)(C$_{1-6}$ aliphatic), —S(O)$_2$(C$_{1-6}$ aliphatic), —S(O)$_2$O(C$_{1-6}$ aliphatic), —OS(O)$_2$(C$_{1-6}$ aliphatic), —S(O)$_2$NH(C$_{1-6}$ aliphatic), —S(O)(C$_{1-6}$ aliphatic), —NHS(O)$_2$NH(C$_{1-6}$ aliphatic), —NHS(O)$_2$(C$_{1-6}$ aliphatic), —P(O)$_2$(C$_{1-6}$ aliphatic), —P(O)(C$_{1-6}$ aliphatic)$_2$, —OP(O)(C$_{1-6}$ aliphatic)$_2$, or —OP(O)(OC$_{1-6}$ aliphatic)$_2$.

Suitable substituents on $R^2$ further include bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embodiments, $R^2$ is hydrogen.
According to one embodiment, $R^2$ is methyl.
In certain embodiments, $R^2$ is N$_3$.
In other embodiments, $R^2$ is an epoxide ring.
In certain embodiments, the $R^2$ group of formula II is a crown ether. Examples of such crown ethers include 12-crown-4, 15-crown-5, and 18-crown-6.

In still other embodiments, $R^2$ is a detectable moiety. Detectable moieties are known in the art and include those described herein. According to one aspect of the invention, the $R^2$ group of formula II is a fluorescent moiety. Such fluorescent moieties are well known in the art and include coumarins, quinolones, benzoisoquinolones, hostasol, and Rhodamine dyes, to name but a few. Exemplary fluorescent moieties of $R^2$ include anthracen-9-yl, pyren-4-yl, 9-H-carbazol-9-yl, the carboxylate of rhodamine B, and the carboxylate of coumarin 343. In certain embodiments, $R^2$ is a detectable moiety selected from:

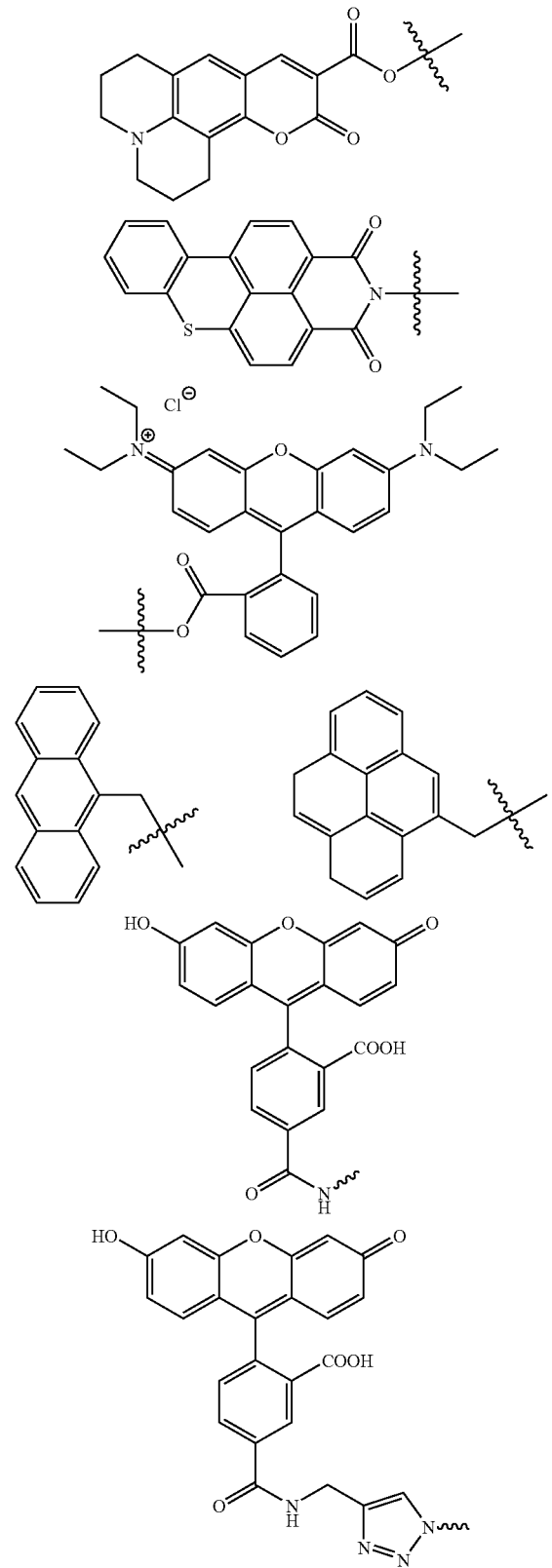

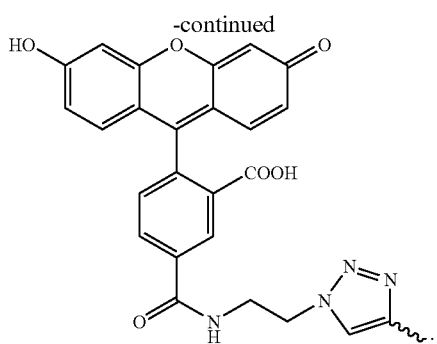

In certain embodiments, $R^2$ is —P(O)(OR)$_2$, or —P(O)(halogen)$_2$. According to one aspect, the present invention provides a compound of formula II, wherein $R^2$ is —P(O)(OH)$_2$. According to another aspect, the present invention provides a compound of formula II, wherein $R^2$ is —P(O)(Cl)$_2$. One of ordinary skill in the art would recognize that when $R^2$ is —P(O)(OR)$_2$, or —P(O)(halogen)$_2$, the $R^2$ group is also capable of forming a covalent bond with the hydrophilic metal surface thus forming a "looped" attachment.

As defined generally above, the $L^1$ group of formula II is a valence bond or a bivalent, saturated or unsaturated, straight or branched $C_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, $L^1$ is a valence bond. In other embodiments, $L^1$ is a bivalent, saturated $C_{1-12}$ alkylene chain, wherein 0-6 methylene units of $L^1$ are independently replaced by -Cy-, —O—, —NH—, —S—, —OC(O)—, —C(O)O—, —C(O)—, —C(O)NH—, or —NHC(O)—, wherein each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In still other embodiments, $L^1$ is a bivalent, saturated $C_{1-6}$ alkylene chain, wherein 0-3 methylene units of $L^1$ are independently replaced by -Cy-, —O—, —NH—, —S—, —OC(O)—, —C(O)O—, —C(O)—, —C(O)NH—, or —NHC(O)—, In certain embodiments, $L^1$ is -Cy- (i.e. a $C_1$ alkylene chain wherein the methylene unit is replaced by -Cy-), wherein -Cy- is an optionally substituted 3-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, the $L^1$ group of formula II is —O—, —S—, —NH—, or —C(O)O—. In other embodiments, the $L^1$ group of formula II is -Cy-, —C(O)—, —C(O)NH—, —NHC(O)—, —NH—O—, or —O-Cy-CH$_2$NH—O—. In still other embodiments, the $L^1$ group of formula II is any of —OCH$_2$—, —OCH$_2$C(O)—, —OCH$_2$CH$_2$C(O)—, —OCH$_2$CH$_2$O—, —OCH$_2$CH$_2$S—, —OCH$_2$CH$_2$C(O)O—, —OCH$_2$CH$_2$NH—, —OCH$_2$CH$_2$NHC(O)—, —OCH$_2$CH$_2$C(O)NH—, and —NHC(O)CH$_2$CH$_2$C(O)O—. According to another aspect, the $L^1$ group of formula II is any of —OCH$_2$CH$_2$NHC(O)CH$_2$CH$_2$C(O)O—, —OCH$_2$CH$_2$NHC(O)CH$_2$OCH$_2$C(O)O—, —OCH$_2$CH$_2$NHC(O)CH$_2$OCH$_2$C(O)NH—, —CH$_2$C(O)NH—, —CH$_2$C(O)NHNH—, or —OCH$_2$CH$_2$NHNH—.

As defined generally above, the $R^2$ group of formula II is, inter alia, a mono-protected amine, a di-protected amine, a protected aldehyde, a protected hydroxyl, a protected carboxylic acid, or a protected thiol. Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene. (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

As defined generally above, the $L^2$ group of formula II is $L^2$ is a valence bond or a bivalent, saturated or unsaturated, straight or branched $C_{1-12}$ alkylene chain, wherein 0-6 methylene units of $L^2$ are independently replaced by -Cy-, —O—, —NR—, —S—, or —C(O)—, wherein each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, $L^2$ is a valence bond. In other embodiments, $L^2$ is a bivalent, saturated $C_{1-12}$ alkylene chain, wherein 0-6 methylene units of $L^2$ are independently replaced by -Cy-, or —O—, —NH—, wherein each -Cy- is independently an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In still other embodiments, $L^2$ is a bivalent, saturated $C_{1-6}$ alkylene chain, wherein 0-2 methylene units of $L^2$ are independently replaced by -Cy-.

In certain embodiments, $L^2$ is -Cy- (i.e., a $C_1$ alkylene chain wherein the methylene unit is replaced by -Cy-), wherein -Cy- is an optionally substituted 3-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, the $L^2$ group of formula II is —O—, —S—, —NH—, or —C(O)—. In still other embodiments, the $L^2$ group of formula II is any of —OCH$_2$—, —OCH$_2$C(O)—, —OCH$_2$CH$_2$C(O)—, —OCH$_2$CH$_2$O—, or —OCH$_2$CH$_2$S—. In other embodiments, the $L^2$ group of formula II is —OC(O)CH$_2$CH$_2$CH$_2$CH$_2$—, —OCH$_2$CH$_2$—, —NHC(O)CH$_2$CH$_2$—, —NHC(O)CH$_2$CH$_2$CH$_2$—, —OC(O)CH$_2$CH$_2$CH$_2$—, —O-Cy-, —O-Cy-CH$_2$—, —O-Cy-NH—, —O-Cy-S—, —O-Cy-C(O)—, or —O-Cy-C(O)O-Cy-.

In certain embodiments, the present invention provides a method for preparing a covalently modified metal surface, comprising the steps of:
(a) modifying a metal substrate to incorporate thereon a plurality of hydroxyl groups;
(b) providing a compound of formula II-a:

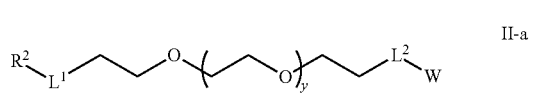

or a salt thereof, wherein:
W is —C(═O)OH, —C(═O)X, —P(═O)(OH)$_2$, —P(═O)(X)$_2$, —P(═O)(R$^a$)OH, —P(═O)(R$^a$)X, —O—S(═O)$_2$OH, —S(═O)$_2$OH, —Si(R$^a$)$_2$OH, —Si(OR$^a$)$_2$OH, —Si(R$^a$)$_2$X, —Si(R$^a$)(OH)$_2$, —Si(R$^a$)X$_2$, —Si(OR$^a$)$_2$X, C(═O)H, —N═C═S, —N═C═O, phenol, thiophenol, or an epoxide;
each X is independently Cl, Br, or I; and
each R$^a$ is hydrogen, an alkyl group, or an aryl group;
y is 0-2500;
$R^2$ is hydrogen, halogen, NO$_2$, CN, N$_3$, —N═C═O, —C(R)═NN(R)$_2$, —P(O)(OR)$_2$, —P(O)(X')$_2$, a 9-30 membered crown ether, a mono-protected amine, a di-protected amine, a protected aldehyde, a protected hydroxyl, a protected carboxylic acid, a protected thiol, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
each X$_1$ is independently halogen;
each R is independently hydrogen or an optionally substituted aliphatic group;
$L^1$ is a valence bond or a bivalent, saturated or unsaturated, straight or branched C$_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and
$L^2$ is a valence bond or a bivalent, saturated or unsaturated, straight or branched C$_{1-12}$ alkylene chain, wherein 0-6 methylene units of $L^2$ are independently replaced by -Cy-, —O—, —NR—, —S—, or —C(O)—, wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.
and
(c) coupling the compound of formula II-a to one or more of the hydroxyl groups on the metal surface.

Each of the $R^2$, $L^1$, y, and $L^2$ groups of formula II-a are as described in classes and subclasses for compounds of formula II, both singly and in combination.

In other embodiments, the present invention provides a compound of formula II-a':

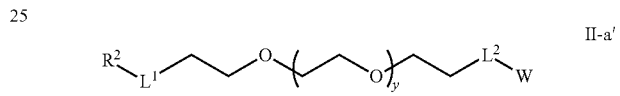

or a salt thereof, wherein:
W is —Si(R$^a$)$_2$OH, —Si(OR$^a$)$_2$OH, —Si(R$^a$)$_2$X, —Si(R$^a$)(OH)$_2$, —Si(R$^a$)X$_2$, or —Si(OR$^a$)$_2$X;
each X is independently Cl, Br, or I; and
each R$^a$ is hydrogen, an alkyl group, or an aryl group;
y is 0-2500;
$R^2$ is hydrogen, halogen, NO$_2$, CN, N$_3$, —N═C═O, —C(R)═NN(R)$_2$, —P(O)(OR)$_2$, —P(O)(X')$_2$, a 9-30 membered crown ether, a mono-protected amine, a di-protected amine, a protected aldehyde, a protected hydroxyl, a protected carboxylic acid, a protected thiol, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
each X' is independently halogen;
each R is independently hydrogen or an optionally substituted aliphatic group;
$L^1$ is a valence bond or a bivalent, saturated or unsaturated, straight or branched C$_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and
$L^2$ is a valence bond or a bivalent, saturated or unsaturated, straight or branched C$_{1-12}$ alkylene chain, wherein 0-6 methylene units of $L^2$ are independently replaced by -Cy-, —O—, —NR—, —S—, or —C(O)—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

Each of the $R^2$, $L^1$, y, and $L^2$ groups of formula II-a' are as described in classes and subclasses for compounds of formula II, both singly and in combination.

In other embodiments, the present invention provides a method for preparing a covalently modified metal surface, comprising the steps of:

(a) modifying a metal substrate to incorporate thereon a plurality of hydroxyl groups;

(b) providing a compound of formula II-b:

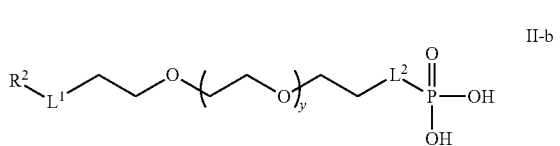

or a salt thereof, wherein:
y is 10-2500;
$R^2$ is hydrogen, halogen, $NO_2$, CN, $N_3$, —N=C=O, —C(R)=NN(R)$_2$, —P(O)(OR)$_2$, —P(O)(X')$_2$, a 9-30 membered crown ether, a mono-protected amine, a di-protected amine, a protected aldehyde, a protected hydroxyl, a protected carboxylic acid, a protected thiol, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
each X' is independently halogen;
each R is independently hydrogen or an optionally substituted aliphatic group;
$L^1$ is a valence bond or a bivalent, saturated or unsaturated, straight or branched $C_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and
$L^2$ is a valence bond or a bivalent, saturated or unsaturated, straight or branched $C_{1-12}$ alkylene chain, wherein 0-6 methylene units of $L^2$ are independently replaced by -Cy-, —O—, —NR—, —S—, or —C(O)—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

and (c) coupling the compound of formula II-b to one or more of the hydroxyl groups on the metal surface by dehydration reaction.

Each of the $R^2$, $L^1$, y, and $L^2$ groups of formula II-b are as described in classes and subclasses for compounds of formula II, both singly and in combination.

In other embodiments, the present invention provides a method for preparing a covalently modified metal surface, comprising the steps of:

(a) modifying a metal substrate to incorporate thereon a plurality of hydroxyl groups;

(b) providing a compound of formula II-c:

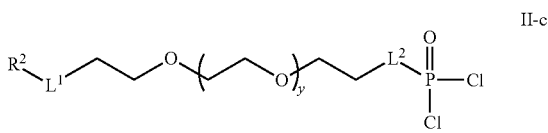

or a salt thereof, wherein:
y is 10-2500;
$R^2$ is hydrogen, halogen, $NO_2$, CN, $N_3$, —N=C=O, —C(R)=NN(R)$_2$, —P(O)(OR)$_2$, —P(O)(X')$_2$, a 9-30 membered crown ether, a mono-protected amine, a di-protected amine, a protected aldehyde, a protected hydroxyl, a protected carboxylic acid, a protected thiol, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
each X' is independently halogen;
each R is independently hydrogen or an optionally substituted aliphatic group;
$L^1$ is a valence bond or a bivalent, saturated or unsaturated, straight, or branched $C_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and
$L^2$ is a valence bond or a bivalent, saturated or unsaturated, straight or branched $C_{1-12}$ alkylene chain, wherein 0-6 methylene units of $L^2$ are independently replaced by -Cy-, —O—, —NR—, —S—, or —C(O)—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. and (c) coupling the compound of formula II-c to one or more of the hydroxyl groups on the metal surface by condensation reaction.

Each of the $R^2$, $L^1$, y, and $L^2$ groups of formula II-c are as described in classes and subclasses for compounds of formula II, both singly and in combination.

In certain embodiments, the $R^1$ group of formula I is a group of formula II-d:

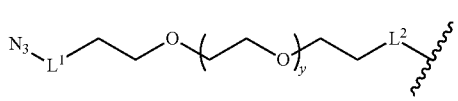

or a salt thereof, wherein:
y is 0-2500;
each R is independently hydrogen or an optionally substituted aliphatic group;
$L^1$ is a valence bond or a bivalent, saturated or unsaturated, straight or branched $C_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and
$L^2$ is a valence bond or a bivalent, saturated or unsaturated, straight or branched $C_{1-12}$ alkylene chain, wherein 0-6 methylene units of $L^2$ are independently replaced by -Cy-, —O—, —NR—, —S—, or —C(O)—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

Each of the $L^1$, y, and $L^2$ groups of formula II-d are as described in classes and subclasses for compounds of formula II, both singly and in combination.

In certain embodiments, the present invention provides a method for preparing a covalently modified metal surface, comprising the steps of:
(a) modifying a metal substrate to incorporate thereon a plurality of hydroxyl groups;
(b) providing a compound of formula II-e:

or a salt thereof, wherein:
W is —C(=O)OH, —C(=O)X, —P(=O)(OH)$_2$, —P(=O)(X)$_2$, —P(=O)(R$^a$)OH, —P(=O)(R$^a$)X, —O—S(=O)$_2$OH, —S(=O)$_2$OH, —Si(R$^a$)$_2$OH, —Si(OR$^a$)$_2$OH, —Si(R$^a$)$_2$X, —Si(R$^a$)(OH)$_2$, —Si(R$^a$)X$_2$, —Si(OR$^a$)$_2$X, C(=O)H, —N=C=S, —N=C=O, phenol, thiophenol, or an epoxide;
each X is independently Cl, Br, or I; and
each $R^a$ is hydrogen, an alkyl group, or an aryl group;
y is 0-2500;
each R is independently hydrogen or an optionally substituted aliphatic group;
$L^1$ is a valence bond or a bivalent, saturated or unsaturated, straight or branched $C_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and
$L^2$ is a valence bond or a bivalent, saturated or unsaturated, straight or branched $C_{1-12}$ alkylene chain, wherein 0-6 methylene units of $L^2$ are independently replaced by -Cy-, —O—, —NR—, —S—, or —C(O)—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur, and (c) coupling the compound of formula II-e to one or more of the hydroxyl groups on the metal surface.

Each of the $L^1$, y, W, and $L^2$ groups of formula II-e are as described in classes and subclasses for compounds of formulae I and II, both singly and in combination.

In other embodiments, the present invention provides a method for preparing a covalently modified metal surface, comprising the steps of:
(a) modifying a metal substrate to incorporate thereon a plurality of hydroxyl groups;
(b) providing a compound of formula II-e; and
(c) coupling the compound of formula II-e to one or more of the hydroxyl groups on the metal surface, further comprising the step of coupling the azide-terminal end to a suitable group via Click chemistry.

In other embodiments, the present invention provides a compound of formula II-e':

or a salt thereof, wherein:
W is —Si(R$^a$)$_2$OH, —Si(OR$^a$)$_2$OH, —Si(R$^a$)$_2$X, —Si(R$^a$)(OH)$_2$, —Si(R$^a$)X$_2$, or —Si(OR$^a$)$_2$X;
each X is independently Cl, Br, or I; and
each $R^a$ is hydrogen, an alkyl group, or an aryl group;
y is 0-2500;

each R is independently hydrogen or an optionally substituted aliphatic group;

$L^1$ is a valence bond or a bivalent, saturated or unsaturated, straight or branched $C_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and $L^2$ is a valence bond or a bivalent, saturated or unsaturated, straight or branched $C_{1-12}$ alkylene chain, wherein 0-6 methylene units of $L^2$ are independently replaced by -Cy-, —O—, —NR—, —S—, or —C(O)—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

Each of the $L^1$, y, W, and $L^2$ groups of formula II-e' are as described in classes and subclasses for compounds of formulae I and II, both singly and in combination.

In other embodiments, the $R^1$ group of formula I is a copolymer group. Multiblock copolymers of the present invention are prepared by methods known to one of ordinary skill in the art and those described in detail in U.S. patent application Ser. No. 11/325,020 filed Jan. 4, 2006, the entirety of which is hereby incorporated herein by reference. According to another aspect, $R^1$ is a block copolymer group of formula III:

urated, or aryl bicyclic ring having 0-5 heteroatoms independently selected from nitrogen, oxygen, or sulfur, or a detectable moiety;

each X' is independently halogen;

each R is independently hydrogen or an optionally substituted aliphatic group;

$L^1$ is a valence bond or a bivalent, saturated or unsaturated, straight or branched $C_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and $L^3$ is a valence bond or a bivalent, saturated or unsaturated, straight or branched $C_{1-12}$ alkylene chain, wherein 0-6 methylene units of Q are independently replaced by -Cy-, —O—, —NH—, —S—, or —C(O)—, wherein:

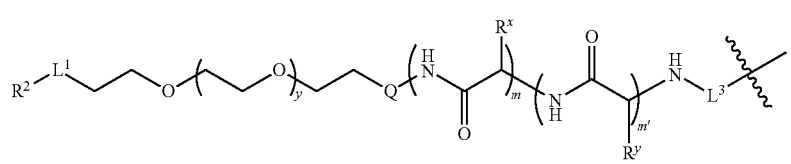

III wherein:

y is 1-2500;

m is 1 to 1000;

m' is 0 to 1000;

$R^x$ and $R^y$ are each independently a natural or unnatural amino acid side-chain group, wherein $R^x$ and $R^y$ are different from each other;

$R^2$ is hydrogen, halogen, NO$_2$, CN, N$_3$, —N=C=O, —C(R)=NN(R)$_2$, —P(O)(OR)$_2$, —P(O)(X')$_2$, a 9-30 membered crown ether, a mono-protected amine, a di-protected amine, a protected aldehyde, a protected hydroxyl, a protected carboxylic acid, a protected thiol, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsat- -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, the m' group of formula III is 1-1000. In certain embodiments, the m' group of formula III is 0. In other embodiments, m' is 1-1000. According to other embodiments, m and m' are independently 10 to 100 repeat units. In still other embodiments, m is 1-20 repeat units and m' is 10-50 repeat units.

As defined generally above, the Q group of formula III is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO₂—, —NHSO₂—, —SO₂NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Q is a valence bond. In other embodiments, Q is a bivalent, saturated $C_{1-12}$ alkylene chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, Q is -Cy- (i.e. a $C_1$ alkylene chain wherein the methylene unit is replaced by -Cy-), wherein -Cy- is an optionally substituted 5-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, $R^x$ is a crosslinkable amino acid side-chain group and $R^y$ is a hydrophobic amino acid side-chain group. Such crosslinkable amino acid side-chain groups include tyrosine, serine, cysteine, threonine, aspartic acid (also known as aspartate, when charged), glutamic acid (also known as glutamate, when charged), asparagine, histidine, lysine, arginine, and glutamine. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. In other embodiments, $R^y$ is an ionic amino acid side-chain group. Such ionic amino acid side chain groups includes a lysine side-chain, arginine side-chain, or a suitably protected lysine or arginine side-chain, an aspartic acid side chain, glutamic acid side-chain, or a suitably protected aspartic acid or glutamic acid side-chain. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboylate functional groups of $R^x$ and $R^y$ are as described herein.

In other embodiments, $R^y$ comprises a mixture of hydrophobic and hydrophilic amino acid side-chain groups such that the overall poly(amino acid) block comprising $R^y$ is hydrophobic. Such mixtures of amino acid side-chain groups include phenylalanine/tyrosine, phenalanine/serine, leucine/tyrosine, and the like. According to another embodiment, $R^y$ is a hydrophobic amino acid side-chain group selected from phenylalanine, alanine, or leucine, and one or more of tyrosine, serine, or threonine.

As defined above, $R^x$ is a natural or unnatural amino acid side-chain group capable of forming cross-links. It will be appreciated that a variety of amino acid side-chain functional groups are capable of such cross-linking, including, but not limited to, carboxylate, hydroxyl, thiol, and amino groups. Examples of $R^x$ moieties having functional groups capable of forming cross-links include a glutamic acid side-chain, —CH₂C(O)CH, an aspartic acid side-chain, —CH₂CH₂C(O)OH, a cystein side-chain, —CH₂SH, a serine side-chain, —CH₂OH, an aldehyde containing side-chain, —CH₂C(O)H, a lysine side-chain, —(CH₂)₄NH₂, an arginine side-chain, —(CH₂)₃NHC(=NH)NH₂, a histidine side-chain, —CH₂-imidazol-4-yl.

In certain embodiments, the present invention provides a method for preparing a covalently modified metal surface, comprising the steps of:

(a) modifying a metal substrate to incorporate thereon a plurality of hydroxyl groups;

(b) providing a compound of formula III-a:

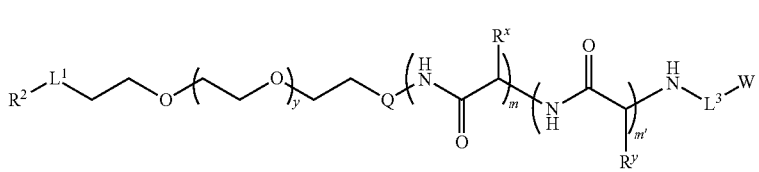

wherein:

W is —C(=O)OH, —C(=O)X, —P(=O)(OH)₂, —P(=O)(X)₂, —P(=O)(Rᵃ)OH, —P(=O)(Rᵃ)X, —O—S(=O)₂OH, —S(=O)₂OH, —Si(Rᵃ)₂OH, —Si(ORᵃ)₂OH, —Si(Rᵃ)₂X, —Si(Rᵃ)(OH)₂, —Si(Rᵃ)X₂, —Si(ORᵃ)₂X, C(=O)H, —N=C=S, —N=C=O, phenol, thiophenol, or an epoxide;

each X is independently Cl, Br, or I; and each $R^a$ is hydrogen, an alkyl group, or an aryl group;

y is 1-2500;

m is 1 to 1000;

m' is 0 to 1000;

$R^x$ and $R^y$ are each independently a natural or unnatural amino acid side-chain group, wherein $R^x$ and $R^y$ are different from each other;

R² is hydrogen, halogen, NO₂, CN, N₃, —N=C=O, —C(R)=NN(R)₂, —P(O)(OR)₂, —P(O)(X')₂, a 9-30 membered crown ether, a mono-protected amine, a di-protected amine, a protected aldehyde, a protected hydroxyl, a protected carboxylic acid, a protected thiol, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

each X' is independently halogen;
each R is independently hydrogen or an optionally substituted aliphatic group;
$L^1$ is a valence bond or a bivalent, saturated or unsaturated, straight or branched $C_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
  -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and
$L^3$ is a valence bond or a bivalent, saturated or unsaturated, straight or branched $C_{1-12}$ alkylene chain, wherein 0-6 methylene units of Q are independently replaced by -Cy-, —O—, —NH—, —S—, or —C(O)—, wherein:
  -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
and
(c) coupling the compound of formula III-a to one or more of the hydroxyl groups on the metal surface.

Each of the $R^2$, $L^1$, y, m, m', Q, $R^x$, $R^y$, and $L^3$ groups of formula III-a are as described in classes and subclasses for compounds of formulae II and III, both singly and in combination.

In certain embodiments, the present invention provides a method for preparing a covalently modified metal surface, comprising the steps of:
(a) modifying a metal substrate to incorporate thereon a plurality of hydroxyl groups;
(b) providing a compound of formula III-b:

wherein:
y is 1-2500;
m is 1 to 1000;
m' is 0 to 1000;
$R^x$ and $R^y$ are each independently a natural or unnatural amino acid side-chain group, wherein $R^x$ and $R^y$ are different from each other;
$R^2$ is hydrogen, halogen, NO$_2$, CN, N$_3$, —N=C=O, —C(R)=NN(R)$_2$, —P(O)(OR)$_2$, —P(O)(X')$_2$, a 9-30 membered crown ether, a mono-protected amine, a di-protected amine, a protected aldehyde, a protected hydroxyl, a protected carboxylic acid, a protected thiol, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
each X' is independently halogen;
each R is independently hydrogen or an optionally substituted aliphatic group;
$L^1$ is a valence bond or a bivalent, saturated or unsaturated, straight or branched $C_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
  each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
  -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and
$L^3$ is a valence bond or a bivalent, saturated or unsaturated, straight or branched $C_{1-12}$ alkylene chain, wherein 0-6 methylene units of Q are independently replaced by -Cy-, —O—, —NH—, —S—, or —C(O)—, wherein:
  -Cy- is an optionally substituted 5-8 membered bivalent, saturated, partially unsaturated, or aryl ring having 0-4

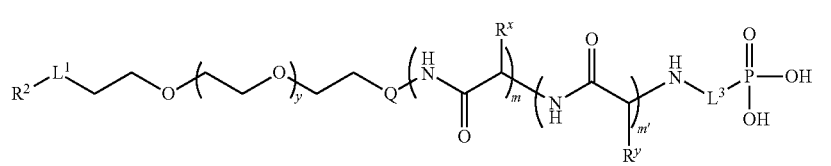

III-b heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
and
(c) coupling the compound of formula III-b to one or more of the hydroxyl groups on the metal surface by dehydration reaction.

Each of the $R^2$, $L^1$, y, m, m', Q, $R^x$, $R^y$, and $L^3$ groups of formula III-b are as described in classes and subclasses for compounds of formula III, both singly and in combination.

In certain embodiments, the present invention provides a method for preparing a covalently modified metal surface, comprising the steps of:
(a) modifying a metal substrate to incorporate thereon a plurality of hydroxyl groups;
(b) providing a compound of formula III-c:

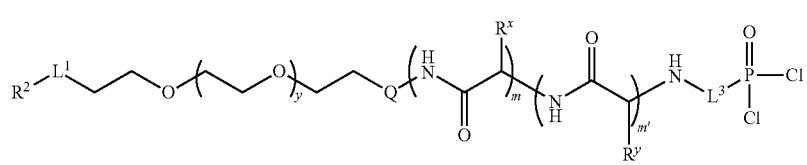

III-c wherein:
y is 10-2500;
m is 1 to 1000;
m' is 0 to 1000;
$R^x$ and $R^y$ are each independently a natural or unnatural amino acid side-chain group, wherein $R^x$ and $R^y$ are different from each other;
$R^2$ is hydrogen, halogen, $NO_2$, CN, $N_3$, —N=C=O, —C(R)=NN(R)$_2$, —P(O)(OR)$_2$, —P(O)(X')$_2$, a 9-30 membered crown ether, a mono-protected amine, a di-protected amine, a protected aldehyde, a protected hydroxyl, a protected carboxylic acid, a protected thiol, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
each X' is independently halogen;
each R is independently hydrogen or an optionally substituted aliphatic group;
$L^1$ is a valence bond or a bivalent, saturated or unsaturated, straight or branched $C_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and
$L^3$ is a valence bond or a bivalent, saturated or unsaturated, straight or branched $C_{1-12}$ alkylene chain, wherein 0-6 methylene units of Q are independently replaced by -Cy-, —O—, —NH—, —S—, or —C(O)—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
and
(c) coupling the compound of formula III-c to one or more of the hydroxyl groups on the metal surface by dehydration reaction.

Each of the $R^2$, $L^1$, y, m, m', Q, $R^x$, $R^y$, and $L^3$ groups of formula III-c are as described in classes and subclasses for compounds of formula III, both singly and in combination.

In other embodiments, $R^1$ is a block copolymer group of formula IV:

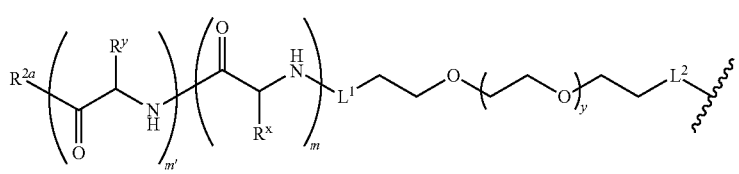

IV wherein:

y is 10-2500;

m is 1 to 1000;

m' is 0 to 1000;

$R^x$ and $R^y$ are each independently a natural or unnatural amino acid side-chain group, wherein $R^x$ and $R^y$ are different from each other;

$R^2$ is hydrogen, halogen, $NO_2$, CN, $N_3$, —N=C=O, —C(R)=NN(R)$_2$, —P(O)(OR)$_2$, —P(O)(X')$_2$, a 9-30 membered crown ether, a mono-protected amine, a di-protected amine, a protected aldehyde, a protected hydroxyl, a protected carboxylic acid, a protected thiol, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

each X' is independently halogen;

each R is independently hydrogen or an optionally substituted aliphatic group;

$L^1$ is a valence bond or a bivalent, saturated or unsaturated, straight or branched $C_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and $L^2$ is a valence bond or a bivalent, saturated or unsaturated, straight or branched $C_{1-12}$ alkylene chain, wherein 0-6 methylene units of Q are independently replaced by -Cy-, —O—, —NH—, —S—, or —C(O)—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —NHR$^3$, —N(R$^3$)$_2$, —NHC(O)R$^3$, —NR$^3$C(O)R$^3$, —NHC(O)NHR$^3$, —NHC(O)N(R$^3$)$_2$, —NR$^3$C(O)NHR$^3$, —NR$^3$C(O)N(R$^3$)$_2$, —NHC(O)OR$^3$, —NR$^3$C(O)OR$^3$, —NHSO$_2$R$^3$, or —NR$^3$SO$_2$R$^3$; and each $R^3$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or:

two $R^3$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

Each of the $R^2$, $L^1$, y, m, m', Q, $R^x$, $R^y$, and $L^2$ groups of formula IV are as described in classes and subclasses for compounds of formulae II and III, both singly and in combination.

As defined generally above, the $R^{2a}$ group of formula IV is a mono-protected amine, a di-protected amine, —NHR$^3$, —N(R$^3$)$_2$, —NHC(O)R$^3$, —NR$^3$C(O)R$^3$, —NHC(O)NHR$^3$, —NHC(O)N(R$^3$)$_2$, —NR$^3$C(O)NHR$^3$, —NR$^3$C(O)N(R$^3$)$_2$, —NHC(O)OR$^3$, —NR$^3$C(O)OR$^3$, —NHSO$_2$R$^3$, or —NR$^3$SO$_2$R$^3$, wherein each $R^3$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two $R^3$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

In certain embodiments, the $R^{2a}$ group of formula IV is —NHR$^3$ or —N(R$^3$)$_2$ wherein each $R^3$ is an optionally substituted aliphatic group. One exemplary $R^3$ group is 5-norbornen-2-yl-methyl. According to yet another aspect of the present invention, the $R^{2a}$ group of formula IV is —NHR$^3$ wherein $R^3$ is a $C_{1-6}$ aliphatic group substituted with $N_3$. Examples include —CH$_2$N$_3$. In some embodiments, $R^3$ is an optionally substituted $C_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, and 2-(2-dipropargylaminoethoxy)-ethyl. In other embodiments, $R^3$ is an optionally substituted $C_{2-6}$ alkenyl group. Examples include vinyl, allyl, crotyl, 2-propenyl, and but-3-enyl. When $R^3$ group is a substituted aliphatic group, suitable substituents on $R^3$ include $N_3$, CN, and halogen. In certain embodiments, $R^3$ is —CH$_2$CN, —CH$_2$CH$_2$CN, —CH$_2$CH(OCH$_3$)$_2$, 4-(bisbenzyloxymethyl)phenylmethyl, and the like.

According to another aspect of the present invention, the $R^{2a}$ group of formula IV is —NHR$^3$ wherein $R^3$ is an optionally substituted $C_2$ alkynyl group. Examples include —C≡CH, —CH$_2$C≡CH, —CH$_2$C≡CCH$_3$, and —CH$_2$CH$_2$C≡CH.

In certain embodiments, the $R^{2a}$ group of formula IV is —NHR$^3$ wherein R$^3$ is an optionally substituted 5-8-membered aryl ring. In certain embodiments, R$^3$ is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^{2a}$ is 4-t-butoxycarbonylaminophenylamino, 4-azidomethylphenamino, or 4-propargyloxyphenylamino.

In certain embodiments, the $R^{2a}$ group of formula IV is —NHR$^3$ wherein R$^3$ is an optionally substituted phenyl ring. Suitable substituents on the R$^3$ phenyl ring include halogen; —(CH$_2$)$_{0-4}$R$^\circ$; —(CH$_2$)$_{0-4}$R$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-4}$Ph which may be substituted with R$^\circ$; —CH═CHPh, which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; SiR$^\circ$$_3$; wherein each independent occurrence of R$^\circ$ is as defined herein supra. In other embodiments, the $R^{2a}$ group of formula IV is —NHR$^3$ wherein R$^3$ is phenyl substituted with one or more optionally substituted C$_{1-6}$ aliphatic groups. In still other embodiments, R$^3$ is phenyl substituted with vinyl, allyl, acetylenyl, —CH$_2$N$_3$, —CH$_2$CH$_2$N$_3$, —CH$_2$C≡CCH$_3$, or —CH$_2$C≡CH.

In certain embodiments, the $R^{2a}$ group of formula IV is —NHR$^3$ wherein R$^3$ is phenyl substituted with N$_3$, N(R$^\circ$)$_2$, CO$_2$R$^\circ$, or C(O)R$^\circ$ wherein each R$^\circ$ is independently as defined herein supra.

In certain embodiments, the $R^{2a}$ group of formula IV is —N(R$^3$)$_2$ wherein each R$^3$ is independently an optionally substituted group selected from aliphatic, phenyl, naphthyl, a 5-6 membered aryl ring having 1-4 heteroatoms independently selected from nitrogen, oxygen, or sulfur, or a 8-10 membered bicyclic aryl ring having 1-5 heteroatoms independently selected from nitrogen, oxygen, or sulfur, or a detectable moiety.

In other embodiments, the $R^{2a}$ group of formula IV is —N(R$^3$)$_2$ wherein the two R$^3$ groups are taken together with said nitrogen atom to form an optionally substituted 4-7 membered saturated, partially unsaturated, or aryl ring having 1-4 heteroatoms independently selected from nitrogen, oxygen, or sulfur. According to another embodiment, the two R$^3$ groups are taken together to form a 5-6-membered saturated or partially unsaturated ring having one nitrogen wherein said ring is substituted with one or two oxo groups. Such $R^{2a}$ groups include, but are not limited to, phthalimide, maleimide and succinimide.

In certain embodiments, the $R^{2a}$ group of formula IV is a mono-protected or di-protected amino group. In certain embodiments $R^{2a}$ is a mono-protected amine. In certain embodiments $R^{2a}$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^{2a}$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^{2a}$ moiety is phthalimido. In other embodiments, the $R^{2a}$ moiety is mono- or di-benzylamino or mono- or di-allylamino.

In certain embodiments, the $R^{2a}$ group of formula IV comprises a group suitable for Click chemistry. One of ordinary skill in the art would recognize that certain $R^{2a}$ groups of the present invention are suitable for Click chemistry.

Compounds of formula IV having $R^{2a}$ groups comprising groups suitable for Click chemistry are useful for conjugating said compounds to biological systems such as proteins, viruses, and cells, to name but a few. Thus, another embodiment of the present invention provides a method of conjugating the $R^{2a}$ group of a compound of formula IV to a macromolecule via Click chemistry. Yet another embodiment of the present invention provides a macromolecule conjugated to a compound of formula IV via the $R^{2a}$ group.

According to one embodiment, the $R^{2a}$ group of formula IV is an azide-containing group. According to another embodiment, the $R^{2a}$ group of formula IV is an alkyne-containing group.

In certain embodiments, the $R^{2a}$ group of formula IV has a terminal alkyne moiety. In other embodiments, the $R^{2a}$ group of formula IV is an alkyne-containing moiety having an electron withdrawing group. Accordingly, in such embodiments, the $R^{2a}$ group of formula IV is

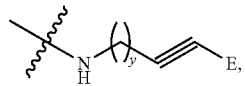

wherein E is an electron withdrawing group and y is 0-6. Such electron withdrawing groups are known to one of ordinary skill in the art. In certain embodiments, E is an ester. In other embodiments, the $R^{2a}$ group of formula IV is

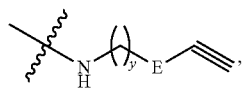

wherein E is an electron withdrawing group, such as a —C(O)O— group and y is 0-6.

According to another embodiment, the present invention provides compounds of formula IV, as described above, wherein said compounds have a polydispersity index ("PDI") of about 1.0 to about 1.2. According to another embodiment, the present invention provides compounds of formula IV, as described above, wherein said compound has a polydispersity index ("PDI") of about 1.03 to about 1.15. According to yet another embodiment, the present invention provides compounds of formula IV, as described above, wherein said compound has a polydispersity index ("PDI") of about 1.10 to about 1.12. According to other embodiments, the present invention provides compounds of formula IV having a PDI of less than about 1.10.

In certain embodiments, the present invention provides compounds of formula IV, as described above, wherein n is about 225. In other embodiments, n is about 200 to about 300. In still other embodiments, n is about 200 to about 250. In still other embodiments, n is about 100 to about 150. In still other embodiments, n is about 400 to about 500.

Exemplary $R^{2a}$ groups of formula IV are set forth in Table 1, below.

TABLE 1

Representative $R^{2a}$ Groups

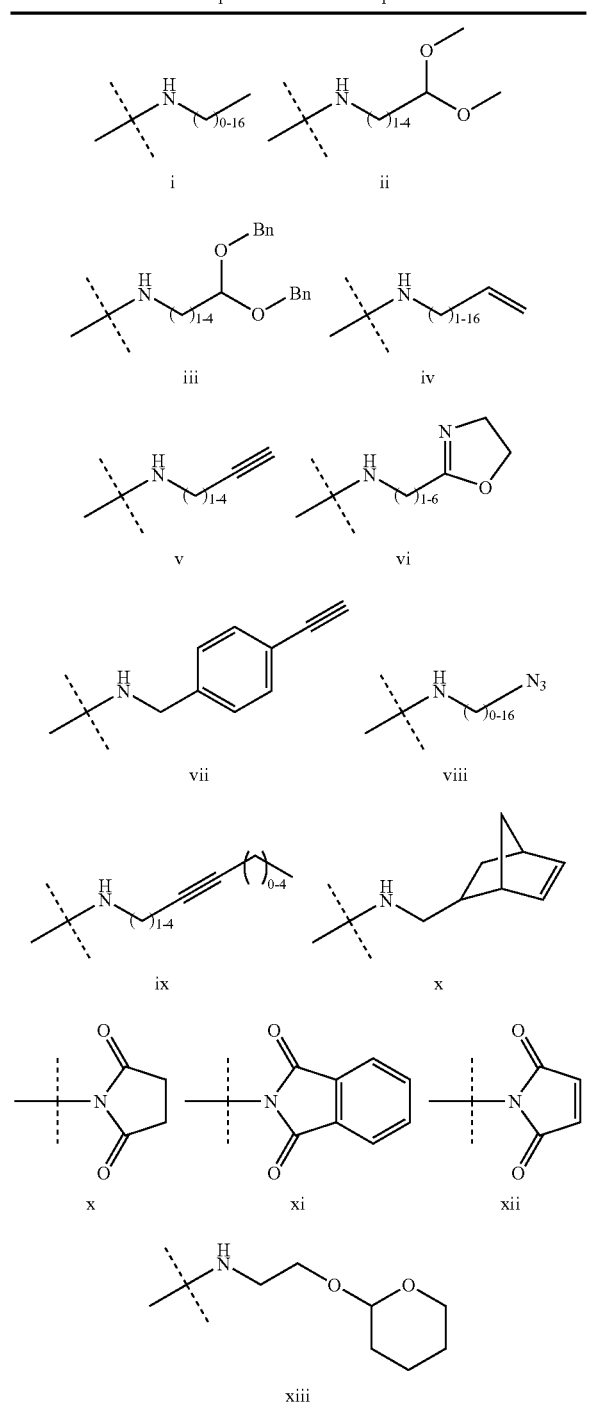

TABLE 1-continued

Representative $R^{2a}$ Groups

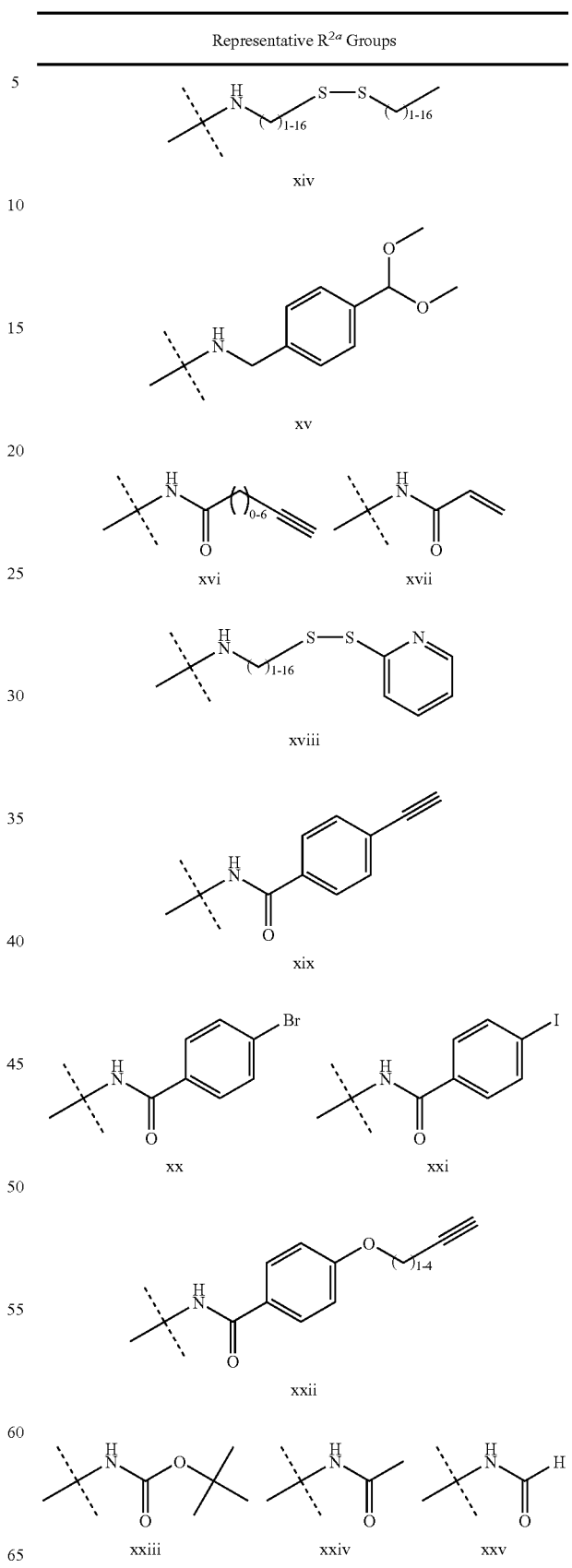

TABLE 1-continued

Representative R²ᵃ Groups xxvi, xxvii, xxviii, xxix, xxx, xxxi, xxxii, xxxiii, xxxiv, xxxv, xxxvi, xxxvii, xxxviii, xxxix, xl, xli, xlii, xliii, xliv, xlv

TABLE 1-continued

Representative $R^{2a}$ Groups

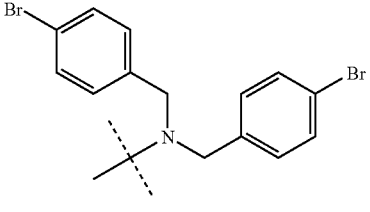

xlvi

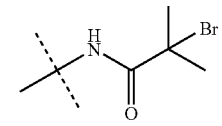

xlvii

In certain embodiments, the $R^{2a}$ group of formula IV is selected from any of those $R^{2a}$ groups depicted in Table 1, supra. In other embodiments, the $R^{2a}$ group of formula IV is group V, viii, xvi, xix, xxii, xxx, xxxi, xxxii, xxxiii, xxxiv, xxxv, xxxvi, xxxvii, or xlii. In yet other embodiments, the $R^{2a}$ group of formula IV is xv, xviii, xx, xxi, xxxviii, or xxxix.

Small Molecule Organic Groups

As defined generally above, $R^1$ is, inter alia, a small molecule organic group. In certain embodiments, $R^1$ is selected from monosaccharides (e.g., glucose, galactose, or fructose) disaccharides (e.g., sucrose, lactose, or maltose), phosphorylcholines, phosoplipids, cyclodextran, small molecule drugs, optionally substituted aliphatic groups, optionally substituted cyclic groups, detectable moieties, and the like.

In certain embodiments, $R^1$ is a group of formula V:

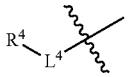

V $R^4$ is hydrogen, halogen, $NO_2$, CN, $N_3$, —N=C=O, —C(R)=NN(R)$_2$, —P(O)(OR)$_2$, —P(O)(X")$_2$, a 9-30 membered crown ether, a small molecule drug, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

each X" is independently halogen;

each R is independently hydrogen or an optionally substituted aliphatic group;

$L^4$ is a valence bond or a bivalent, saturated or unsaturated, straight or branched $C_{1-12}$ alkylene chain, wherein 0-6 methylene units of $L^4$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—, wherein:

each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In other embodiments, the $R^1$ group of formula I or the $R^4$ group of formula V is a small molecule drug. For formula I, it is contemplated that the small molecule drug is either bonded directly to W or through a linker group $L^5$, wherein $L^5$ is as defined for the $L^2$ group of formula II and in classes and subclasses described for $L^2$ herein. In certain embodiments, the linker group $L^4$ or $L^5$ is a hydrolytically cleavable linker group. It will be appreciated that when the $R^1$ group of formula I or the $R^4$ group of formula V is a small molecule drug and the corresponding $L^4$ or $L^5$ linker group is a hydrolytically cleavable linker group, then the small molecule drug can be slowly released by the metal surface covalently modified therewith, upon, for example, implantation into a patient. Such hydrolytically cleavable linker groups are well known to one or ordinary skill in the art.

In certain embodiments, the small molecule drug is a member of the taxane family of anti-tubulin agents. In other embodiments, the small molecule drug is paclitaxel. In still other embodiments, the small molecule drug is docetaxel. In certain embodiments, the small molecule drug is a member of the anthracyline family of cytotoxic agents. In other embodiments, the small molecule drug is doxorubicin. In still other embodiments, the small molecule drug is daunorubicin. In still other embodiments, the small molecule drug is epirubicin.

In other embodiments, the $R^1$ group of formula I or the $R^4$ group of formula V is an antithrombogenic oligopeptide. Such antithrombogenic oligopeptide are well known in the art and include sequences such as Cys-Pro-Arg, Cys-(L)Phe-Pro-Arg, and/or Cys-(D)Phe-Pro-Arg.

It will also be appreciated that the $R^2$ group of formula II can be an antithromobgenic oligopeptide, such as those name above, attached to PEG via a hydrolytically stable linkage.

In other embodiments, the $R^1$ group of formula I or the $R^4$ group of formula V is a cell-binding oligopeptide. Cell-binding oligopeptides are well known in the art and include $\alpha_v\beta_3$ and $\alpha_v\beta_5$ integrin binding peptide sequences such as those containing the Arg-Gly-Asp (RGD) and Asn-Gly-Arg (NGR) oligopeptide sequences. In one embodiment, the $R^1$ group of formula I or the $R^4$ group of formula V is the cell-binding oligopeptide GRGDS. In another embodiment, the oligopeptide sequence is a cyclic RGD sequence such as c(RGDfK).

It will also be appreciated that the $R^2$ group of formula II can be a cell-binding oligopeptide, such as those name above, attached to PEG via a hydrolytically stable linkage It will also be appreciated that when the $R^2$ group of formula II is a small molecule drug attached to the PEG via a hydrolytically cleavable linker group, then that small molecule drug is slowly released by the metal surface covalently modified therewith leaving the PEGylated metal surface. In certain embodiments, the small molecule drug connected to PEG via a hydrolytically cleavable linker is a member of the taxane family of anti-tubulin agents. In other embodiments, the small molecule drug connected to PEG via a hydrolytically cleavable linker is paclitaxel. In still other embodiments, the small molecule drug connected to PEG via a hydrolytically cleavable linker is docetaxel.

It will also be appreciated that when the polymers of formula III are used for surface modification, a hydrophobic small molecule drug can be encapsulated in the hydrophobic region of polymer layer. Such encapsulated small molecule drugs can be slowly released by the diffusion from the polymer layer. In certain embodiments, the encapsulated small molecule drug is a member of the taxane family of anti-tubulin agents. In other embodiments, the encapsulated small molecule drug is paclitaxel. In still other embodiments, the encapsulated small molecule drug is docetaxel.

When the polymers of formula III are used for surface modification and encapsulation of a hydrophobic small molecule drug, the $R^x$ groups of the polymer layer may be optionally crosslinked to control the diffusion of the encapsulated drug. Such crosslinking chemistry is well known in the art and includes such methods described in detail in United States patent application publication number US20060240092, the entirety of which is hereby incorporated herein by reference. Such encapsulated small molecule drugs can be released in a controlled fashion over longer time periods compared to release by diffusion alone. In certain embodiments, the encapsulated small molecule drug is a member of the taxane family of anti-tubulin agents. In other embodiments, the encapsulated small molecule drug is paclitaxel. In still other embodiments, the encapsulated small molecule drug is docetaxel.

Small molecule drugs suitable as $R^1$, $R^2$, and $R^4$ groups of the present compounds include, but are not limited to, those having a functional group, or can be modified to include a functional group, suitable for covalently linking to one or more hydroxyl groups incorporated onto the metal substrate. As described herein, such drugs can be linked directly or via a hydrolytically cleavable linker. Such drugs include, without limitation, chemotherapeutic agents or other anti-proliferative agents including alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), angiogenesis inhibitors (Avastin) and hormones (Tamoxifen, Leuprolide, Flutamide, and Megestrol), Gleevec, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In other embodiments, the chemotherapeutic agent is Exemestance (aromasin), Camptosar (irinotecan), Ellence (epirubicin), Femara (Letrozole), Gleevac (imatinib mesylate), Lentaron (formestane), Cytadren/Orimeten (aminoglutethimide), Temodar, Proscar (finasteride), Viadur (leuprolide), Nexavar (Sorafenib), Kytril (Granisetron), Taxotere (Docetaxel), Taxol (paclitaxel), Kytril (Granisetron), Vesanoid (tretinoin) (retin A), XELODA (Capecitabine), Arimidex (Anastrozole), Casodex/Cosudex (Bicalutamide), Faslodex (Fulvestrant), Iressa (Gefitinib), Nolvadex, Istubal, Valodex (tamoxifen citrate), Tomudex (Raltitrexed), Zoladex (goserelin acetate), Leustatin (Cladribine), Velcade (bortezomib), Mylotarg (gemtuzumab ozogamicin), Alimta (pemetrexed), Gemzar (gemcitabine hydrochloride), Rituxan (rituximab), Revlimid (lenalidomide), Thalomid (thalidomide), Alkeran (melphalan), and derivatives thereof.

Other exemplary small molecule drugs include analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opiod analgesics, protease inhibitors, sex hormones, stimulants, muscle relaxants, anti-osteoporosis agents, anti-obesity agents, cognition enhancers, anti-urinary incontinence agents, anti-benign prostate hypertrophy agents, essential fatty acids, non-essential fatty acids, and mixtures thereof.

Other examples of small molecule drugs include treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In other embodiments, the $R^1$ group of formula I or the $R^4$ group of formula V is a small molecule blood-compatibilizing agent. Such blood-compatibilizing agents are well known in the art and include phosphorylcholine and phosphorylcholine derivatives.

It will also be appreciated that the $R^2$ group of formula II can be a small molecule blood-compatibilizing agent attached to the PEG via a hydrolytically stable linkage. In certain embodiments, the $R^2$ group is phosphorylchoine or a phosphorylcholine derivative.

Exemplary $R^1$ groups are set forth in Table 2, below.

TABLE 2

Representative $R^1$ Groups

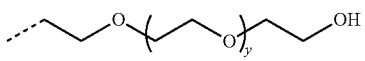

TABLE 2-continued
Representative R[1] Groups
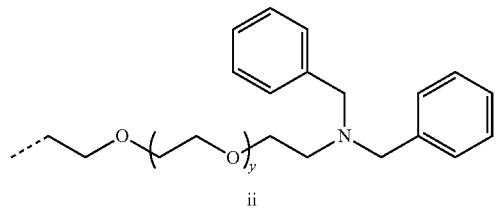
ii
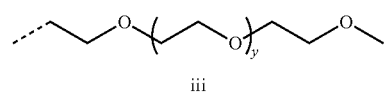
iii
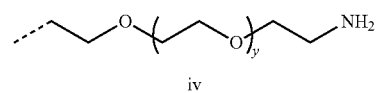
iv
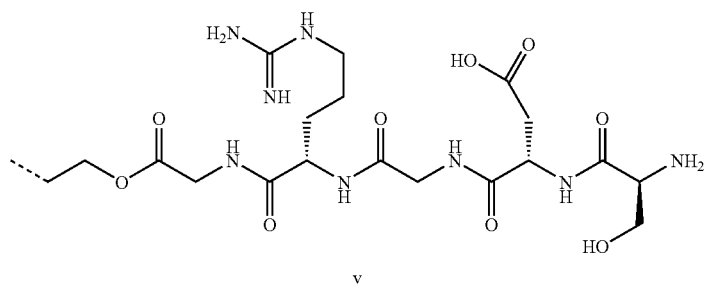
v
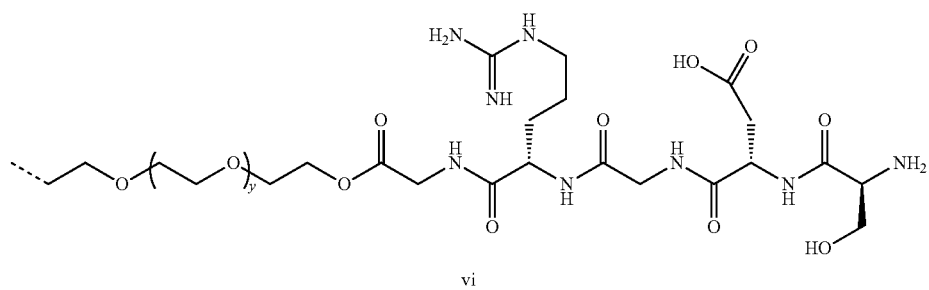
vi
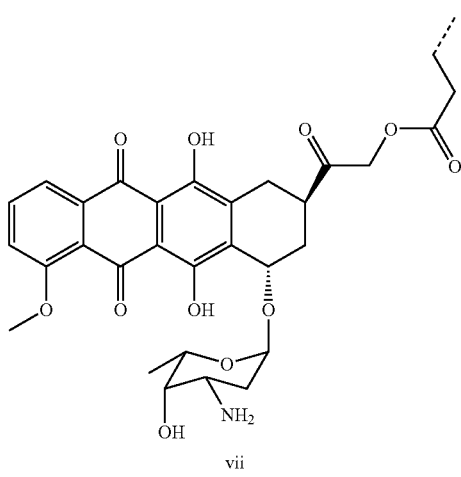
vii TABLE 2-continued
Representative R¹ Groups
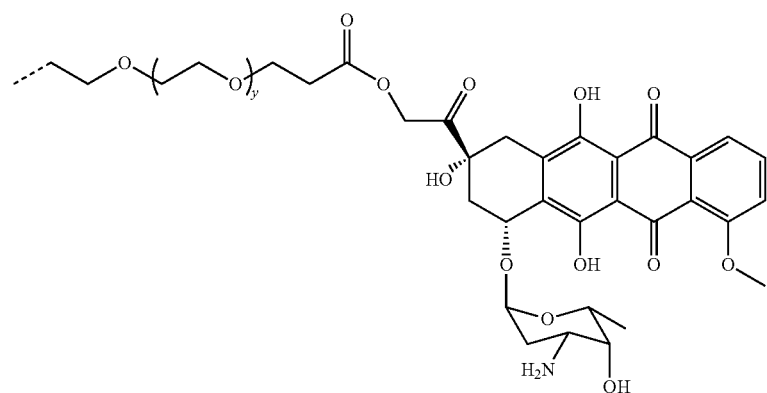
viii
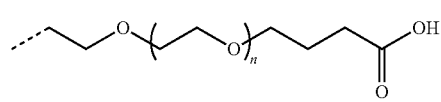
ix
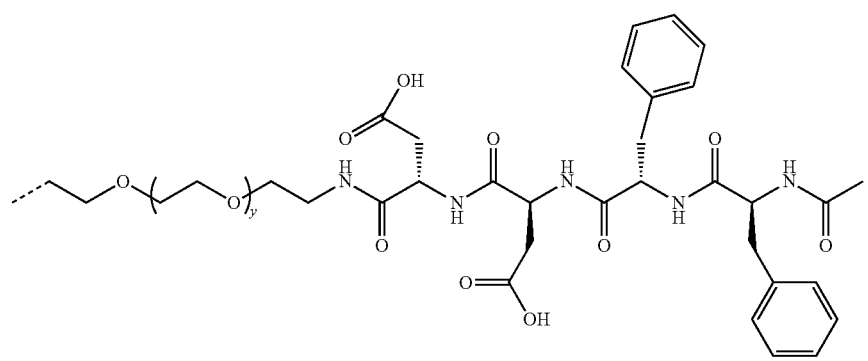
x
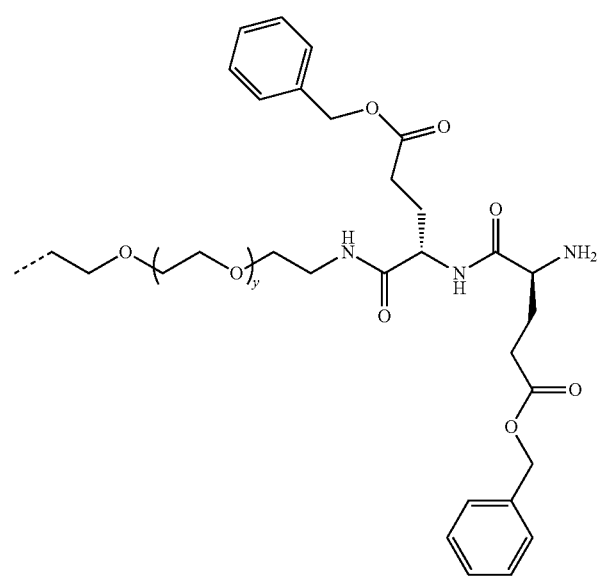
xi TABLE 2-continued
Representative R¹ Groups
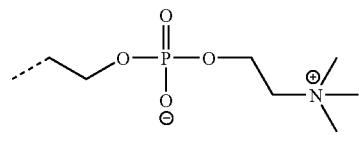
xii
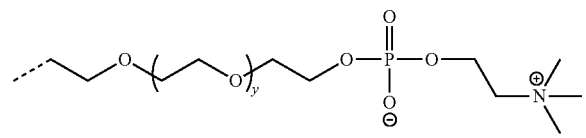
xiii
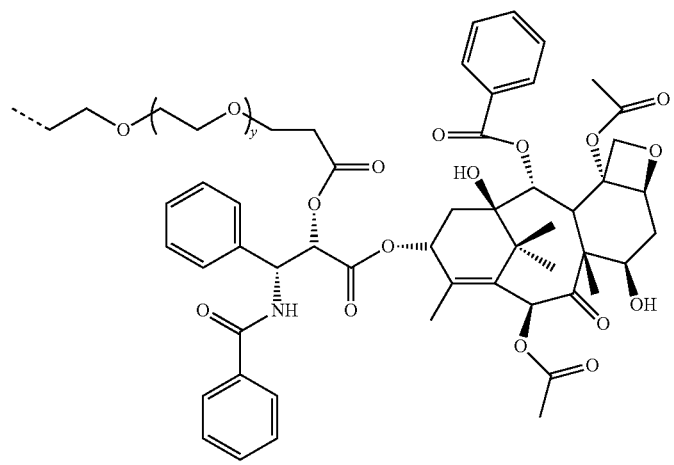
xiv
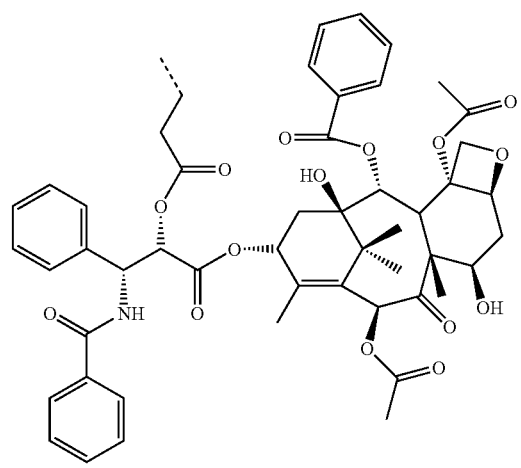
xv TABLE 2-continued
Representative R¹ Groups
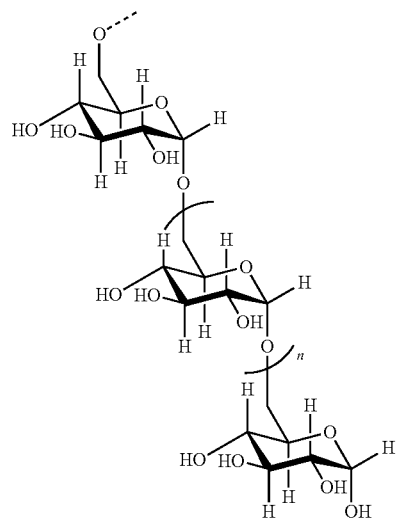
xvi
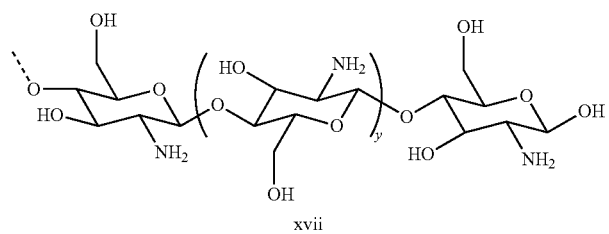
xvii
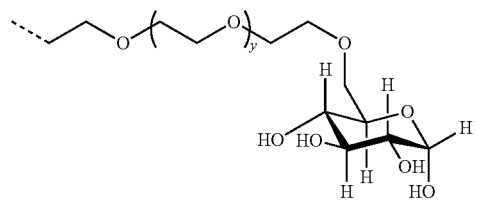
xviii
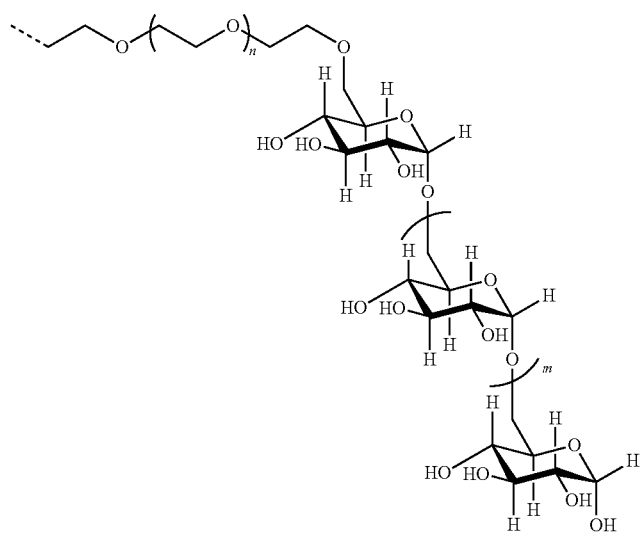
xix TABLE 2-continued
Representative R[1] Groups
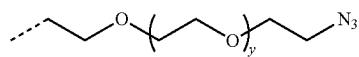
xx
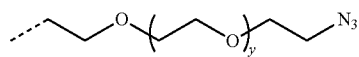
xxi
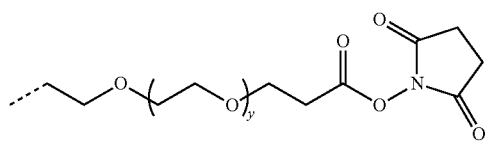
xxii
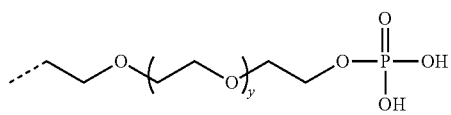
xxiii
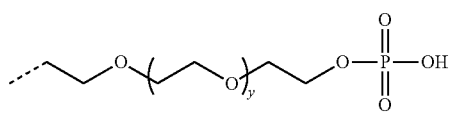
xxiv
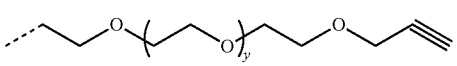
xxv
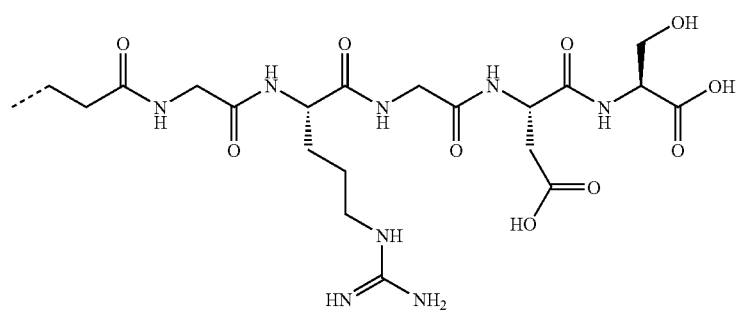
xxvi TABLE 2-continued
Representative R[1] Groups
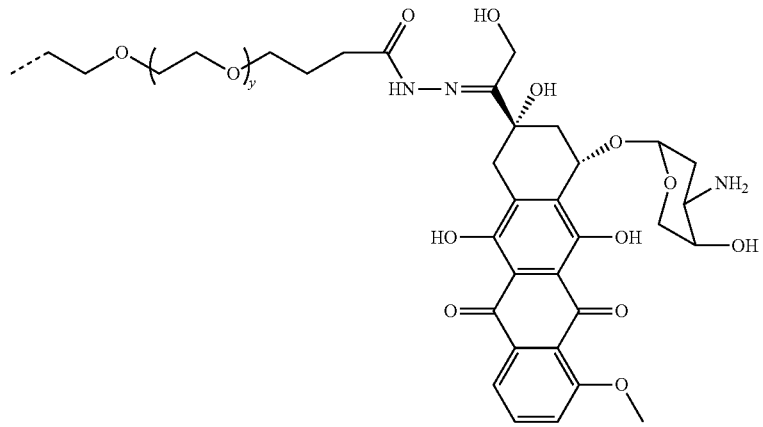
xxvii
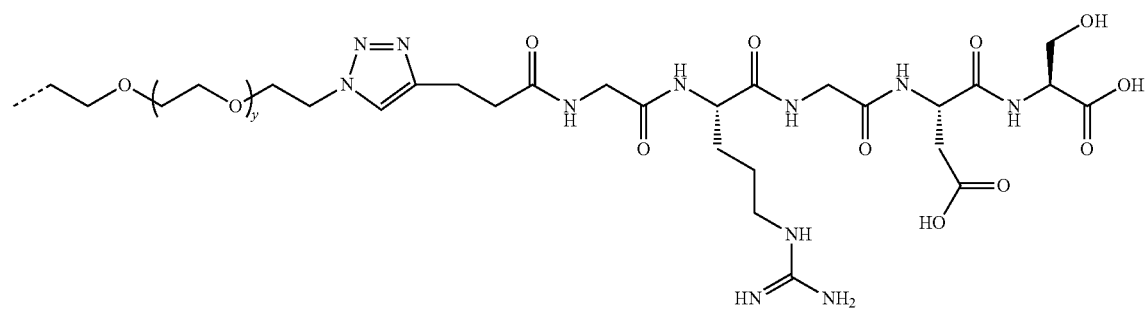
xxviii
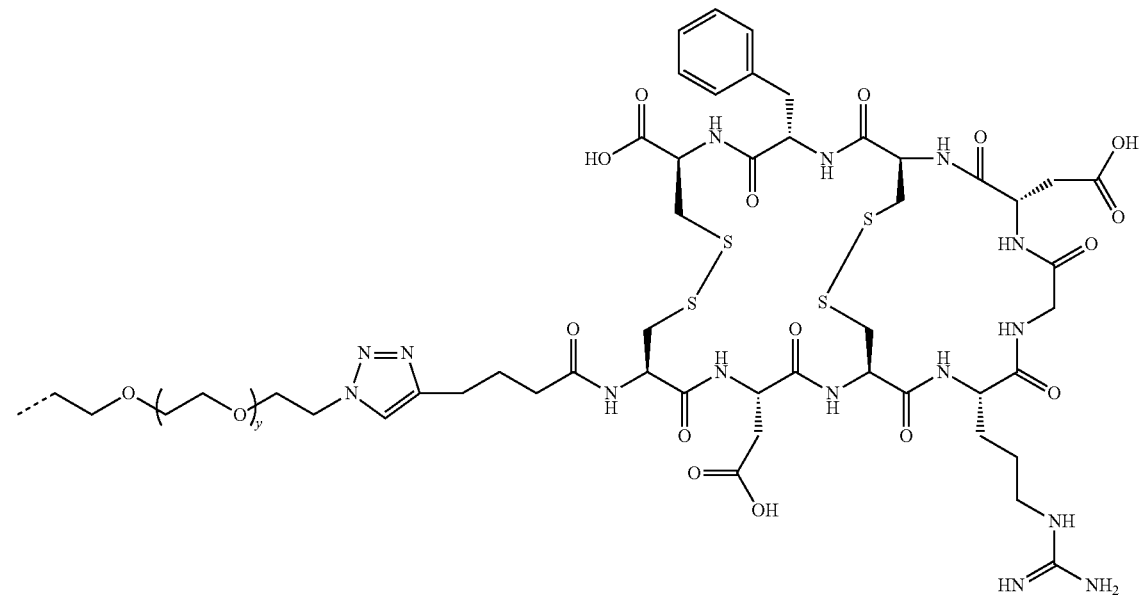
xxix TABLE 2-continued
Representative R¹ Groups
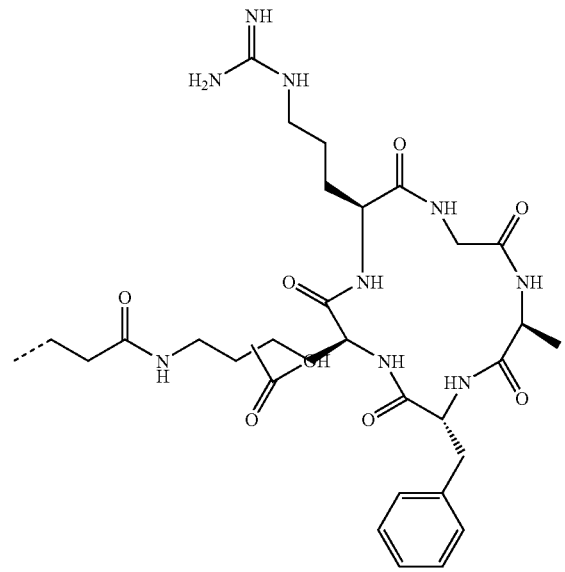
xxx
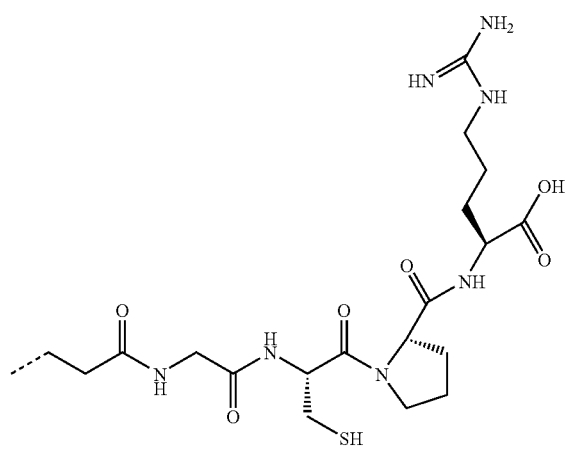
xxxi TABLE 2-continued
Representative R[1] Groups
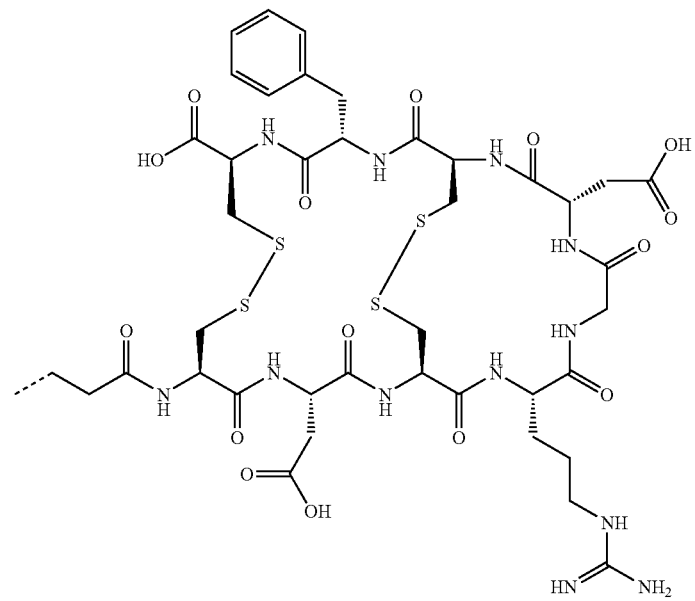
xxxii
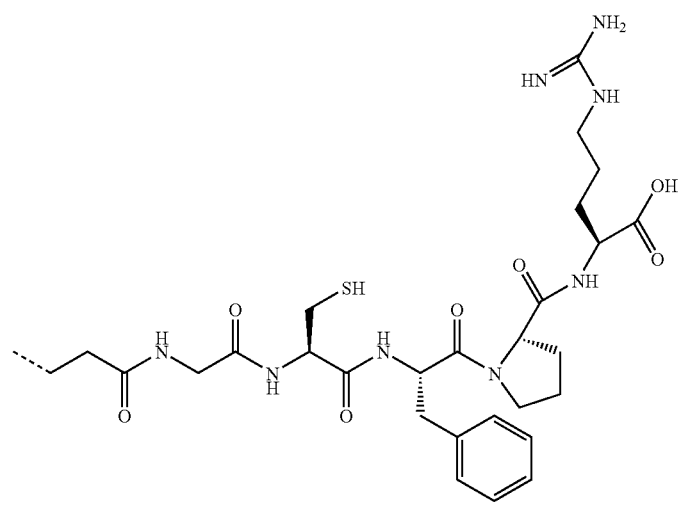
xxxiii TABLE 2-continued
Representative R¹ Groups
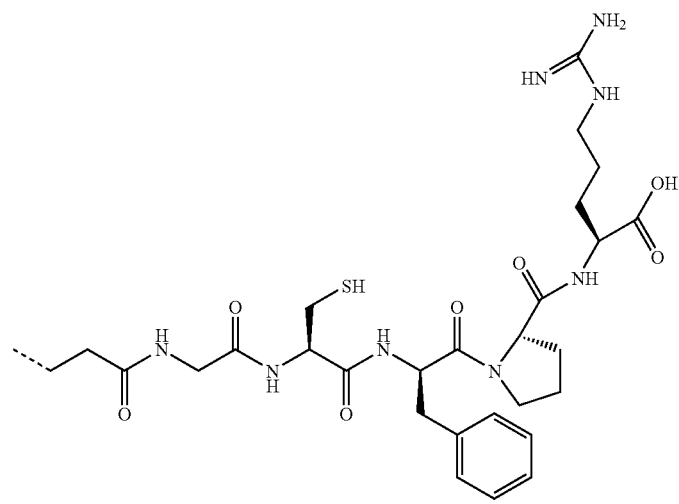
xxxiv
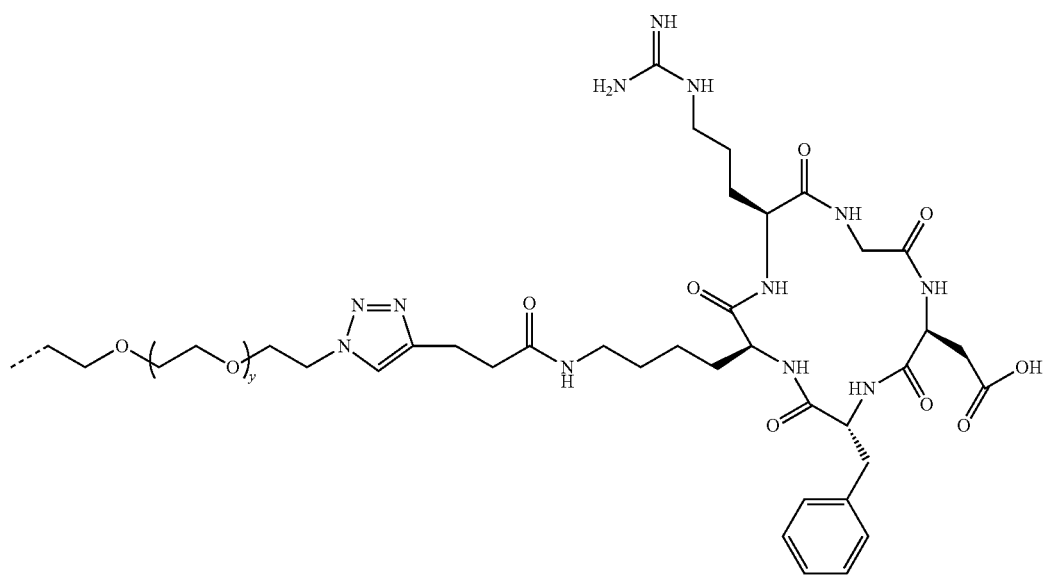
xxxv
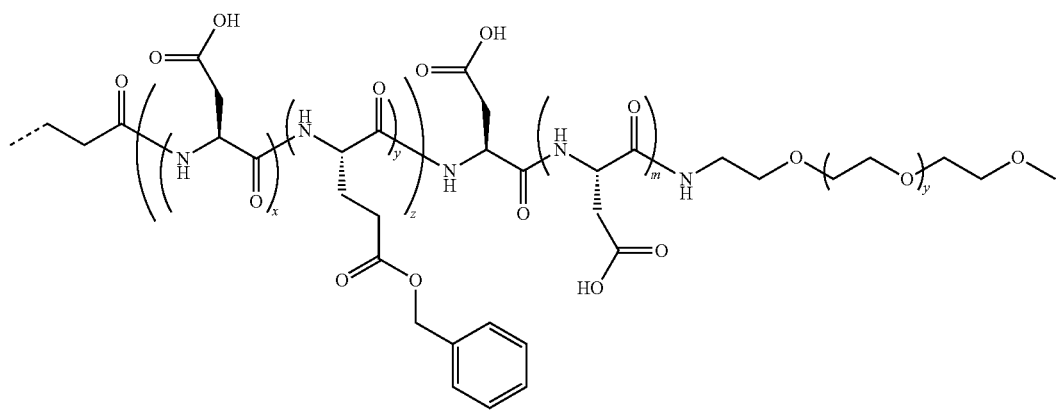
xxxvi TABLE 2-continued
Representative R¹ Groups
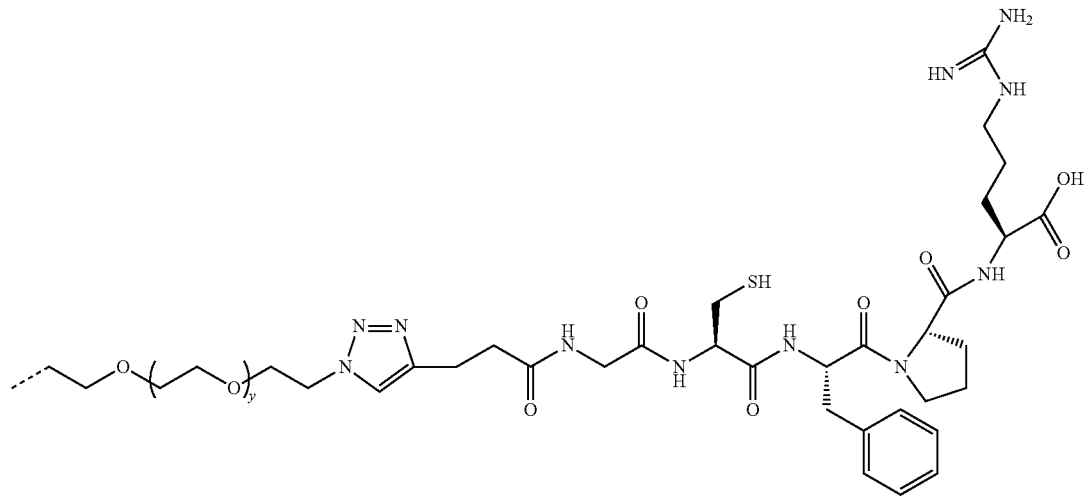
xxxvii
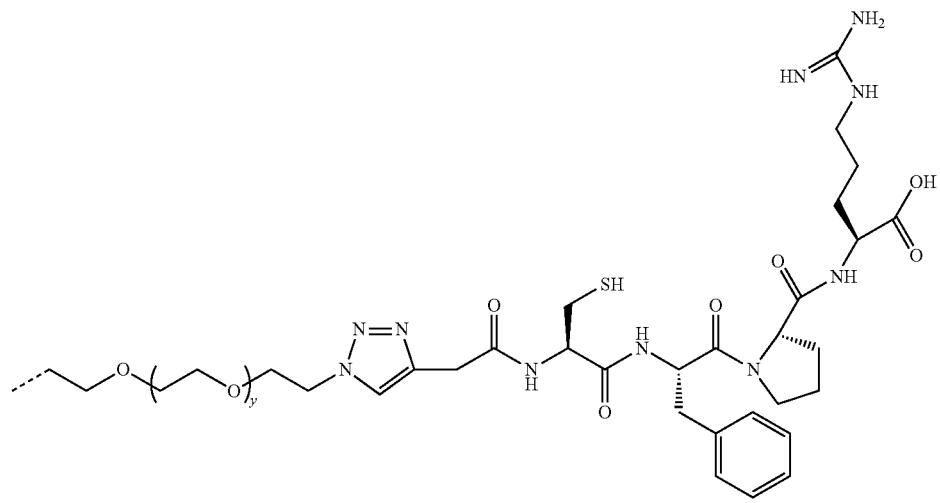
xxxviii TABLE 2-continued
Representative R[1] Groups
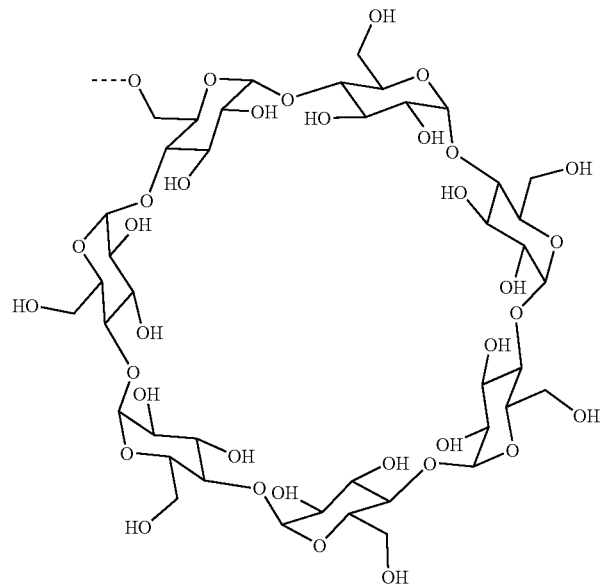
xxxix
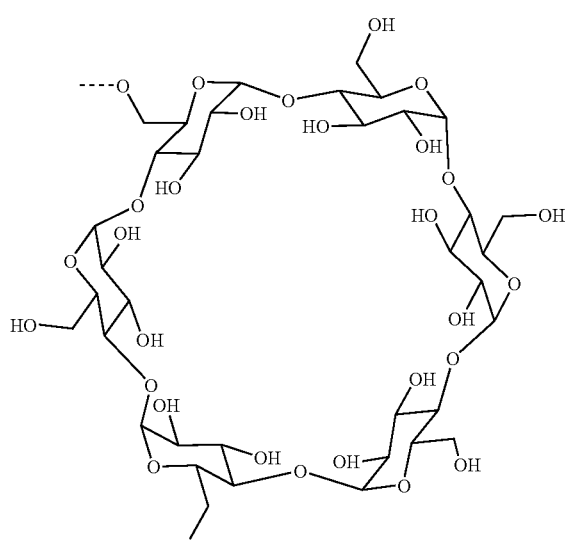
xxxx TABLE 2-continued
Representative R¹ Groups
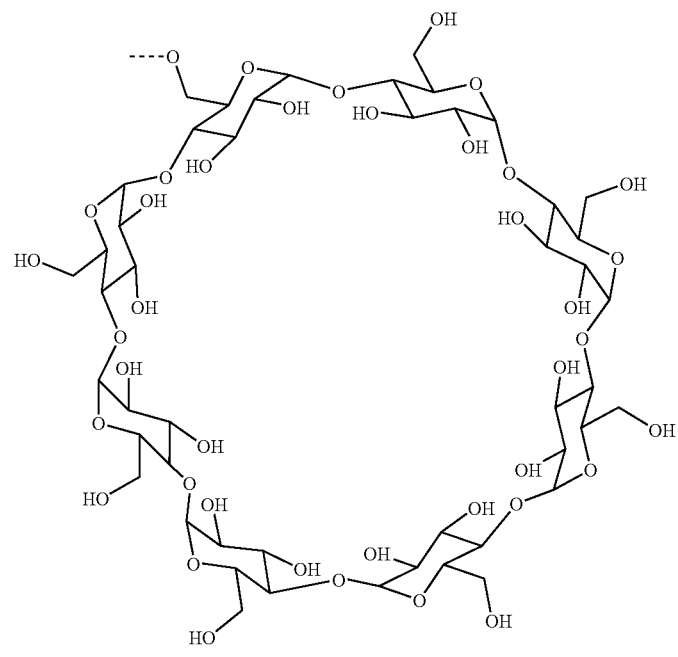
xxxxi
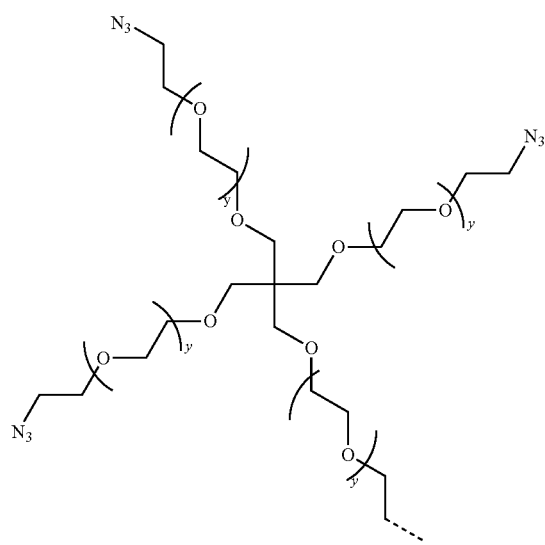
xxxxii TABLE 2-continued
Representative R[1] Groups
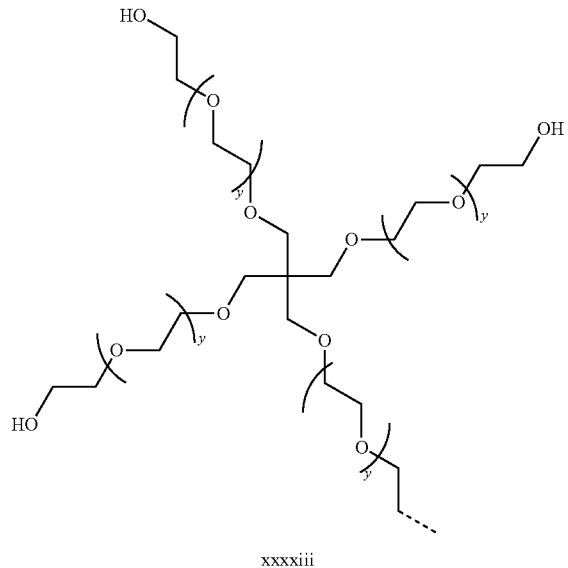
xxxxiii
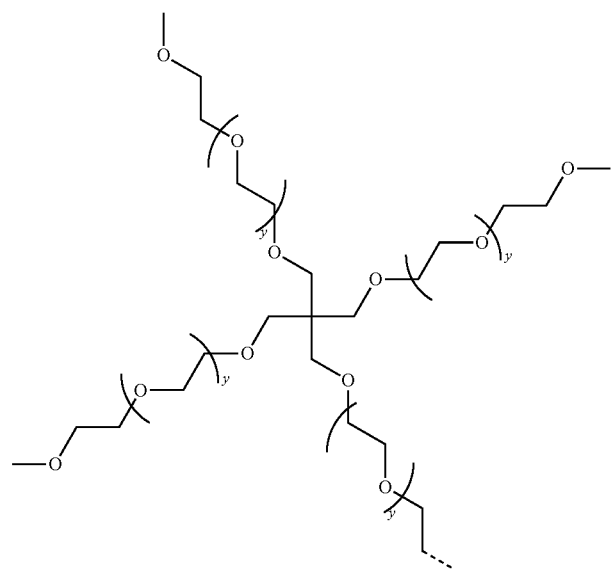
xxxxiv TABLE 2-continued
Representative R¹ Groups
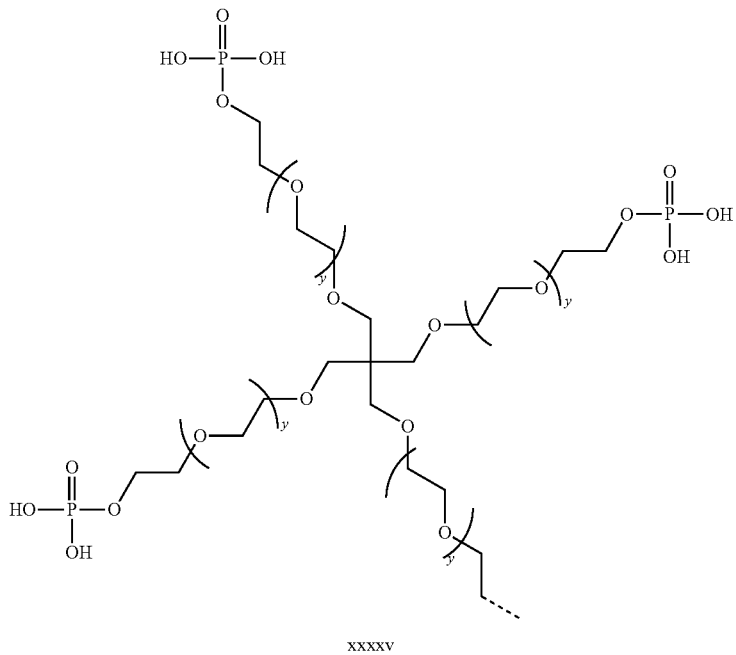
xxxxv
wherein each y, m, and m' is as defined above and described herein.
Additional exemplary R¹ groups are set forth in Table 3, below.
TABLE 3
Representative R¹ Groups
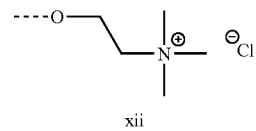
xii
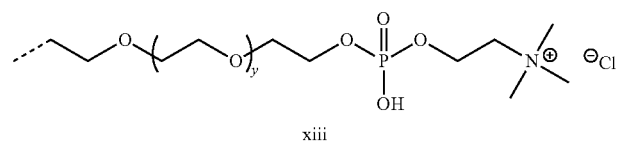
xiii TABLE 3-continued
Representative R[1] Groups
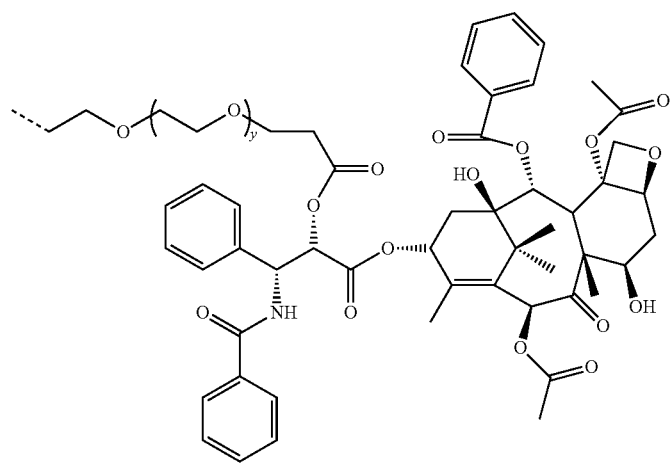
xiv
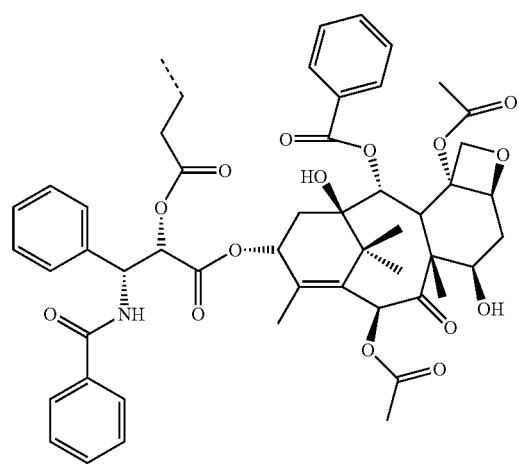
xv
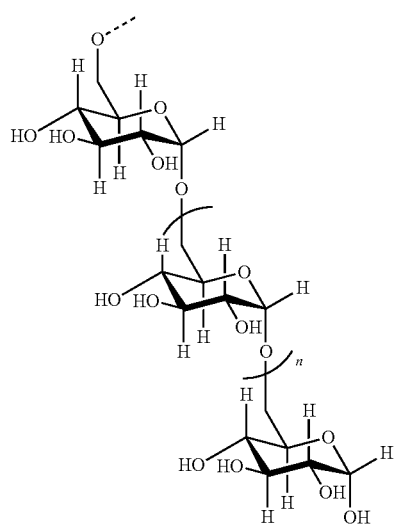
xvi TABLE 3-continued
Representative R[1] Groups
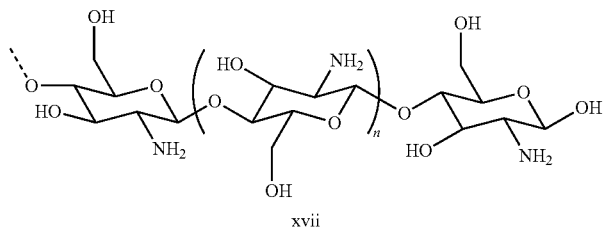
xvii
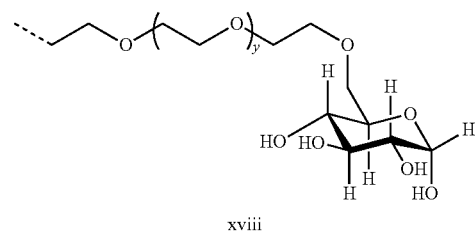
xviii
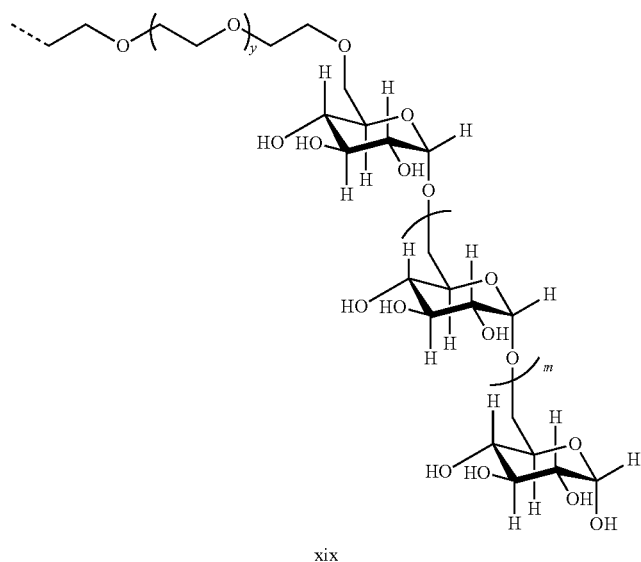
xix
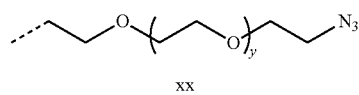
xx
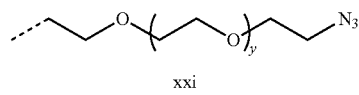
xxi
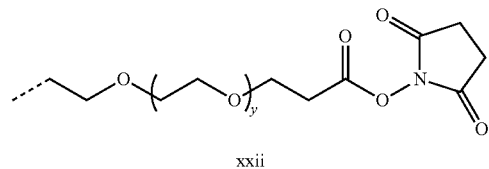
xxii
wherein each y is as defined above and described herein.

Exemplary $R^a$ groups are set forth in Table 4, below.

TABLE 4

Exemplary $R^a$ Groups

| a | b | c | d | e |

(a: phenyl; b: —CH$_3$; c: isopropyl-like branch; d: isobutyl-like branch; e: tert-butyl)

Exemplary $R^2$ groups are set forth in Table 5, below.

TABLE 5

Exemplary $R^2$ Groups a: alkyne (propargyl)
b: —CH$_2$CH$_2$—N$_3$
c: maleimide-ethyl
d: NHBoc-ethyl (tert-butyl carbamate)
e: 2-pyridyl disulfide-ethyl
f: biotin amide ethyl
g: methacrylamide-ethyl
h: 4-cyanophenyl
i: 3-oxopropyl (aldehyde)
j: NHS ester propanoate
k: tetrahydropyranyl ether ethyl
l: —CH$_2$CH$_2$—S—C(CH$_3$)$_3$
m

4. General Methods for Providing Compounds of the Present Invention

Multiblock copolymers of the present invention are prepared by methods known to one of ordinary skill in the art and those described in detail in U.S. patent application Ser. No. 11/325,020 filed Jan. 4, 2006, the entirety of which is hereby incorporated herein by reference. Generally, such multiblock copolymers are prepared by sequentially polymerizing one or more cyclic amino acid monomers onto a hydrophilic polymer having a terminal amine salt wherein said polymerization is initiated by said amine salt. In certain embodiments, said polymerization occurs by ring-opening polymerization of the cyclic amino acid monomers. In other embodiments, the cyclic amino acid monomer is an amino acid NCA, lactam, or imide.

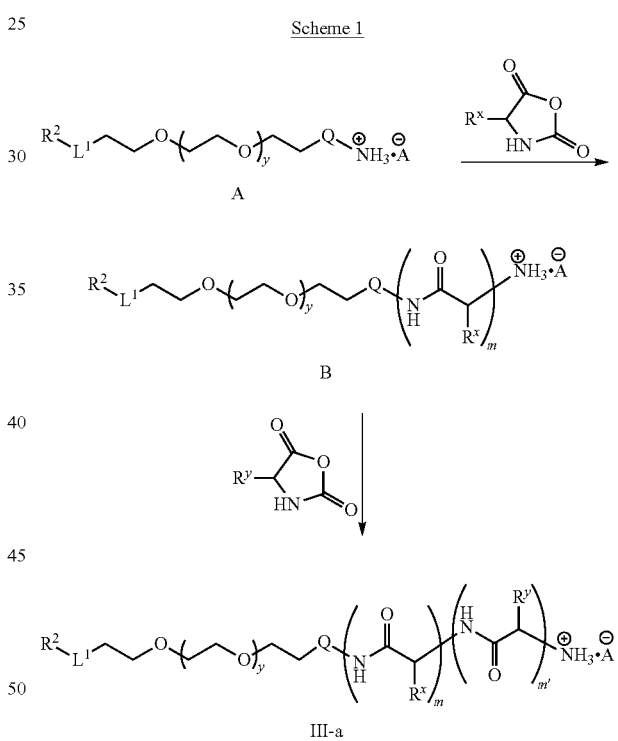

Scheme 1

Scheme 1 above depicts a general method for preparing multiblock polymers of the $R^1$ group of formula I of the present invention. A macroinitiator of formula A is treated with a first amino acid NCA to form a compound of formula B having a first amino acid block. The second amino acid NCA is added to the living polymer of formula B to form a compound of formula III-a having two differing amino acid blocks. Each of the $R^2$, $L^1$, A, y, Q, $R^x$, $R^y$, m, and m' groups depicted in Scheme 1 are as defined and described in classes and subclasses, singly and in combination, herein.

Scheme 2

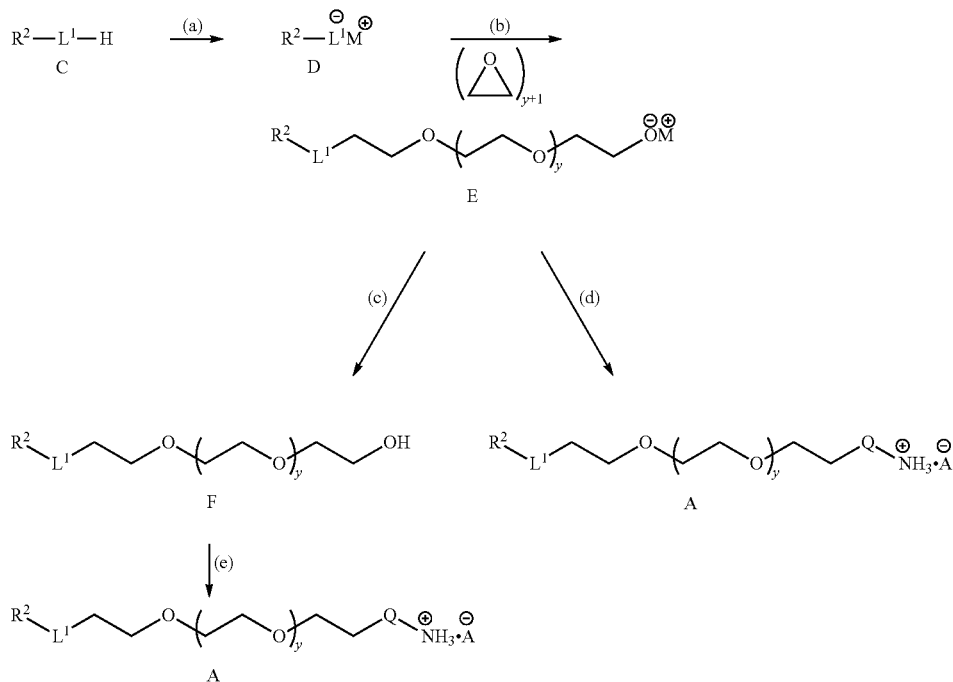

Scheme 2 above shows one exemplary method for preparing the bifunctional PEGs used to prepare the multiblock copolymers of the present invention. As described in United States patent application publication number US20060142506, suitably protected PEG-amines may be formed by terminating the living polymer chain end of a PEG with a terminating agent that contains a suitably protected amine. The suitably protected amine may then be deprotected to generate a PEG that is terminated with a free amine that may subsequently be converted into the corresponding PEG-amine salt macroinitiator. In certain embodiments, the PEG-amine salt macroinitiator of the present invention is prepared directly from a suitably protected PEG-amine by deprotecting said protected amine with an acid. Accordingly, in other embodiments, the terminating agent has suitably protected amino group wherein the protecting group is acid-labile.

Alternatively, suitable synthetic polymers having a terminal amine salt may be prepared from synthetic polymers that contain terminal functional groups that may be converted to amine salts by known synthetic routes. In certain embodiments, the conversion of the terminal functional groups to the amine salts is conducted in a single synthetic step. In other embodiments, the conversion of the terminal functional groups to the amine salts is achieved by way of a multi-step sequence. Functional group transformations that afford amines, amine salts, or protected amines are well known in the art and include those described in Larock, R. C., "Comprehensive Organic Transformations," John Wiley & Sons, New York, 1999.

At step (a), the polymerization initiator is treated with a suitable base to form D. A variety of bases are suitable for the reaction at step (a). Such bases include, but are not limited to, potassium naphthalenide, diphenylmethyl potassium, triphenylmethyl potassium, and potassium hydride. At step (b), the resulting anion is treated with ethylene oxide to form the polymer E. Polymer E can be transformed at step (d) to a compound of formula A directly by terminating the living polymer chain-end of E with a suitable polymerization terminator to afford a compound of formula A. Alternatively, polymer E may be quenched at step (c) to form the hydroxyl compound F. Compound F is then derivatized to afford a compound of formula A by methods known in the art, including those described herein. Each of the $R^2$, $L^1$, A, y, and Q groups depicted in Scheme 2 are as defined and described in classes and subclasses, singly and in combination, herein.

Although certain exemplary embodiments are depicted and described above and herein, it will be appreciated that compounds of the invention can be prepared according to the methods described generally above using appropriate starting materials by methods generally available to one of ordinary skill in the art. Additional embodiments are exemplified in more detail herein.

5. Uses

The modified metal surfaces in accordance with the present invention are useful for a multitude of uses. In certain embodiments, the covalently modified metal surfaces are useful in any application where metal is typically coated in a non-covalent fashion. Such applications include coated implantable medical devices. Such implantable devices include prostheses, artificial valves, vascular grafts, stents, catheters, and the like. These, and other such devices, are described in more detail below. In certain embodiments, the implantable device is a cardiovascular device, a neurosurgical device, a gastrointestinal device, a genitourinary device, a phthalmologic implant, an otolaryngology device, a plastic surgery implant, or an orthopedic implant.

Certain disorders are associated with the tissue trauma resulting from a medical procedure, such as angioplasty, or from the implantation of a medical device. For example, restenosis is a re-narrowing or blockage of an artery at the same site where treatment, such as an angioplasty or stent procedure, has already taken place. One cause of restenosis is tissue growth at the site of treatment characterized by a proliferation of the smooth muscle cells that normally line blood vessels.

Recent developments in the ongoing battle to reduce restenosis include the drug-eluting stent which has a medication coated on it to reduce the proliferation of cells that can cause restenosis. There is a continuing need to develop stents and other implantable devices coated with anti-proliferative agents advantageous for treating or preventing disorders associated with tissue trauma caused by implantable devices.

According to another aspect, the present invention provides a method for treating or preventing disorders associated with tissue trauma caused by implantable devices wherein said method comprises providing an implantable device, wherein at least a portion of said implantable device is a covalently modified metal surface in accordance with the present invention, and implanting said device in a patient. Said method is useful for treating or preventing, for example, restenosis of blood vessels subject to traumas such as angioplasty and stenting.

In other embodiments, the present invention provides an implantable device, wherein at least a portion of said device is a covalently modified metal surface. In still other embodiments, the present invention provides a PEGylated implantable device, wherein at least a portion of said device is a metal surface comprising PEG covalently bonded thereto.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a composition comprising an anti-proliferative compound. Such coatings and the general preparation of coated implantable devices are described in U.S. Pat. Nos. 6,099,562; 5,886, 026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. However, none of these coatings is covalently bonded to the device.

As described generally herein, one method of treating restenosis is to coat an implantable device with an anti-proliferative compound. Although the present invention contemplates covalently modified metal surfaces which incorporate small molecule drugs, one of ordinary skill in the art will appreciate that the present invention also contemplates covalently modified metal surfaces which do not incorporate small molecule drugs. Without wishing to be bound by any particular theory, it is believed that the "stealth" properties of PEG are particularly suited for implantable devices having at least a portion which is a metal surface covalently modified with PEG or a functionalized PEG. It is believed that the PEG itself will not induce restenosis, or other tissue injury caused by an implantable device, thereby negating the need for incorporation of an anti-proliferative or other small molecule drug. Thus, the present invention also provides an implantable device covalently modified in accordance with the present invention. In certain embodiments, the implantable device is covalently modified by a functionalized PEG. In other embodiments, the implantable device is covalently modified by a functionalized PEG of formula II as defined above and in classes and subclasses described herein.

As discussed above, the present devices are useful for treating or preventing restenosis of blood vessels subject to traumas such as angioplasty and stenting. For example, it is contemplated that such implanted medical devices include as tubings, shunts, catheters, artificial implants, pins, electrical implants such as pacemakers, and especially for arterial or venous stents, including balloon-expandable stents.

In certain embodiments, methods of the present invention are used for coating stents, or a metallic substrate to be made into a stent. A stent is typically an open tubular structure that has a pattern (or patterns) of apertures extending from the outer surface of the stent to the lumen. It is commonplace to make stents of biocompatible metallic materials, with the patterns cut on the surface with a laser machine. The stent can be electro-polished to minimize surface irregularities since these irregularities can trigger an adverse biological response. However, stents may still stimulate foreign body reactions that result in thrombosis or restenosis. To avoid these complications, a variety of stent coatings and compositions have been proposed to reduce the incidence of these complications or other complications and restore tissue function by itself or by delivering therapeutic compound to the lumen. For example, compounds having antiproliferative and anti-inflammatory activities have been evaluated as stent coatings, and have shown promise in preventing restenosis (See, for example, Presbitero P. et al., "Drug eluting stents do they make the difference?", *Minerva Cardioangiol,* 2002, 50(5): 431-442; Ruygrok P. N. et al., "Rapamycin in cardiovascular medicine", *Intern. Med. J.,* 2003, 33(3):103-109; and Marx S. O. et al., "Bench to bedside: the development of rapamycin and its application to stent restenosis", *Circulation,* 2001, 10-4(8): 852-855).

In certain embodiments, the present invention provides a stent, having at least a portion which is a covalently modified metal surface, for insertion into an artery or vein following balloon angioplasty. According to one aspect, the present invention provides a method of inhibiting arterial restenosis or arterial occlusion following vascular trauma comprising insertion into a subject in need thereof, a stent, having at least a portion which is a covalently modified metal surface. In the practice of the method, the subject may be a coronary bypass, vascular surgery, organ transplant or coronary or any other arterial angioplasty patient, for example.

In another aspect, the invention encompasses implants and surgical or medical devices, including stents and grafts, having at least a portion which is a covalently modified metal surface. In certain embodiments, the devices include compounds which inhibit smooth muscle cell proliferation. Representative examples of implants and surgical or medical devices contemplated by the present invention include cardiovascular devices (e.g., implantable venous catheters, venous ports, tunneled venous catheters, chronic infusion lines or ports, including hepatic artery infusion catheters, pacemaker wires, implantable defibrillators); neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions); gastrointestinal devices (e.g., chronic indwelling catheters, feeding tubes, portosystemic shunts, shunts for ascites, peritoneal implants for drug delivery, peritoneal dialysis catheters, implantable meshes for hernias, suspensions or solid implants to prevent surgical adhesions, including meshes); genitourinary devices (e.g., uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, chronic indwelling catheters, bladder augmentations, or wraps or splints for vasovasostomy); otolaryngology devices (e.g., ossicular implants, Eustachian tube splints or stents for glue ear or chronic otitis as an alternative to transtempanic drains); and orthopedic implants (e.g., cemented orthopedic prostheses).

In other embodiments of the invention, the implant or device contemplated by the present invention provides a uniform, predictable, prolonged release of the therapeutic agent, or composition thereof, into the tissue surrounding the implant or device once it has been deployed. For vascular stents, in addition to the above properties, the composition should not render the stent thrombogenic (causing blood clots to form), or cause significant turbulence in blood flow (more than the stent itself would be expected to cause if it was uncoated). In certain embodiments, said therapeutic agent is an anti-proliferative compound. In still other embodiments, said therapeutic agent is Paclitaxel.

In the case of stents, a wide variety of stents may be covalently modified in accordance with the present invention including esophageal stents, gastrointestinal stents, vascular stents, biliary stents, colonic stents, pancreatic stents, ureteric and urethral stents, lacrimal stents, Eustachian tube stents, fallopian tube stents and tracheal/bronchial stents (See, for example, U.S. Pat. No. 6,515,016, the entire contents of which are incorporated herein by reference). Stents may be readily obtained from commercial sources, or constructed in accordance with well-known techniques. Representative examples of stents include those described in U.S. Pat. No. 4,768,523, entitled "Hydrogel Adhesive"; U.S. Pat. No. 4,776,337, entitled "Expandable Intraluminal Graft, and Method and Apparatus for Implanting and Expandable Intraluminal Graft"; U.S. Pat. No. 5,041,126 entitled "Endovascular Stent and Delivery System"; U.S. Pat. No. 5,052,998 entitled "Indwelling Stent and Method of Use"; U.S. Pat. No. 5,064,435 entitled "Self-Expanding Prosthesis Having Stable Axial Length"; U.S. Pat. No. 5,147,370, entitled "Nitinol Stent for Hollow Body Conduits"; U.S. Pat. No. 5,176,626, entitled "Indwelling Stent"; U.S. Pat. No. 6,344,028 entitled "Replenishable Stent and Delivery System"; and U.S. Pat. No. 5,328,471, entitled "Method and Apparatus for Treatment of Focal Disease in Hollow Tubular Organs and Other Tissue Lumens."

As discussed above, the stent covalently modified in accordance with the present invention may be used to eliminate a vascular obstruction and prevent restenosis or reduce the rate of restenosis. Within other aspects of the present invention, such stents are provided for expanding the lumen of a body passageway. Specifically, a stent having a generally tubular structure, and at least a portion which is covalently modified metal, may be inserted into the passageway, such that the passageway is expanded. In certain embodiments, the stent may be used to eliminate a biliary, gastrointestinal, esophageal, tracheal/bronchial, urethral or vascular obstruction.

In other embodiments, methods are provided for preventing restenosis, comprising inserting a stent into an obstructed blood vessel, the stent having a generally tubular structure, at least a portion of the surface of the structure being covalently modified in accordance with the present invention, such that the obstruction is eliminated and smooth muscle cell proliferation is prevented or inhibited.

Within other aspects of the present invention, methods are provided for expanding the lumen of a body passageway, comprising inserting a stent into the passageway, the stent having a generally tubular structure, at least a portion of the surface of the structure being covalently modified in accordance with the present invention, such that the passageway is expanded. In certain embodiments, the lumen of a body passageway is expanded in order to eliminate a biliary, gastrointestinal, esophageal, tracheal/bronchial, urethral and/or vascular obstruction.

In certain embodiments, methods are provided for eliminating biliary obstructions, comprising inserting a biliary stent into a biliary passageway, the stent having a generally tubular structure, at least a portion of the surface of the structure being covalently modified in accordance with the present invention, such that the biliary obstruction is eliminated. For example, tumor overgrowth of the common bile duct results in progressive cholestatic jaundice which is incompatible with life. Generally, the biliary system which drains bile from the liver into the duodenum is most often obstructed by (1) a tumor composed of bile duct cells (cholangiocarcinoma), (2) a tumor which invades the bile duct (e.g., pancreatic carcinoma), or (3) a tumor which exerts extrinsic pressure and compresses the bile duct (e.g., enlarged lymph nodes). Both primary biliary tumors, as well as other tumors which cause compression of the biliary tree may be treated utilizing stents, implants and other surgical or medical devices, at least a portion of which is metal which is covalently modified in accordance with the present invention.

One example of primary biliary tumors are adenocarcinomas (which are also called Klatskin tumors when found at the bifurcation of the common hepatic duct). These tumors are also referred to as biliary carcinomas, choledocholangiocarcinomas, or adenocarcinomas of the biliary system. Benign tumors which affect the bile duct (e.g., adenoma of the biliary system), and, in rare cases, squamous cell carcinomas of the bile duct and adenocarcinomas of the gallbladder, may also cause compression of the biliary tree and therefore, result in biliary obstruction. Compression of the biliary tree is most commonly due to tumors of the liver and pancreas which compress and therefore obstruct the ducts. Most of the tumors from the pancreas arise from cells of the pancreatic ducts. This is a highly fatal form of cancer (5% of all cancer deaths; 26,000 new cases per year in the U.S.) with an average of 6 months survival and a 1 year survival rate of only 10%. When these tumors are located in the head of the pancreas they frequently cause biliary obstruction, and this detracts significantly from the quality of life of the patient. While all types of pancreatic tumors are generally referred to as "carcinoma of the pancreas" there are histologic subtypes including: adenocarcinoma, adenosquamous carcinoma, cystadenocarcinoma, and acinar cell carcinoma. Hepatic tumors, as discussed above, may also cause compression of the biliary tree, and therefore cause obstruction of the biliary ducts.

A biliary stent is first inserted into a biliary passageway in one of several ways: from the top end by inserting a needle through the abdominal wall and through the liver (a percutaneous transhepatic cholangiogram or "PTC"); from the bottom end by cannulating the bile duct through an endoscope inserted through the mouth, stomach, and duodenum (an endoscopic retrograde cholangiogram or "ERCP"); or by direct incision during a surgical procedure. A preinsertion examination, PTC, ERCP, or direct visualization at the time of surgery is optionally performed to determine the appropriate position for stent insertion. A guidewire is then advanced through the lesion, and over this a delivery catheter is passed to allow the stent to be inserted in its collapsed form. If the diagnostic exam was a PTC, the guidewire and delivery catheter is inserted via the abdominal wall, while if the original exam was an ERCP the stent may be placed via the mouth. The stent is then positioned under radiologic, endoscopic, or direct visual control taking particular care to place it precisely across the narrowing in the bile duct. The delivery catheter is then removed leaving the stent standing as a scaffolding which holds the bile duct open. A further cholangiogram may be performed to document that the stent is appropriately positioned.

In certain embodiments, methods are provided for eliminating esophageal obstructions, comprising inserting an esophageal stent into an esophagus, the stent having a generally tubular structure, at least a portion of the surface of the structure being covalently modified in accordance with the present invention, such that the esophageal obstruction is eliminated. For example, the esophagus is the hollow tube which transports food and liquids from the mouth to the stomach. Cancer of the esophagus or invasion by cancer arising in adjacent organs (e.g., cancer of the stomach or lung) results in the inability to swallow food or saliva. In certain embodiments, a pre-insertion examination, usually a barium swallow or endoscopy is performed in order to determine the appropriate position for stent insertion. A catheter or endoscope may then be positioned through the mouth, and a guidewire is advanced through the blockage. A stent delivery catheter is passed over the guidewire under radiologic or endoscopic control, and a stent is placed precisely across the narrowing in the esophagus. A post-insertion examination, usually a barium swallow x-ray, may be utilized to confirm appropriate positioning.

In certain embodiments, methods are provided for eliminating colonic obstructions, comprising inserting a colonic stent into a colon, the stent having a generally tubular structure, at least a portion of the surface of the structure being covalently modified in accordance with the present invention, such that the colonic obstruction is eliminated. For example, the colon is the hollow tube which transports digested food and waste materials from the small intestines to the anus. Cancer of the rectum and/or colon or invasion by cancer arising in adjacent organs (e.g., cancer of the uterus, ovary, bladder) results in the inability to eliminate feces from the bowel. In certain embodiments, a pre-insertion examination, usually a barium enema or colonoscopy is performed in order to determine the appropriate position for stent insertion. A catheter or endoscope may then be positioned through the anus, and a guidewire is advanced through the blockage. A stent delivery catheter is passed over the guidewire under radiologic or endoscopic control, and a stent is placed precisely across the narrowing in the colon or rectum. A post-insertion examination, usually a barium enema x-ray, may be utilized to confirm appropriate positioning.

In certain embodiments, methods are provided for eliminating tracheal/bronchial obstructions, comprising inserting a tracheal/bronchial stent into a trachea or bronchi, the stent having a generally tubular structure, at least a portion of the surface of the structure being covalently modified in accordance with the present invention, such that the tracheal/bronchial obstruction is eliminated. For example, the trachea and bronchi are tubes which carry air from the mouth and nose to the lungs. Blockage of the trachea by cancer, invasion by cancer arising in adjacent organs (e.g., cancer of the lung), or collapse of the trachea or bronchi due to chondromalacia (weakening of the cartilage rings) results in inability to breathe. In certain embodiments, a pre-insertion examination, usually an endoscopy, is performed in order to determine the appropriate position for stent insertion. A catheter or endoscope is then positioned through the mouth, and a guidewire advanced through the blockage. A delivery catheter is then passed over the guidewire in order to allow a collapsed stent to be inserted. The stent is placed under radiologic or endoscopic control in order to place it precisely across the narrowing. The delivery catheter may then be removed leaving the stent standing as a scaffold on its own. A post-insertion examination, usually a bronchoscopy may be utilized to confirm appropriate positioning.

In certain embodiments, methods are provided for eliminating urethral obstructions, comprising inserting a urethral stent into a urethra, the stent having a generally tubular structure, at least a portion of the surface of the structure being covalently modified in accordance with the present invention, such that the urethral obstruction is eliminated. For example, the urethra is the tube which drains the bladder through the penis. Extrinsic narrowing of the urethra as it passes through the prostate, due to hypertrophy of the prostate, occurs in virtually every man over the age of 60 and causes progressive difficulty with urination. In certain embodiments, a pre-insertion examination, usually an endoscopy or urethrogram is first performed in order to determine the appropriate position for stent insertion, which is above the external urinary sphincter at the lower end, and close to flush with the bladder neck at the upper end. An endoscope or catheter is then positioned through the penile opening and a guidewire advanced into the bladder. A delivery catheter is then passed over the guidewire in order to allow stent insertion. The delivery catheter is then removed, and the stent expanded into place. A post-insertion examination, usually endoscopy or retrograde urethrogram, may be utilized to confirm appropriate position.

In certain embodiments, methods are provided for eliminating vascular obstructions, comprising inserting a vascular stent into a blood vessel, the stent having a generally tubular structure, at least a portion of the surface of the structure being covalently modified in accordance with the present invention, such that the vascular obstruction is eliminated. For example, stents may be placed in a wide array of blood vessels, both arteries and veins, to prevent recurrent stenosis at the site of failed angioplasties, to treat narrowings that would likely fail if treated with angioplasty, and to treat post-surgical narrowings (e.g., dialysis graft stenosis). Suitable sites include, but are not limited to, the iliac, renal, and coronary arteries, the superior vena cava, and in dialysis grafts. In certain embodiments, angiography is first performed in order to localize the site for placement of the stent. This is typically accomplished by injecting radiopaque contrast through a catheter inserted into an artery or vein as an x-ray is taken. A catheter may then be inserted either percutaneously or by surgery into the femoral artery, brachial artery, femoral vein, or brachial vein, and advanced into the appropriate blood vessel by steering it through the vascular system under fluoroscopic guidance. A stent may then be positioned across the vascular stenosis. A post-insertion angiogram may also be utilized in order to confirm appropriate positioning.

Compositions comprising one or more therapeutic agents can be coated on a device according to the present invention, which is then implanted to provide localized delivery of the therapeutic agent or agents contained therein. In certain embodiments, said therapeutic agent is an anti-proliferative compound. In still other embodiments, said therapeutic agent is Paclitaxel. General methods for delivering the therapeutic agent or agents contained within the coating on said device to targeted areas of the body have been described, for example, in U.S. Pat. No. 5,651,986. Such localized delivery is useful for, among other things, inhibiting the growth of a tumor. This method avoids the systemic levels of the chemotherapeutic agent or agents often associated with toxicity. The localized delivery of the therapeutic agent is achieved by implanting a device, coated with a composition of the present invention, proximally to the tumor. The therapeutic agent is typically released from the device by diffusion, degradation of the matrix, or a combination thereof. Thus, another aspect of the present invention relates to a method for inhibiting growth of a tumor, in a patient in need thereof, comprising implanting a device, coated with a composition as described herein, for administering localized delivery of the therapeutic agent.

EXAMPLES

Preparation of Bifunctional Pegs and Multiblock Copolymers of the Present Invention As described generally above, multiblock copolymers of the present invention are prepared using the heterobifunctional PEGs described herein and in United States patent application publication number US20060142506, the entirety of which is hereby incorporated herein by reference. The preparation of multiblock polymers in accordance with the present invention is accomplished by methods known in the art, including those described in detail in United States patent application publication number US20060172914, the entirety of which is hereby incorporated herein by reference.

Example 1

A coupon of 316 stainless steel is placed in an oxidation reactor and treated with a $1.3 \times 10^{16}$ m$^{-3}$ and 3 eV water vapor plasma at 100° C. for a period of 24 hours. The metal substrate is placed in an aqueous solution containing 5 wt % phosphonic acid functionalized poly(ethylene glycol) for one hour. The substrate is removed from the PEG solution and dried under vacuum at 160° C. for 24 hours to give the desired PEG-functionalized stainless steel. See FIG. 11.

Example 2

A ½"×½"×⅛" 316 L stainless steel coupon was cleaned with an argon plasma process (250 mtorr Ar$_2$, 100° C., 4000 watts for 15 minutes at a flow of 2.5 slm). The freshly cleaned coupon was then exposed to an oxygen plasma treatment (250 mtorr O$_2$, 100° C., 4000 watts for 15 minutes flow of 2.5 slm). Contact angle was found to be 8°.

Example 3

A coupon of 316 stainless steel is placed in an oxidation reactor and treated with a $1.3 \times 10^{16}$ m$^{-3}$ and 3 eV water vapor plasma at 100° C. for a period of 24 hours. The metal substrate is placed in a vacuum flask and the system evacuated. The flask is backfilled with Argon and an anhydrous solution containing 5 wt % phosphonic chloride functionalized poly(ethylene glycol) in tetrahydrofuran is added. After sixteen hours, the substrate is removed from the PEG solution and dried under vacuum at 60° C. for 24 hours to give the desired PEG-functionalized stainless steel. See FIG. 12.

Example 4

An oxygen plasma treated coupon was placed in an aqueous solution containing 10 wt % THP-PEG-Phosphonic acid (5,000 g/mol). The coupon was allowed to remain in the PEG solution for 2 hours at which point it was removed for the PEG solution and placed in a pyrex dish. The coupon was heated to 160° C. under vacuum for 12 hours. The coupon was allowed to cool to room temperature at which point is was washed with methylene chloride and acetone and subsequently dried with a paper towel. Contact angle was found to be 18°.

Example 5

An oxygen plasma treated coupon was placed in an aqueous solution containing 10 wt % dibenzylamine-PEG-Phosphonic acid (8,000 g/mol). The coupon was allowed to remain in the PEG solution for 2 hours at which point it was removed for the PEG solution and placed in a pyrex dish. The coupon was heated to 160° C. under vacuum for 12 hours. The coupon was allowed to cool to room temperature at which point is was washed with methylene chloride and acetone and subsequently dried with a paper towel. Contact angle was found to be 49°.

We claim:
1. A method for preparing a covalently modified metal surface, comprising the steps of:
 (a) modifying a metal substrate to incorporate thereon a plurality of hydroxyl groups;
 (b) providing a compound of formula I:

wherein:
 R$^1$ is synthetic polymer group selected from poly(ethylene glycol) (PEG), a heterobifunctional PEG, or a branched PEG;
 W is —C(=O)OH, —C(=O)X, —P(=O)(OH)$_2$, —P(=O)(X)$_2$, —P(=O)(R$^a$)OH, —P(=O)(R$^a$)X, —O—S(=O)$_2$OH, —S(=O)$_2$OH, —Si(R$^a$)$_2$OH, —Si(OR$^a$)$_2$OH, —Si(R$^a$)$_2$X, —Si(R$^a$)(OH)$_2$, —Si(R$^a$)X$_2$, —Si(OR$^a$)$_2$X, C(=O)H, —N=C=S, —N=C=O, phenol, thiophenol, or an epoxide;
 each X is independently Cl, Br, or I; and
 each R$^a$ is hydrogen, an alkyl group, or an aryl group; and
 (c) coupling the compound of formula I directly to one or more of the hydroxyl groups on the metal surface via the W moiety.

2. The method according to claim 1, wherein the metal substrate comprises iron.

3. The method according to claim 1, wherein the metal substrate is selected from a stainless steel, a cobalt alloy, a titanium alloy, an iron alloy, steel, stainless steel, austenitic stainless steel, Type 316 stainless steel, ferritic stainless steel, martensitic stainless steel, duplex stainless steel, cobalt, a cobalt alloy, a cobalt-chromium alloy, stellite alloys, titanium, titanium alloy, or a super-alloy.

4. The method according to claim 1, wherein step (c) is performed by condensation or dehydration reaction.

5. A method for preparing a covalently modified metal surface, comprising the steps of:
 (a) providing a metal surface having a plurality of hydroxyl groups;
 (b) providing a compound of formula I:

wherein:
 R$^1$ is a synthetic polymer group selected from poly(ethylene glycol) (PEG), a heterobifunctional PEG, or a branched PEG;
 W is —C(=O)OH, —C(=O)X, —P(=O)(OH)$_2$, —P(=O)(X)$_2$, —P(=O)(R$^a$)OH, —P(=O)(R$^a$)X, —O—S(=O)$_2$OH, —S(=O)$_2$OH, —Si(R$^a$)$_2$OH, —Si(OR$^a$)$_2$OH, —Si(R$^a$)$_2$X, —Si(R$^a$)(OH)$_2$, —Si(R$^a$)X$_2$, —Si(OR$^a$)$_2$X, C(=O)H, —N=C=S, —N=C=O, phenol, thiophenol, or an epoxide;
 each X is independently Cl, Br, or I; and
 each R$^a$ is hydrogen, an alkyl group, or an aryl group;

and (c) coupling the compound of formula I to one or more of the hydroxyl groups on the metal surface via the W moiety.

6. The method according to claim 5, wherein $R^1$ is a group of formula II:

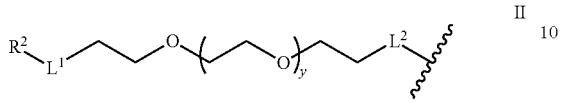

or a salt thereof, wherein:
y is 0-2500;
$R^2$ is hydrogen, halogen, $NO_2$, CN, $N_3$, —N=C=O, —C(R)=NN(R)$_2$, —P(O)(OR)$_2$, —P(O)(X')$_2$, a 9-30 membered crown ether, a mono-protected amine, a di-protected amine, a protected aldehyde, a protected hydroxyl, a protected carboxylic acid, a protected thiol, or an optionally substituted group selected from aliphatic, a 3-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
each X' is independently halogen;
each R is independently hydrogen or an optionally substituted aliphatic group;
$L^1$ is a valence bond or a bivalent, saturated or unsaturated, straight or branched $C_{1-12}$ alkylene chain, wherein 0-6 methylene units of $L^1$ are independently replaced by -Cy-, —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)—, wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and
$L^2$ is a valence bond or a bivalent, saturated or unsaturated, straight or branched $C_{1-12}$ alkylene chain, wherein 0-6 methylene units of $L^2$ are independently replaced by -Cy-, —O—, —NR—, —S—, or —C(O)—, wherein:
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

7. The method according to claim 6, wherein $R^1$ is a group of formula II-d:

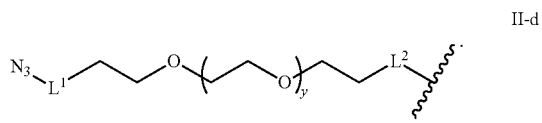

8. The method according to claim 6, further comprising the step of coupling the azide-terminal end to a suitable group via Click chemistry.

9. The method according to claim 5 wherein $R^1$ is selected from any of the following groups:

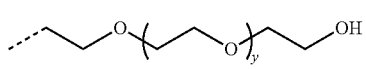

i

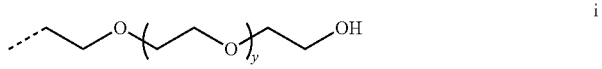

ii

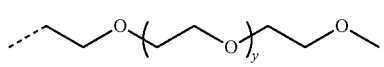

iii

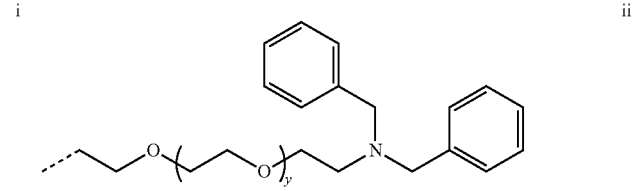

iv

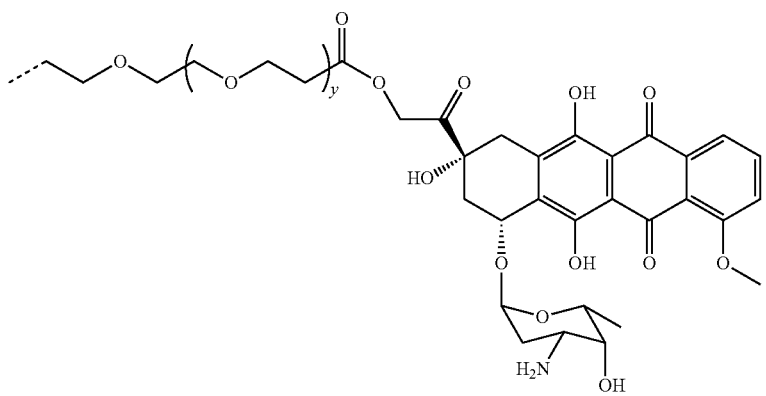

viii

-continued
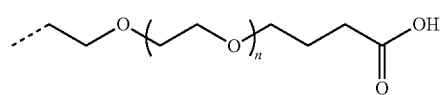 ix
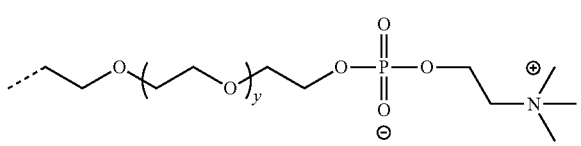 xiii
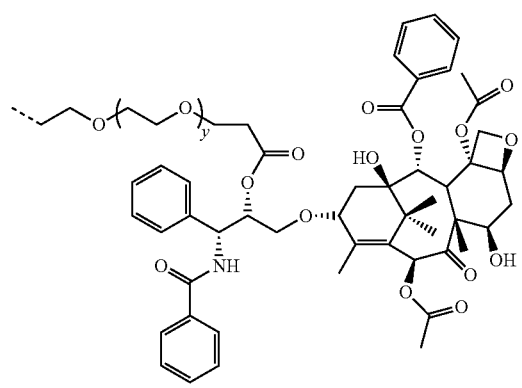 xiv
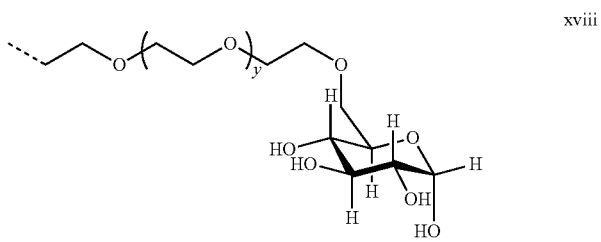 xviii
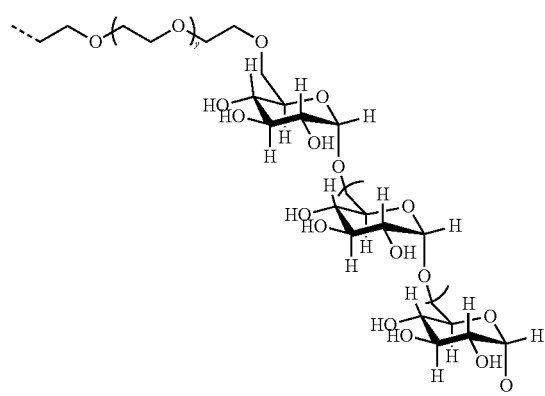 xix
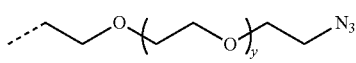 xx
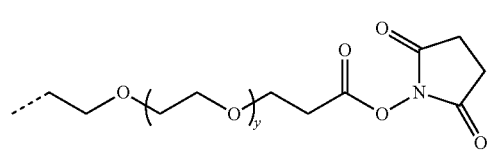 xxii
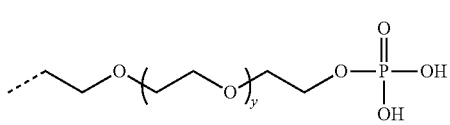 xxiii
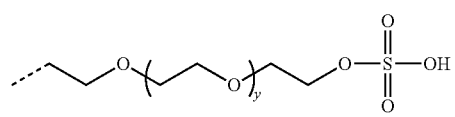 xxiv
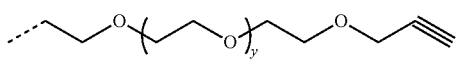 xxv xxvii
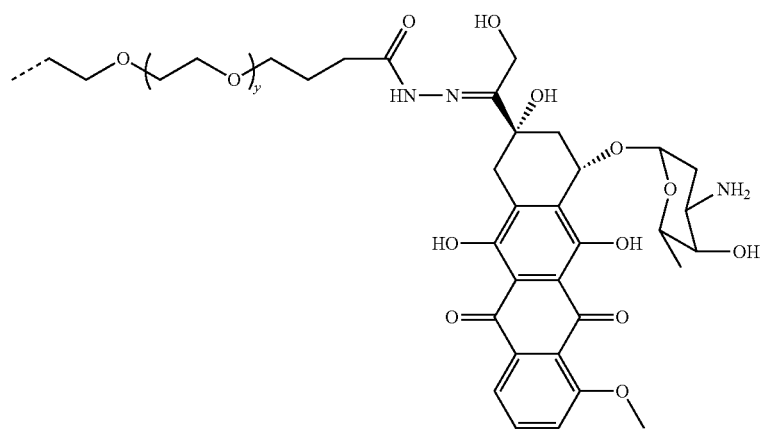
xxix
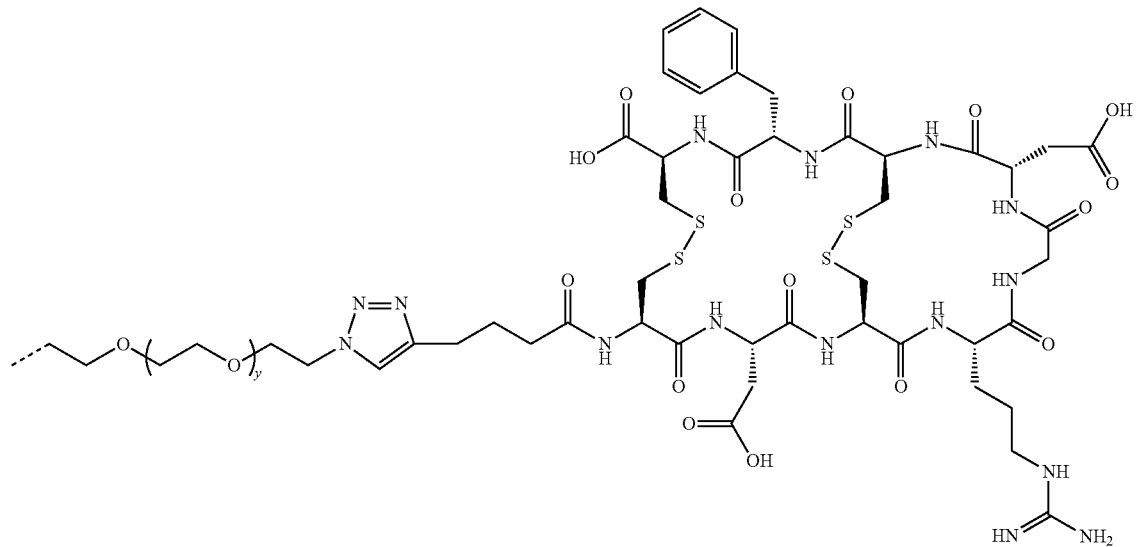
xxxv
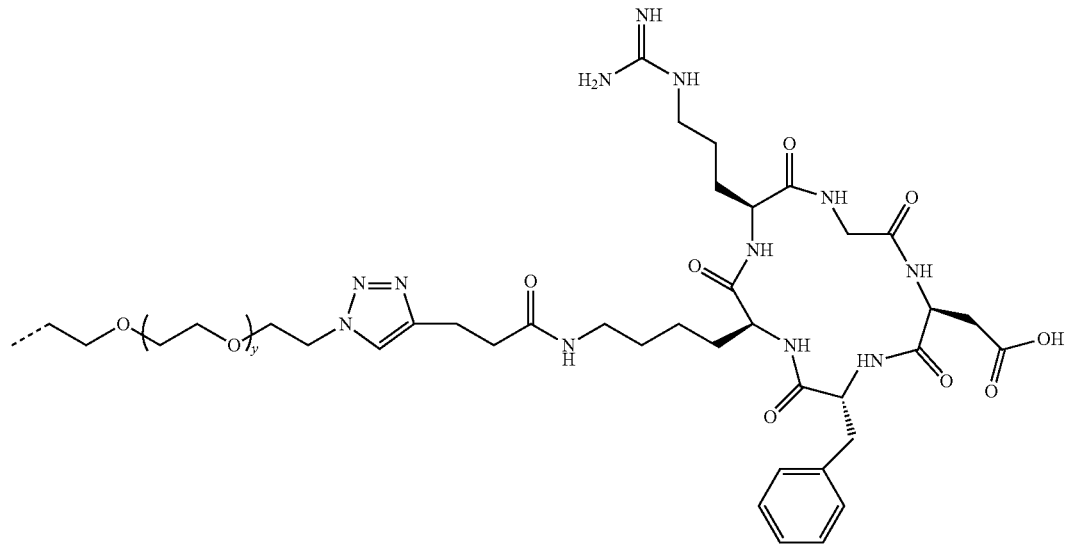

xxxvii
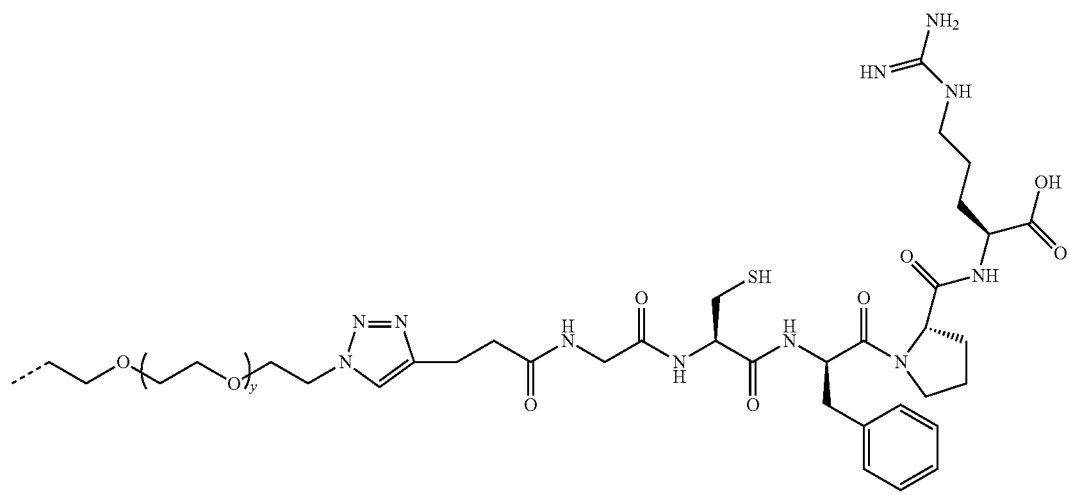
xxxxii
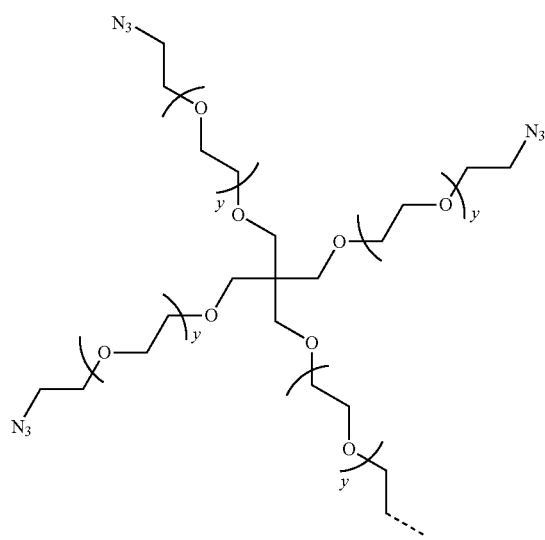
xxxxiii
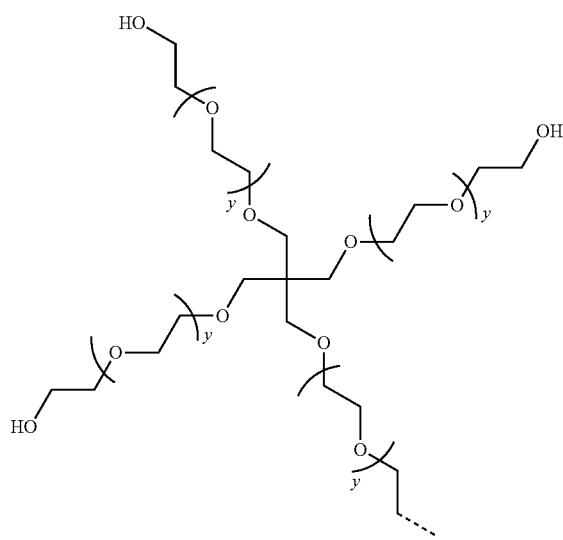
xxxxiv
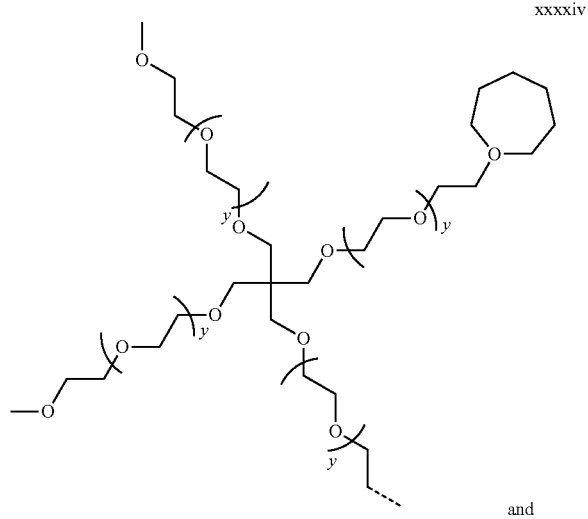
and -continued xxxxv

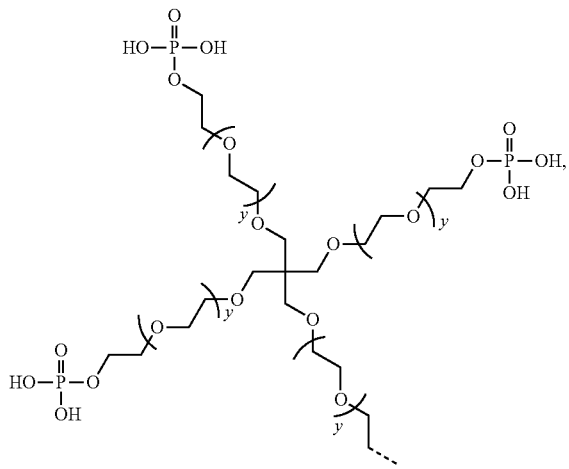

wherein:

each n is about 200 to about 300, or about 200 to about 250, or about 100 to about 150, or about 400 to about 500; and each y is about 10 to about 40, or about 40 to about 60, or about 90 to about 150, or about 200 to about 250, or about 300 to about 375, or about 400 to about 500.

10. The method according to claim 5, wherein the metal substrate comprises iron.

11. The method according to claim 5, wherein the metal substrate is selected from a stainless steel, a cobalt alloy, a titanium alloy, an iron alloy, steel, stainless steel, austenitic stainless steel, Type 316 stainless steel, ferritic stainless steel, martensitic stainless steel, duplex stainless steel, cobalt, a cobalt alloy, a cobalt-chromium alloy, stellite alloys, titanium, titanium alloy, or a super-alloy.

* * * * *